US010638735B2

(12) United States Patent
Grosveld et al.

(10) Patent No.: US 10,638,735 B2
(45) Date of Patent: May 5, 2020

(54) GENERATION OF HEAVY-CHAIN ONLY ANTIBODIES IN TRANSGENIC ANIMALS

(71) Applicants: ERASMUS UNIVERSITY MEDICAL CENTER ROTTERDAM, Rotterdam (NL); Roger Kingdon Craig, Sandbach (GB)

(72) Inventors: Franklin Gerardus Grosveld, Rotterdam (NL); Richard Wilhelm Janssens, Rotterdam (NL); Roger Kingdon Craig, Sandbach (GB)

(73) Assignee: Erasmus University Medical Center, Rotterdam (NL)

( * ) Notice: Subject to any disclaimer, the term of this patent is extended or adjusted under 35 U.S.C. 154(b) by 92 days.

(21) Appl. No.: 14/962,335

(22) Filed: Dec. 8, 2015

(65) Prior Publication Data
US 2016/0295843 A1    Oct. 13, 2016

Related U.S. Application Data

(63) Continuation of application No. 12/161,981, filed as application No. PCT/IB2007/001491 on Jan. 25, 2007, now abandoned.

(30) Foreign Application Priority Data

Jan. 25, 2006 (GB) .................................. 0601511.9
Sep. 18, 2006 (GB) .................................. 0618345.3

(51) Int. Cl.
| C07K 16/00 | (2006.01) |
| C12N 15/85 | (2006.01) |
| A01K 67/027 | (2006.01) |
| C07K 16/24 | (2006.01) |
| C07K 16/12 | (2006.01) |
| C07K 16/10 | (2006.01) |

(52) U.S. Cl.
CPC .......... *A01K 67/0278* (2013.01); *C07K 16/00* (2013.01); *C07K 16/1009* (2013.01); *C07K 16/1232* (2013.01); *C07K 16/1282* (2013.01); *C07K 16/1285* (2013.01); *C07K 16/241* (2013.01); *C12N 15/8509* (2013.01); *A01K 2207/15* (2013.01); *A01K 2217/00* (2013.01); *A01K 2217/05* (2013.01); *A01K 2217/072* (2013.01); *A01K 2217/075* (2013.01); *A01K 2227/105* (2013.01); *A01K 2267/01* (2013.01); *C07K 2317/24* (2013.01); *C07K 2317/569* (2013.01); *C12N 2015/8518* (2013.01)

(58) Field of Classification Search
CPC ............ A01K 2207/00; A01K 2217/05; A01K 2267/01; C07K 16/00; C07K 16/461; C07K 2317/24; C07K 2317/569; C12N 15/85; C12N 15/8509; C12N 15/8518

See application file for complete search history.

(56) References Cited

U.S. PATENT DOCUMENTS

| 8,883,150 | B2 * | 11/2014 | Craig | .................... C07K 16/00 |
| | | | | 424/133.1 |
| 8,921,522 | B2 * | 12/2014 | Grosveld | ............... C07K 16/00 |
| | | | | 530/387.1 |
| 8,921,524 | B2 * | 12/2014 | Grosveld | ............... C07K 16/00 |
| | | | | 424/132.1 |
| 9,346,877 | B2 * | 5/2016 | Grosveld | ............... C07K 16/00 |
| 9,353,179 | B2 * | 5/2016 | Grosveld | ............... C07K 16/00 |
| 9,365,655 | B2 * | 6/2016 | Craig | .................... C07K 16/00 |
| 2003/0070185 | A1 | 4/2003 | Jakobovits | |
| 2005/0287630 | A1 | 12/2005 | Kucherlapati | |
| 2006/0026703 | A1 | 2/2006 | Lonberg | |
| 2009/0307787 | A1 | 12/2009 | Grosveld | |

FOREIGN PATENT DOCUMENTS

| EP | 1690935 | 8/2006 |
| WO | 9201047 | 1/1992 |
| WO | 9402602 | 2/1994 |
| WO | 9634096 | 10/1996 |
| WO | 0212437 A2 | 2/2002 |
| WO | 02085945 A2 | 10/2002 |
| WO | WO 02/085944 | * 10/2002 |
| WO | 2004049794 A2 | 6/2004 |
| WO | 2005073251 | 8/2005 |
| WO | 2006008548 A2 | 1/2006 |

OTHER PUBLICATIONS

Nicholson et al, J. Immunol. 163:6898-6906, 1999.*
Corcos et al, Eur. J. Immunol. 21: 2711-2716, 1991.*
Zou et al, J. Immunol. 175: 3769-3779, 2005.*
Alt, F.W. et al., "Ordered rearrangement of immunoglobulin heavy chain variable region segments," The EMBO Journal, vol. 3, No. 6, 1984, pp. 1209-1219.
Brandt, C.R., et al., Loss of a Consensus Splice Signal in a Mutant Immunoglobulin Gene Eliminates the CH.sub.1 Domain Exon from the mRNA, Molecular and Cellular Biology, vol. 4, No. 7, pp. 1270-1277, 1984.
Bryda et al, BioTechniques 41:715-719, 2006.
Co-pending U.S. Appl. No. 12/161,981, filed Sep. 15, 2008.
Corcos, et al., 'Allelic exclusion in transgenic mice expressing a heavy chain disease-like human u protein', Eur. J. Immunol., vol. 21, pp. 2711-2716, 1991.

(Continued)

*Primary Examiner* — Kevin K Hill
(74) *Attorney, Agent, or Firm* — Saul Ewing Arnstein & Lehr LLP; Doreen Y. Trujillo

(57) ABSTRACT

The present invention relates to a method for the generation of $V_H$ heavy chain-only antibodies in a transgenic non-human mammal. In particular, the present invention relates to a method for the production of a $V_H$ heavy chain-only antibody in a transgenic non-human mammal comprising the step of expressing more than one heterologous $V_H$ heavy chain locus in that mammal.

17 Claims, 24 Drawing Sheets

Figure 1:
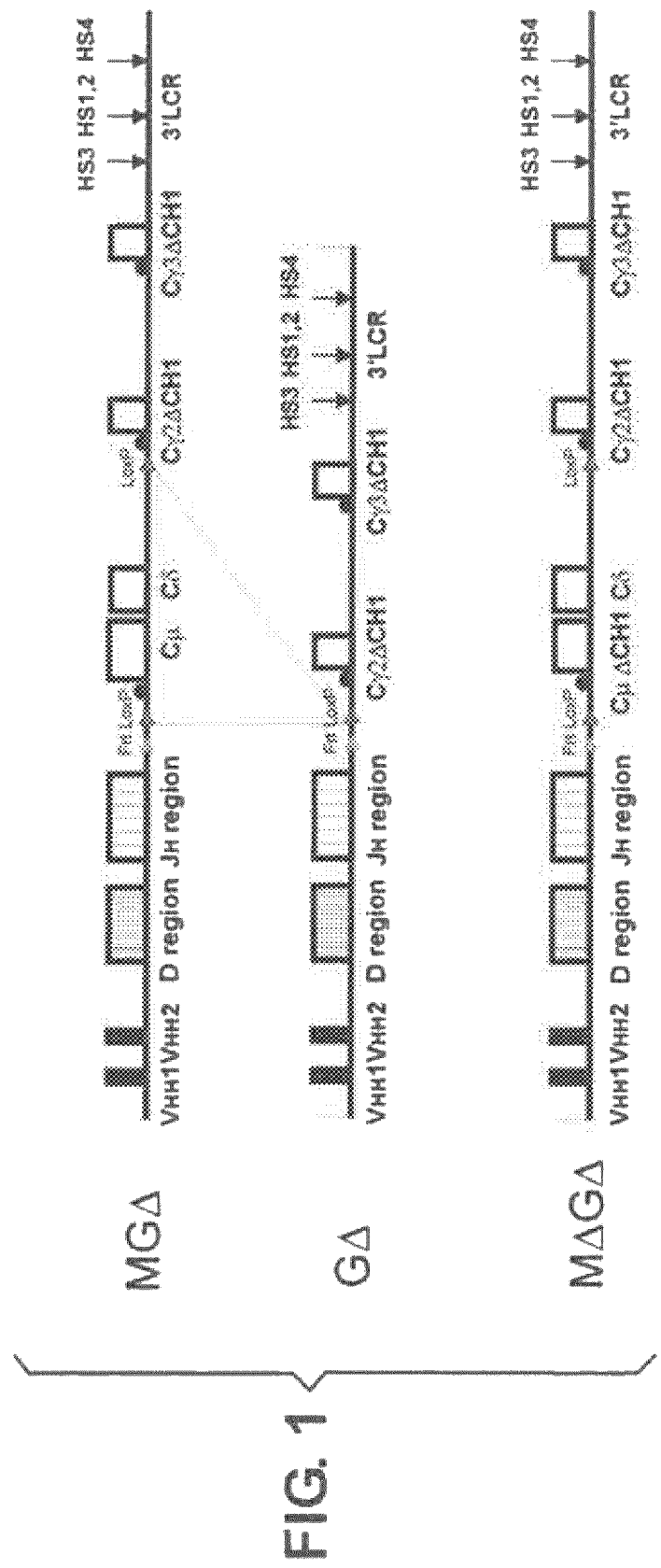

Specification includes a Sequence Listing.

(56) References Cited

OTHER PUBLICATIONS

Corcos, et al., 'Pre-B-cell development in the absence of lambda 5 in transgenic mice expressing a heavy-chain disease protein', Curr. Biol., vol. 5, pp. 1140-1148, 1995.
Corput, et al., 'Fluorescence in situ hybridization analysis of transcript dynamics in cells', Methods, vol. 25, pp. 111-118, 2001.
Costa, T.E.F. et al., "Chromosomal Position of Rearranging Gene Segments Influences Allelic Exclusion in Transgenic Mice," Proc. Natl. Acad. Sci. USA, vol. 89, pp. 2205-2208, 1992.
Davies & Riechmann, "Antibody VH Domains as Small Recognition Units," BioTechnology, May 1995, vol. 13, pp. 475-479, Nature Publishing Group.
Davies, J., 'Single antibody domains as small recognition units: design and in vitro antigen selection of camelized, human VH domains with improved protein stability', Protein Engineering, vol. 9, No. 6, pp. 531-537, 1996.
Davis CG, et al., 'Production of human antibodies from transgenic mice', Methods Mol. Biol., vol. 248, pp. 191-200, 2004.
De Genst, et al., 'Antibody repertoire development in camelids', Dev Comp Immunol., vol. 30, Nos. 1-2, pp. 187-198, 2006.
De Genst, et al., 'Strong in Vivo Maturation Compensates for Structurally Restricted H3 Loops in Antibody Repertoires', J. Biol. Chem., vol. 280, No. 14, pp. 14114-14121, 2005.
Dekker, et al., 'Intracellularly Expressed Single-Domain Antibody against p15 Matrix Protein Prevents the Production of Porcine Retroviruses', J Virol., vol. 77, No. 22, pp. 12132-12139, 2003.
Dolk, E., et al., 'Isolation of Llama Antibody Fragments for Prevention of Dandruff by Phage Display in Shampoo', Applied Environmental Microbiology, vol. 71, No. 1, pp. 442-450, 2005.
Dolk, et al., "Induced refolding of a temperature denatured llama heavy-chain antibody fragment by its antigen", Proteins, vol. 59, No. 3, pp. 555-564, 2005.
Eason, et al., "Expression of individual immunolgobulin genes occurs n an unusual system consisting of multiple independent loci", Eur. J. Immunol., vol. 34, pp. 2551-2558, 2004.
European Communication pursuant to Rule 114(2) EPC dated May 23, 2016 for European Application No. 07734772.2 (pp. 1-9).
Fishwild, D.M. et al., "High-avidity Human IgGk Monoclonal Antibodies from a Novel Strain of Minilocus Transgenic Mice," Nat. Biotech., vol. 14, pp. 845-851, 1996.
Hamers-Casterman, C., et al., 'Naturally occurring antibodies devoid of light chains', Nature, vol. 363, No. 6428, pp. 446-448, 1993.
Hasan, et al., 'Incomplete block of B cell development and antibody production in mice carrying the muMT mutation on the BALB/c background', Eur. J. Immunol, vol. 32, pp. 3463-3471, 2002.
Heiskanen, et al, 'Visual mapping by fiber-FISH', Genomics, vol. 30, pp. 31-36, 1995.
Hendershot, Linda et al., Assembly and Secretion of Heavy Chains that Do Not Associate Posttranslationally with Immunoglobulin Heavy Chain-binding Protein, The Journal of Cell Biology, Mar. 1987, pp. 761-767, vol. 104, The Rockefeller University Press.
Hoogenboom, et al., 'Multi-subunit proteins on the surface of filamentous phage: methodologies for displaying antibody (Fab) heavy and light chains', Nucleic Acids Research, vol. 19, 4133-4137, 1991.
Iglesias, A. et al., "Expression of immunoglobulin delta chain causes allelic exclusion in transgenic mice," Nature, Dec. 3, 1987, vol. 330, No. 6147, pp. 482-484.
Iglesias, et al., 'Molecular requirements for the u-induced light chain gene rearrangement in pre-B cells', EmboJ., vol. 10, pp. 2147-2155, 1991.
Imam, et al., 'Modification of human (3-globin locus PAC clones by homologous recombination in E. coli', Nucleic Acids Res., vol. 15 E65, 2001.
International Search Report dated May 2, 2008 for PCT/IB2007/001491; Publication No. WO2007/096779 "Generation of heavy-chain only antibodies".
Jakobovits, A., 'The long-awaited magic bullets: therapeutic human monoclonal antibodies from transgenic mice', Expert Opin Investig Drugs, vol. 7, No. 4, pp. 607-614, 1998.
Janssens, R., et al., 'Generation of heavy-chain-only antibodies in mice', Proc. Natl. Acad. Sci. USA, vol. 103, No. 41, pp. 15130-15135, 2006.
Jaton, J.C., et al., 'Recovery of Antibody Activity upon Reoxidation of Completely Reduced Polyalanyl Heavy Chain and Its Fd Fragment Derived from Anti-2,4-dinitrophenyl Antibody', Biochemistry, vol. 7, No. 12, pp. 4185-4195, Dec. 1968.
Jespers, et al., 'Aggregation-resistant domain antibodies selected on phage by heat denaturation', Nat. Biotechnol., vol. 22, No. 9, pp. 1161-1165, 2004.
Jespers, et al., 'Crystal structure of HEL4, a soluble, refoldable human V(H) single domain with a germ-line scaffold', J. Mol. Biol., vol. 337, No. 4, pp. 893-903, 2004.
Jung, et al., 'Mechanism and control of V(D)J recombination at the immunoglobulin heavy chain locus', Annual Review of Immunology, vol. 24, pp. 541-570, 2006.
Kellermann, SA, et al., 'Antibody discovery: the use of transgenic mice to generate human monoclonal antibodies for therapeutics', Curr Opin Biotechnol., vol. 13, No. 6, pp. 593-597, 2002 (links).
Kitamura, Daisuke et al., A B cell-deficient mouse by targeted disruption of the membrane exon of the immunoglobulin u chain gene, Nature, Apr. 4, 1991, pp. 423-426, vol. 350, Nature Publishing Group.
Lefranc et al., 'IMGT, the international ImMunoGeneTics database,' Nucleic Acids Research, vol. 27, No. 1, pp. 209-212(1999).
Leher, et al., Monoclonal IgA antibodies protect against Acanthamoeba keratitis, Exp. Eye. Res., vol. 69, No. 1, pp. 75-84, 1999.
MacPherson, et al., 'IgA production without mu or delta chain expression in developing B cells', Nat. Immunol. vol. 2, pp. 625-632, 2001.
Melamed, D., and Nemazee D., 'Self-antigen does not accelerate immature B cell apoptosis, but stimulates receptor editing as a consequence of developmental arrest', Proc. Natl. Acad. Sci., vol. 94, pp. 9267-9272, 1997.
Middendorp, et al., 'Impaired precursor B cell differentiation in Bruton's tyrosine kinase-deficient mice', J. Immunol., vol. 168, pp. 2695-2703, 2002.
Mills, et al., Enhancer Complexes Located Downstream of Both Human Immunoglobulin Ca Genes, The Journal of Experimental Medicine, vol. 186, No. 6, pp. 845-858, 1997.
Mundt, et al., 'Loss of precursor B Cell expansion but not allelic exclusion in VpreB1A/preB2 double deficient mice', J. Exp. Med., vol. 193, pp. 435-445, 2001.
Nguyen, et al., 'Loss of splice consensus signal is responsible for the removal of the entire C(H)1 domain of the functional camel IGG2A heavy-chain antibodies', Mol. Immunol., vol. 36, pp. 515-524, 1999.
Nicholson, I.C., et al., 'Antibody Repertoires of Four- and Five-Feature Translocus Mice Carrying Human Immunoglobulin Heavy Chain and {kappa} and {lambda} Light Chain Yeast Artificial Chromosomes,' The Journal of Immunology 163 (12), pp. 6898-6906 (Dec. 15, 1999), The William and Wilkins Co, Baltimore, MD.
Nussenzweig, M.C. et al., "Allelic exclusion in transgenic mice that express the membrane form of immunoglobulin mu," Science, May 15, 1987, vol. 236, No. 4803, pp. 816-819.
Orinska, Zane et al., Novel B cell population producing functional IgG in the absence of membrane IgM expression, European Journal of Immunology, 2002, pp. 3472-3480, vol. 32, Wiley-VCH Verlag GmbH & Co., KGaA, Weinheim.
Pogue, et al., 'Gene dose-dependent maturation and receptor editing of B cells expressing Immunoglobulin antibody (Ig)G1 or IgM/IgG1 tail antigen receptors', J. Exp. Med., vol. 191, pp. 1031-1044, 2000.
Ravn, et al., 'Multivalent scFv display of phagemid repertoires for the selection of carbohydrate-specific antibodies and its application to the Thomsen Friedenreich antigen', J. Mol. Biol., vol. 343, No. 4, pp. 985-996, 2004.
Riechmann, L., et al., 'Single domain antibodies: comparison of camel VH and camelised human VH domains', J. Immunol. Methods, vol. 231, Nos. 1-2, pp. 25-38, 1999.
Seidl, et al., "The VpreB protein of the surrogate lightchain can pair with some u heavy-chains in the absence of the lambda 5 protein", Eur. J. Immunol, vol. 31, pp. 1999-2006, 2001.

(56) References Cited

OTHER PUBLICATIONS

Shaffer & Schlissel, 'A truncated heavy chain protein relieves the requirement for surrogate light chains in early B cell development', J. Immunol., vol. 159, pp. 1265-1275, 1997.
Sitia, R., et al., 'Developmental regulation of IgM secretion: The role of the carboxy-terminal cysteine,' Cell, vol. 60, No. 5, pp. 781-790, 1990.
Sonoda, et al., "B cell development under the condition of allelic inclusion", Immunity, vol. 6, pp. 225-233, 1997.
Stanfield, et al., 'Crystal Structure of a Shark Single-Domain Antibody V Region in Complex with Lysozyme', Science, vol. 305, No. 5691, pp. 1770-1773, 2004.
Storb, U., "Transgenic Mice with Immunoglobulin Genes," Ann. Rev. Immunol., vol. 5, pp. 151-174, 1987.
Su, et al., 'Identification of a pre-BCR lacking surrogate light chain', J. Exp. Med. vol. 198, pp. 1699-1706, 2003.
Tanha, J., et al., 'Optimal Design Features of Camelized Human Single-domain Antibody Libraries', The Journal of Biological Chemistry, vol. 276, No. 27, pp. 24774-24780, Jul. 6, 2001.
Urlinger, et al., "Exploring the sequence space for tetracycline-dependent transcriptional activators: novel mutations yield expanded range and sensitivity", Proc. Natl. Acad. Sci. USA, vol. 97, pp. 7963-7968, 2000.
Van Der Linden, et al., "Induction of immune response and molecular cloning of heavy chain repertoire of lama glama", J. Immunol., Methods., vol. 240, pp. 185-195, 2000.
Van Dijk and Van Der Winkel, 'Human antibodies as next generation therapeutics', Curr. Opin. Chem. Biol., vol. 5, No. 4, pp. 368-374, 2001.
Van Spriel, et al., 'Immunotherapeutic perspective for bispecific antibodies', Immunology Today, vol. 21, No. 8, pp. 391-397, 2000.
Vettermann, C. et al., "Allelic exclusion of immunoglobulin genes: models and mechanisms," Immunol. Rev. Sep. 2010, vol. 237, No. 1, pp. 22-42.
Vu, Khoa Bang et al., Comparison of Llama VH Sequences From Conventional and Heavy Chain Antibodies, Molecular Immunology, 1997, pp. 1121-1131, vol. 34, No. 16-17, Elsevier Sciences, Ltd., Pergamon PII: S0161-5890 (97)00146-6, Great Britain.
Wagner, et al., 'Antibody expression from the core region of the human IgH locus reconstructed in transgenic mice using bacteriophage PI clones', Genomics, vol. 35, pp. 405-414, 1996.
Ward, et al., 'Binding activities of a repertoire of single immunoglobulin variable domains secreted from *Escherichia coli*', Nature, vol. 341, pp. 544-546, 1989.
Xu, J.L., and Davis, M.M., 'Diversity in the CDR3 region of V(H) is sufficient for most antibody specificities', Immunity, vol. 13, pp. 37-45, 2000.
Yau, et al., 'Affinity maturation of a V(H)H by mutational hotspot randomization', J. Imunol. Methods, vol. 297, Nos. 1-2, pp. 213-224, 2005.
Zemlin, M, et al., "Expressed murine and human CDR-H3 intervals of equal length exhibit distinct repertoires that differ in their amino acid composition and predicted range of structures", J. Mol. Biol., vol. 334, pp. 733-749, 2003.
Zhao, et al., "Selective IgG2 deficiency due to a point mutation causing abnormal splicing of the Cgamma2 gene," Int. Immunol., vol. 17, pp. 95-101, 2005.
Zou, X., et al., "Expression of a Dromedary Heavy Chain-Only Antibody and B Cell Development in the Mouse," J. Immunology, vol. 175, pp. 3769-3779, 2005.
Navas, Patrick A., et al., "Developmental Specificity of the Interaction between the Locus Control Region and Embryonic or Fetal Globin Genes in Transgenic Mice with an HS3 Core Deletion," Molecular and Cellular Biology, Jul. 1998, vol. 18, No. 7, pp. 4188-4196.

\* cited by examiner

% of B220+/CD19+ cells in total population of nucleated cells

| | WT | GΔ (~5 copies) | GΔ (single copy) | MAGA |
|---|---|---|---|---|
| BM | 10.80 ± 2.09 | 5.94 ± 1.44 | 4.93 ± 1.79 | 6.06 ± 1.53 |
| Spleen | 41.80 ± 6.05 | 32.14 ± 9.46 | 28.70 ± 8.70 | 33.95 ± 3.24 |
| Blood | 43.72 ± 7.50 | 16.00 ± 5.68 | 16.01 ± 3.76 | 9.25 ± 3.24 |
| Peritoneum | 21.92 ± 9.90 | *22.85 ± 6.71 | *22.30 ± 7.29 | 21.21 ± 14.42 |

Mice were 14-20 weeks old. Numbers of mice analyzed are 5-11 per mouse line with the exception of two peritoneal cells measurements, where calculations are based on two samples (marked by asterisks).

Fig. 2A

Fig. 2D

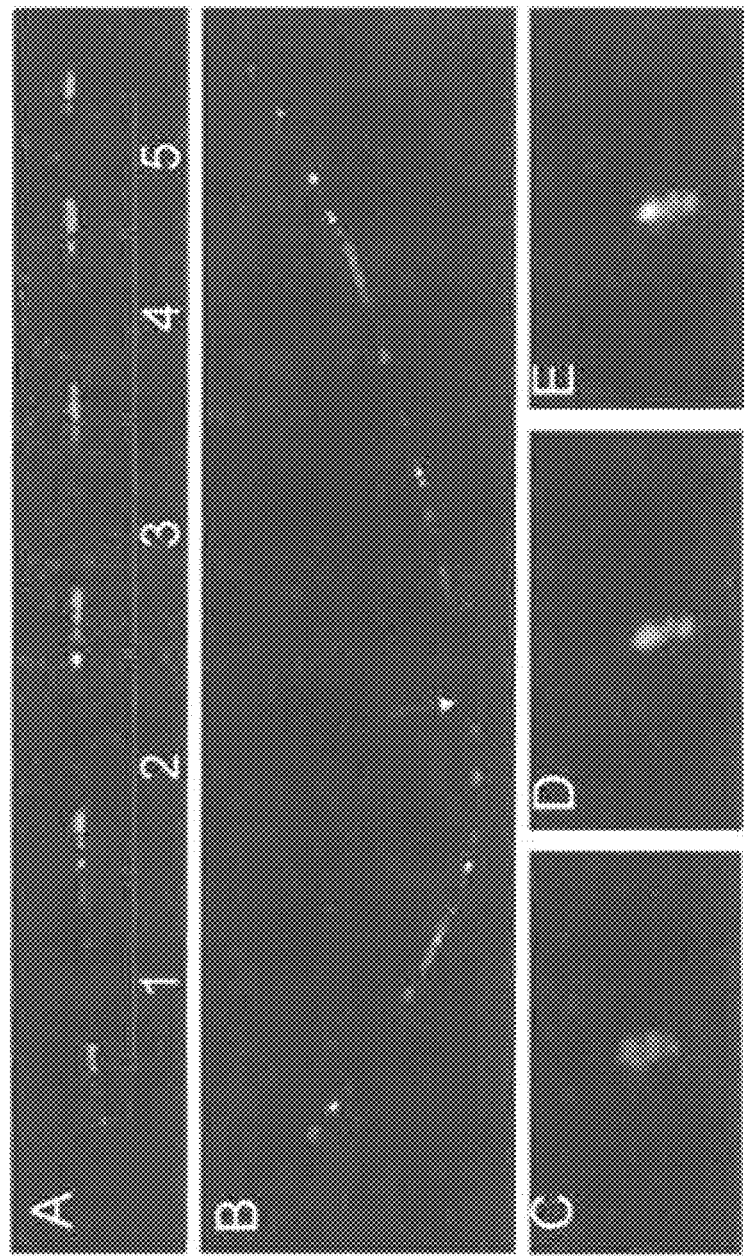
Fig. 3A-E

| | | CDR1 | CDR2 | |
|---|---|---|---|---|
| Germline VHH1 | RLSCAASGFTLDYYAIGWFRQAEGKEREGVSCISSSDGSTYYADSVKGRFTISRDNAKN | | | |
| Clone 1 | RLSCAASGFTLDYYAIGWFRQAEGKEREGVSCISSSDGSTYYADSVKGRFTISRDNAKN | | | |
| Clone 2 | RLSCAASGFTLDYYVIGWFRQAEGKEREGVSCISSSDGSTYYADSVKGRFTISRPNAKN | | | |
| Clone 3 | RLSCAASGFTLDYYAIGWFRQAEGKEREGVSCISSSDGSTYYGDSVKGRFTISRDKAKN | | | |
| Germline VHH2 | RLSCAASGSIFSINAMGWYRQAPGKQRELVAAITSGGSTNYADSVKGRFTISRDNAKN | | | |
| Clone 4 | RLSCAASGSIFSINAMGWYRQAPGKQRELVAAITSGGSTKYADSVKGRFTISRDNAKN | | | |
| Clone 5 | RLSCAASGSIFSINVMGWYRQPPGKQRELVAGVTSGGSTSYADSVKGRFTISRDNAKN | | | |
| Clone 6 | RLSCAASGSIFSINAMGWYRQAPGKQRELVAPITSGGSTNYADSVKGRFTISRDNAKN | | | |

Fig. 4C

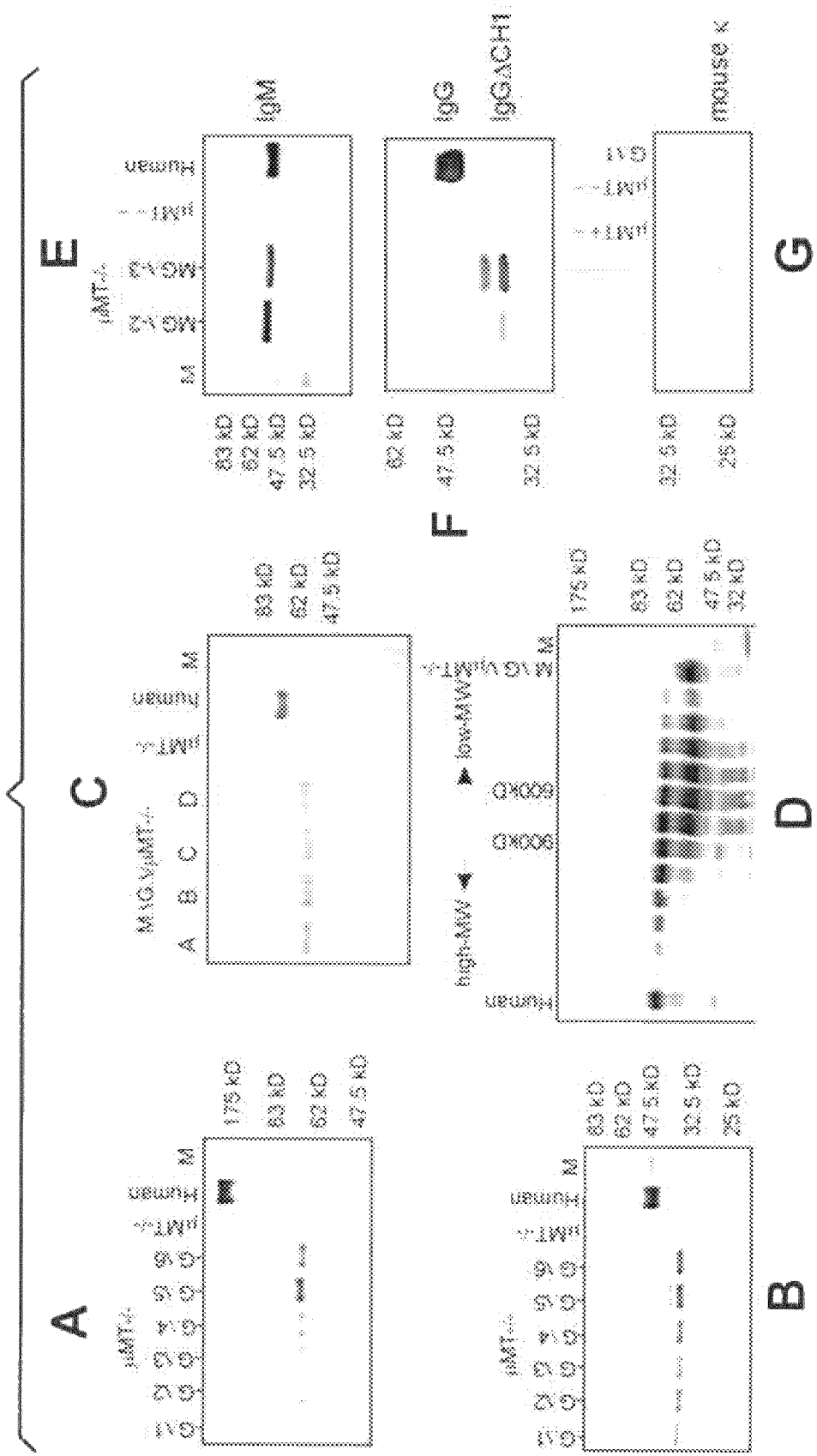
Fig. 6A-G

|                | CDR1 | CDR2 |
|---|---|---|

```
              CDR1                                    CDR2
VHH2 germline  RLSCAASGSIFSINAMGWYRQAPGKQRELVAAITSGGSTNYADSVKGRFTISRDNAKNTVYL..cont
α-B.Pertussis 1 RLSCAASGSIFSINAM

Fig. 8B

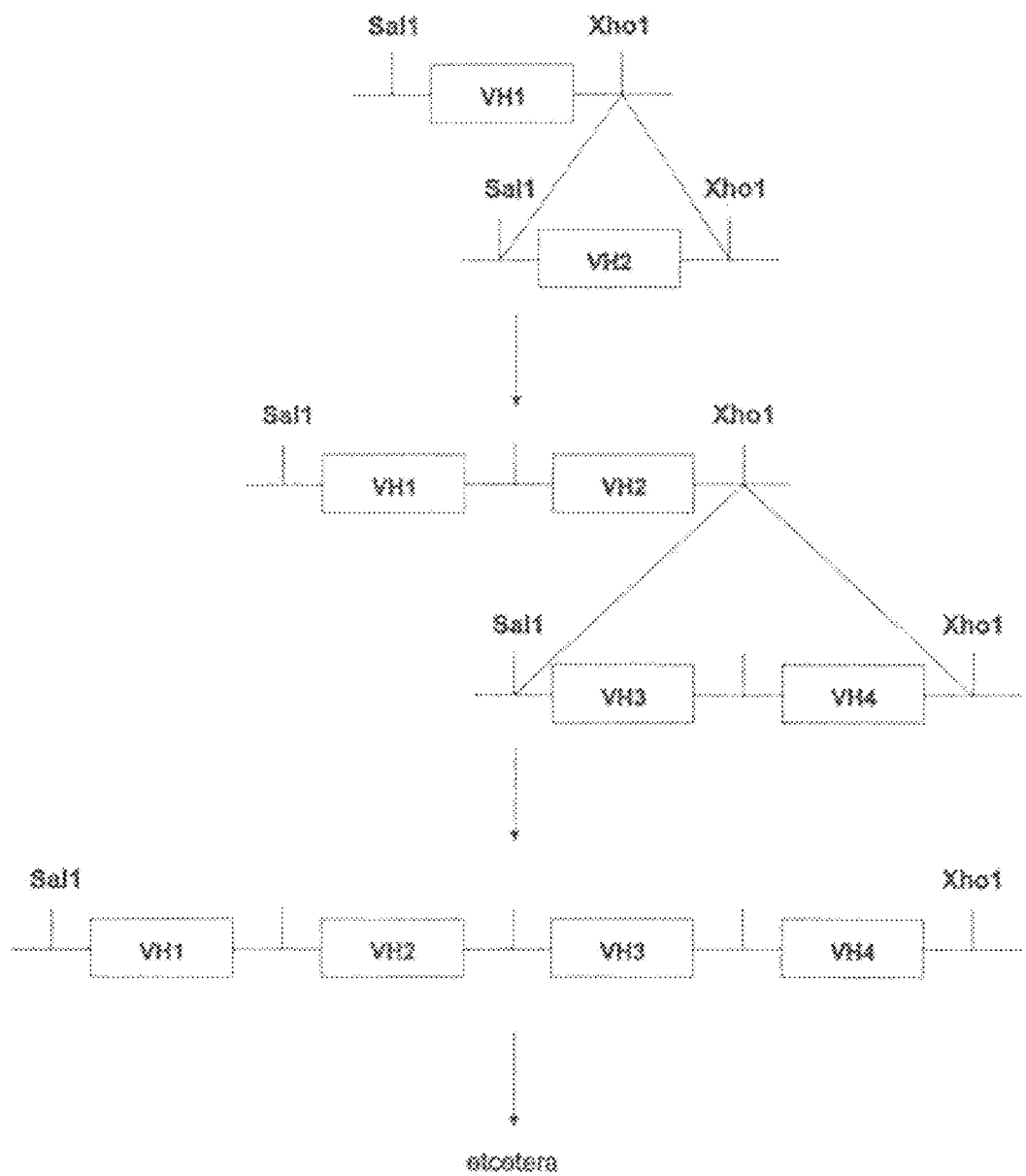

GENERATION OF HEAVY-CHAIN ONLY ANTIBODIES IN TRANSGENIC ANIMALS

CROSS-REFERENCE TO RELATED APPLICATIONS

The present application is a continuation of application Ser. No. 12/161,981, filed Sep. 15, 2008, now abandoned, which is a 371 national phase application of PCT/IB2007/001491, filed Jan. 25, 2007, which claims priority to GB 0601511.9, filed Jan. 25, 2006 and GB 0618345.3, filed Sep. 18, 2006, each of which are incorporated herein by reference in its entirety.

FIELD OF THE INVENTION

The present invention relates to improved methods for the manufacture in transgenic non-human mammals of a diverse repertoire of functional, affinity-matured heavy chain-only antibodies in response to antigen challenge and uses thereof. The invention also relates to the manufacture of a diverse repertoire of class-specific heavy chain-only antibodies from multiple loci.

In particular, the present invention relates to a method for the generation of human antigen-specific, high affinity, heavy chain-only antibodies of any class or mixture of classes and the isolation and expression of fully functional $V_H$ antigen-binding domains. Heavy chain-only antibodies generated using the methods of the present invention are also described.

In the following description, all amino acid residue position numbers are given according to the numbering system devised by Kabat et at, [1].

BACKGROUND TO THE INVENTION

Antibodies

The structure of antibodies is well known in the art. Most natural antibodies are tetrameric, comprising two heavy chains and two light chains. The heavy chains are joined to each other via disulphide bonds between hinge domains located approximately half way along each heavy chain. A light chain is associated with each heavy chain on the N-terminal side of the hinge domain. Each light chain is normally bound to its respective heavy chain by a disulphide bond close to the hinge domain.

When an antibody molecule is correctly folded, each chain folds into a number of distinct globular domains joined by more linear polypeptide sequences. For example, the light chain folds into a variable ($V_L$) and a constant (CO domain. Heavy chains have a single variable domain $V_H$, a first constant domain ($C_H 1$), A hinge domain and two or three further constant domains. The heavy chain constant domains and the hinge domain together form what is generally known as the constant region of an antibody heavy chain. Interaction of the heavy ($V_H$) and light ($V_L$) chain variable domains results in the formation of an antigen binding region ($F_v$). Interaction of the heavy and light chains is facilitated by the $C_H1$ domain of the heavy chain and the $C_K$ or $C\lambda$ domain of the light chain. Generally, both $V_H$ and $V_L$ are required for antigen binding, although heavy chain dimers and amino-terminal fragments have been shown to retain activity in the absence of light chain [2].

Within the variable domains of both heavy ($V_H$) and light ($V_L$) chains, some short polypeptide segments show exceptional variability. These segments are termed hypervariable regions or complementarity determining regions (CDRs). The intervening segments are called framework regions (FRs). In each of the $V_H$ and $V_L$ domains, there are three CDRs (CDR1-CDR3).

In mammals there are five classes of antibody: IgA, IgD, IgE, IgG and IgM, with four IgG and two IgA subtypes present in humans.

| Class | H chain | L chain | Subunits | mg/ml | Notes |
|---|---|---|---|---|---|
| IgG | gamma | Kappa or lambda | $H_2L_2$ | 6-13 | transferred across placenta |
| IgM | mu | kappa or lambda | $(H_2L_2)_5$ | 0.5-3 | first antibodies to appear after immunization |
| IgA | alpha | kappa or lambda | $(H_2L_2)_2$ | 0.6-3 | much higher concentrations in secretions |
| IgD | delta | kappa or lambda | $H_2L_2$ | <0.14 | function uncertain |
| IgE | epsilon | kappa or lambda | $H_2L_2$ | <0.0004 | binds to basophils and mast cells sensitizing them for certain allergic reactions |

Antibody classes differ in their physiological function. For example, IgG plays a dominant role in a mature immune response. IgM is involved in complement fixing and agglutination. IgA is the major class of antibody in secretions—tears, saliva, colostrum, mucus—and thus plays a role in local immunity. The effector functions of natural antibodies are provided by the heavy chain constant region.

IgA can be found in areas containing mucus (e.g. in the gut, in the respiratory tract or in the urinogenital tract) and prevents the colonization of mucosal areas by pathogens. IgD functions mainly as an antigen receptor on B cells. IgE binds to allergens and triggers histamine release from mast cells (the underlying mechanism of allergy) and also provides protection against helminths (worms). IgG (in its four isotypes) provides the majority of antibody-based immunity against invading pathogens. IgM is expressed on the surface of B cells and also in a secreted form with very high affinity for eliminating pathogens in the early stages of B cell mediated immunity (i.e. before there is sufficient IgG to eliminate the pathogens).

Normal human B cells contain a single heavy chain locus on chromosome 14 from which the gene encoding a heavy chain is produced by rearrangement. In the mouse the heavy chain locus is located on chromosome 12. A normal heavy chain locus comprises a plurality of V gene segments, a number of D gene segments and a number of J gene segments. Most of a $V_H$ domain is encoded by a V gene segment, but the C terminal end of each $V_H$ domain is encoded by a D gene segment and a J gene segment. VDJ rearrangement in B-cells, followed by affinity maturation, provides each $V_H$ domain with its antigen binding specificity. Sequence analysis of normal $H_2L_2$ tetramers demonstrates that diversity results primarily from a combination of VDJ rearrangement and somatic hypermutation [3], There are over 50 human V gene segments present in the human genome of which only 39 are functional.

Fully human antibodies ($H_2L_2$) can now be derived from transgenic mice in response to antigen challenge. Such transgenic mice comprise a single human heavy chain locus and a separate light chain locus. The comparable mouse heavy and light chain loci are deleted or suppressed so that only human antibodies are produced in the absence of mouse antibodies ([4-10]).

With the advent of new molecular biology techniques, the presence of heavy chain-only antibody (devoid of light chain) was identified in B-cell proliferative disorders in man (Heavy Chain Disease) and in murine model systems. Analysis of heavy chain disease at the molecular level showed that mutations and deletions at the level of the genome could result in inappropriate expression of the heavy chain $C_H1$ domain, giving rise to the expression of heavy chain-only antibody lacking the ability to bind light chain [11,12], It has been shown that camelids, as a result of natural gene mutations, produce functional IgG2 and IgG3 heavy chain-only dimers which are unable to bind light chain due to the absence of the $C_H1$ domain, which mediates binding to the light chain [13]. A characterising feature of the camelid heavy chain-only antibody is a particular subset of camelid $V_H$ domains, which provides improved solubility relative to human and normal camelid $V_H$ domains. The camelid $V_H$ domains in this particular subset are usually referred to as $V_{HH}$ domains.

It has also been shown that species such as shark produce a heavy chain-only-like binding protein family, probably related to the mammalian T-cell receptor or antibody light chain [14].

For the production of camelid heavy chain-only antibody, the heavy chain locus in the camelid germline comprises gene segments encoding some or all of the possible heavy chain constant regions. During maturation, a re-arranged $V_{HH}DJ$ binding domain is spliced onto the 5' end of the gene segment encoding the hinge domain, to provide a rearranged gene encoding a heavy chain which lacks a $C_H1$ domain and is therefore unable to associate with a light chain.

Camelid $V_{HH}$ domains contain a number of characteristic amino acids at positions 37, 44, 45 and 47 [49]. These conserved amino acids are thought to be important for conferring solubility on heavy chain-only antibodies. Only certain camelid $V_H$ domains are $V_{HH}$ domains with improved solubility characteristics. They are limited to $V_H$ subfamily and so respond productively only to a limited range of antigens.

Heavy chain-only monoclonal antibodies can be recovered from B-cells of camelid spleen by standard cloning technology or from B-cell mRNA by phage or other display technology [18]. Heavy chain-only antibodies derived from camelids are of high affinity. Sequence analysis of mRNA encoding heavy chain-only antibody demonstrates that diversity results primarily from a combination of $V_{HH}DJ$ rearrangement and somatic hypermutation [49] as is also observed in the production of normal tetrameric antibodies. An important and common feature of natural camelid and human $V_H$ domains is that each domain binds as a monomer with no dependency on dimerisation with a $V_L$ domain for optimal solubility and binding affinity.

Recently, methods for the production of heavy chain-only antibodies in transgenic non-human mammals have been developed (see WO02/085945 and WO02/085944). Functional heavy chain-only antibody of potentially any class (IgM, IgG, IgD, IgA or IgE) and derived from any mammal can be produced from transgenic non-human mammals (preferably mice) as a result of antigen challenge. These initial studies relied on the use of two llama V gene segments and suffered from a limited repertoire of antibody response.

Janssens et al. [15] have developed methods for the derivation of heavy chain-only antibodies in transgenic mice. These heavy chain-only antibodies have high binding affinity as a result of antibody maturation in B-cells, can be derived as a result of antigen challenge and selected using established hybridoma technology and can be produced as any class of antibody in the absence of light chain (e.g. IgG, IgA, IgM) or as $V_H$ binding domains alone. These heavy chain-only antibodies were derived from an antibody heavy chain locus in a germline (i.e. non-rearranged) configuration that contained two llama $V_{HH}$ (class 3) gene segments coupled to all of the human D and J gene segments and gene segments encoding all the human constant regions. The gene segments encoding each of the constant regions had a deletion of the $C_H1$ domain to prevent the binding of light chains. In addition, the locus contained the antibody LCR at the 3' end to ensure a high level of expression in cells of the B lineage. This locus was introduced into the mice by microinjection of fertilized eggs.

Production of Antibody-Based Products

The production of antibody-based products by genetic engineering, in particular the production of human or humanised antibody-based products, has resulted in the generation of new classes of medicines, diagnostics and reagents and, in parallel, opportunity for new industry, employment and wealth creation (see www.drugresearcher.com, www.leaddiscoverv.co.uk). Antibody-based products are usually derived from natural tetrameric antibodies. There are many patents and applications which relate to the production of antibody-based products. These patents and applications relate to routes of derivation (e.g. from transgenic mice), routes of manufacture and product-specific substances of matter. Such antibody-based products vary from complete tetrameric antibodies through antibody fragments to single chain Fv (scFv) molecules.

Antibody-based products will represent a high proportion of new medicines launched in the $21^{st}$ century. Monoclonal antibody therapy is already accepted as a preferred route for the treatment for rheumatoid arthritis and Crohn's disease and there is impressive progress in the treatment of cancer. Antibody-based products are also in development for the treatment of cardiovascular and infectious diseases. Most marketed antibody-based products recognise and bind a single, well-defined epitope on the target ligand (e.g. TNFα).

Recently, high affinity $V_H$ domains have been: selected from randomised human $V_H$ domains in display libraries or derived from heavy chain-only antibody produced naturally from antigen challenge of camelids or derived from $V_H$ domain libraries made from camelids. These high affinity $V_H$ domains have been incorporated into antibody-based products. These $V_H$ domains, also called $V_{HH}$ domains, display a number of differences from classical $V_H$ domains, in particular a number of mutations that ensure improved solubility and stability of the heavy chains in the absence of light chains. Most prominent amongst these changes is the presence of a charged amino acid at position 45 [16].

A number of groups have worked on the generation of heavy chain-only antibodies derived from natural tetrameric antibodies. Jaton et al [2 and other references cited therein] describe the separation of the reduced heavy chain components of an affinity purified, well-characterised rabbit antibody, followed by the subsequent renaturation of the individual heavy chains. Immunological characterisation of the renatured heavy chains demonstrated that a heavy chain homodimer alone, free of light chain, is capable binding antigen.

Later Ward et al. [18] demonstrated unambiguously that cloned murine $V_H$ regions, when expressed as soluble protein monomers in an E. coli expression system, retain the ability to bind antigen with high affinity. Ward et al [18] describe the isolation and characterisation of $V_H$ domains and set out the potential commercial advantages of this approach when compared with classic monoclonal antibody production (see last paragraph). They also recognise that $V_H$ domains isolated from heavy chains which normally associate with a light chain lack the solubility of the natural tetrameric antibodies. Hence Ward et al [18] used the term "sticky" to describe these molecules and proposed that this "stickiness" can be addressed through the design of $V_H$ domains with improved solubility properties.

The improvement of $V_H$ solubility has subsequently been addressed using combinations of randomized and site-directed approaches using phage display. For example, Davies and Riechmann [17] and others (see WO92/01047) incorporated some of the features of $V_H$ domains from camelid heavy chain-only antibodies in combination with phage display to improve solubility whilst maintaining binding specificity.

Separate studies on isolated human $V_H$ domains derived from phage libraries demonstrated antigen-specific binding of $V_H$ domains but these $V_H$ domains proved to be of low solubility. Furthermore, it was suggested that the selection of human $V_H$ domains with specific binding characteristics displayed on phage arrays could form the building blocks for engineered antibodies [18].

Human $V_H$ domains may be engineered for improved solubility characteristics [19, 20] or solubility maybe be acquired by natural selection in vivo [21]. However, where $V_H$ binding domains have been derived from phage libraries, intrinsic affinities for antigen remain in the low micromolar to high nanomolar range, in spite of the application of affinity improvement strategies involving, for example, affinity hot spot randomisation [22].

Human $V_H$ or camelid $V_H$ domains produced by phage or alternative display technology lack the advantage of improved characteristics as a result of somatic mutations and the additional diversity provided by D and J gene segment recombination in the CDR3 region of the normal antibody binding site. Some camelid $V_{H(VHH)}$ domains, whilst showing benefits in solubility relative to human $V_H$, may prove antigenic in man and, moreover, suffer the disadvantage that camelid $V_H$ must be generated by immunisation of camelids or by phage display technology.

Phage-derived human $V_H$ regions are laborious to use since they require many rounds of panning and subsequent mutagenesis in order to achieve high affinity binding characteristics. Camelid $V_{HH}$ domains require the same laborious procedure when isolated from phage or similar display libraries or require the immunization of large animals (llama or camels which also make classical antibodies) not amenable to classic hybridoma technology. Moreover, camelid binding domains may prove antigenic and require humanization.

The production of heavy chain-only antibodies in transgenic non-human mammals (see WO02/085945 and WO02/085944).) as a result of antigen challenge overcomes many of these problems.

However, there remains a need in the art to maximise heavy chain-only antibody diversity and B-cell response in vivo and, in particular, to generate a functional repertoire of class specific human heavy chain-only antibodies and functional $V_H$ heavy chain-only binding domains which retain maximum antigen-binding potential for use in diverse clinical, industrial and research applications.

THE INVENTION

The present inventors have surprisingly overcome the limitations of the prior art and shown that the repertoire of antibody response can be greatly increased by increasing the number of heavy chain-only loci present in a transgenic non-human mammal used to produce class-specific, heavy chain-only antibodies.

The invention relies on the discovery that, where a transgenic non-human mammal possesses multiple heavy chain-only loci, these loci are subject to allelic exclusion. Therefore, only one locus is stochastically chosen and recombined successfully, resulting in the production of a heavy chain-only antibody. Multiple $V_H$ heavy chain loci can, therefore, be used in the same transgenic non-human mammal to maximise the antibody repertoire and diversity obtainable from the mammal. When antigenically challenged, the transgenic non-human mammal "selects" the locus comprising the V gene segment which is best suited to respond to the specific antigen challenge to the exclusion of the remaining loci.

Heavy chain-only antibodies that can be generated by the methods of the invention show high binding affinity as a result of the transgenic non-human mammal being able to "choose" from a range of loci, from which V, D and J gene segment rearrangements and somatic mutations can occur, generally in the absence of an enlarged CDR3 loop. Essentially normal B-cell maturation is observed with high levels of heavy chain-only antibody present in isolated plasma (provided that the $C_H1$ domain has been eliminated from all antibody classes present in the recombinant locus). B-cell maturation and the secretion of assembled dimers (e.g. IgG) or multimers (e.g. IgM) has no dependency on the presence or expression of light chain genes.

Accordingly, in the first aspect of the present invention, there is provided a method for the production of a $V_H$ heavy chain-only antibody in a transgenic non-human mammal comprising the step of providing more than one heterologous $V_H$ heavy chain locus in that mammal, wherein each $V_H$ heavy chain locus comprises one or more V gene segments, one or more D gene segments, one or more J gene segments and a gene segment encoding a heavy chain constant region which, when expressed, does not include a $C_H1$ domain and expressing a $V_H$ heavy chain-only antibody from at least one of said loci.

Preferably each $V_H$ heavy chain locus comprises one or multiple V gene segments, e.g. 1, 2, 3, 4, 5, 6, 1, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 45, 50 or 60 V gene segments, which may be derived from any vertebrate species.

In one embodiment, each locus may comprise only one V gene segment. In one alternative of this embodiment, each V gene segment is different from all other V gene segments. In a second alternative, each V gene segment is identical to all the other V gene segments. In this second alternative, the remaining gene segments in each locus may be the same as or may be different from those in all the other loci.

It is thus envisaged that the non-human mammal may contain multiple copies of a single $V_H$ heavy chain locus. This has the advantage of optimising the chances that a productive re-arrangement in a B cell will take place, thus allowing the production of a useful heavy chain-only antibody.

If the non-human mammal contains a number of different $V_H$ heavy chain loci, this will further optimise the chances of obtaining a heavy chain-only antibody with a desired specificity.

In another embodiment, each locus comprises multiple V gene segments. In this embodiment, the V gene segments in any one locus may all be derived from an organism of the same species, e.g. all V gene segments may be of human origin. Alternatively, the V gene segments in any one locus may be derived from organisms of different species, e.g. some V gene segments from human and others from camelids or from sharks. Preferably, the V gene segments are of human origin.

The term 'V gene segment' encompasses any naturally occurring V gene segment derived from a vertebrate, including camelids and human. The V gene segment must be capable of recombining with a D gene segment, a J gene segment and a gene segment encoding a heavy chain constant (effector) region (which may comprise several exons but excludes a $C_H1$ exon) to generate a $V_H$ heavy chain-only antibody when the nucleic acid is expressed.

A V gene segment also includes within its scope any gene sequence encoding a homologue, derivative or protein fragment which is capable of recombining with a D gene segment, a J gene segment and a gene segment encoding a heavy chain constant region (comprising one or more exons but not a $C_H1$ exon) to generate a heavy chain-only antibody as defined herein. A V gene segment may for example be derived from a T-cell receptor locus or an immunoglobulin light chain locus.

Preferably the multiple heavy chain loci of the invention comprise any number or combination of the 39 functional human V gene segments and engineered variants thereof with improved solubility properties distributed across the multiple loci. These may be on any number of loci, e.g. four loci comprising eight V gene segments plus one locus comprising seven V gene segments; seven loci comprising four V gene segments plus one locus comprising three V gene segments; or thirty-nine loci comprising one V gene segment each.

Human V genes are classified into seven families, $V_H1$ to $V_H7$, and the individual genes within each family numbered. The frequency at which each gene is used is dependent on the varying requirements of the particular immune response. For example, the genes of family $V_H3$ may be preferentially used in comparison to those of family $V_H5$ when responding to bacterial antigens. Therefore, in a further preferred embodiment of the invention, groups of V gene segments which have been shown to be useful for generating an antibody response against specific antigens are grouped into separate lines of transgenic non-human mammals. The V gene segments may be grouped according to family or they may be grouped according to individual function. For example, if the V genes of family $V_H3$ are shown to be useful for generating an immune response against bacterial antigens, then these may be used to generate a transgenic non-human mammal which is particularly useful for generating heavy chain-only antibodies against bacterial antigens. Alternatively, if it is shown that several individual genes from families $V_H3$ and $V_H5$ are useful for generating an immune response against bacterial antigens, then these may be grouped together and used to generate a transgenic non-human mammal which is particularly useful for generating heavy chain-only antibodies against bacterial antigens.

In the context of the present invention, the term 'heterologous' means a nucleotide sequence or a locus as herein described which is not endogenous to the mammal in which it is located.

A "$V_H$ heavy chain locus" in the context of the present invention relates to a minimal micro-locus encoding a $V_H$ domain comprising one or more V gene segments, one or more D gene segments and one or more J gene segments, operationally linked to one or more gene segments encoding heavy chain effector regions (each devoid of a $C_H1$ domain).

Preferably, the primary source of antibody repertoire variability is the CDR3 region formed by the selection of V, D and J gene segments and by the V-D and D-J junctions.

The advantage of the present invention is that antibody repertoire and diversity obtained in the rearranged $V_H$ gene sequences can be maximised through the use of multiple $V_H$ heavy chain loci in the same transgenic non-human mammal. Janssens et al., 2006 [15] have shown that a transgenic locus as described above behaves like a normal immunoglobulin locus in terms of rearrangement and allelic exclusion. This opens up the possibility to have multiple loci in the same animal (on different chromosomes) to maximize the number of possible $V_H$ recombinations by exploiting allelic exclusion. Each of the transgenic loci would contain from one to more than forty $V_H$ regions. The process of allelic exclusion which randomly chooses one of the loci to start recombination, followed by the next locus if the first recombination was non-productive, etc. until a productive recombination has been produced from one of the loci, would ensure that actually all the $V_H$ regions present in the combined loci would be part of the overall recombination process.

Janssens et al, [15] have also surprisingly found that where multiple heavy chain loci in the same transgenic non-human mammal are in tandem on the same chromosome then then productive rearrangement and antibody expression can occur from multiple heavy chain loci. In such cases, subsequent hybridoma clones are polyclonal. The skilled person will appreciate that this is another mechanism for increasing antibody diversity. Accordingly in another aspect of the invention there is provided a method as herein described, wherein at least two or more $V_H$ heavy chain locus in the transgenic non-human mammal are present in tandem on the same chromosome, then productive rearrangement and antibody expression can occur from two or more loci simultaneously. Preferably, a number of heavy chain loci will first be introduced separately in a transgenic non-human mammal, generating transgenic non-human mammals with a single heavy chain locus. These animals will then be crossed to generate progeny with multiple heavy chain loci to maximize the number of $V_H$ regions, resulting in maximum diversity. Loci can also be added through a new round of transgenesis. New loci would be injected into eggs derived from non-human mammals already comprising one or more heterologous VH heavy chain locus. Stable integration of new heterologous VH heavy loci would result in an increase in available VH regions and hence diversity. The stable transfection of ES cells derived from non-human transgenic mammals comprising a heterologous VH heavy chain locus, with additional heterologous VH heavy chain loci, provides an alternative route to increase diversity in non-human mammals (eg mice) where ES cell technology can be used for transgenesis by embryo fusion and blastocyst injection.

Preferably, each different heavy chain locus will be present as a single copy in the genome of the transgenic non-human mammal.

Furthermore, the use of multiple V, D and J gene segments provides a further increase in the antibody repertoire and diversity obtainable. Subsequent somatic mutation is achieved whilst using a minimal locus (micro-locus) without the need for the $V_L$ and $L_C$ (light chain) antibody loci.

In the context of the present invention, the terms 'a D gene segment' and 'a J gene segment' include naturally occurring sequences of D and J gene segments. Preferably, the D and J gene segments are derived from the same vertebrate from which the V gene segment is derived. For example, if a V gene segment is derived from a human, then as required solubilised or engineered, the D and J gene segments are preferably also derived from a human, Alternatively the V gene segments maybe derived, for example, from a camelid and the D and J gene segments from human or vice versa.

The terms D gene segment and J gene segment also include within their scope derivatives, homologues and fragments thereof as long as the resultant segment can recombine with the remaining components of a heavy chain antibody locus as herein described to generate a heavy chain-only antibody as herein described. D and J gene segments may be derived from naturally occurring sources or they may be synthesised using methods familiar to those skilled in the art and described herein. The V, D and J gene segments are capable of recombination and preferably undergo somatic mutation. The D and J gene segments are preferably derived from a single vertebrate species. This may be any vertebrate species but is preferably a human.

Preferably, each $V_H$ heavy chain locus comprises from one to forty (2, 3, 4, 5, 6, 7, 8, 9, 10, 12, 14, 16, 18, 20, 30 or 40) or more D gene segments. The D gene segments maybe derived from any vertebrate species but, most preferably, the D gene segments are human D gene segments (normally 25 functional D gene segments).

Preferably, each $V_H$ heavy chain locus comprises from one to twenty (2, 3, 4, 5, 6, 7, 8, 9, 10, 12, 14, 16, 18 or 20) or more J gene segments. The J gene segments maybe derived from any vertebrate species but, most preferably, the J gene segments are human J gene segments (normally 6 (six) J gene segments).

Each $V_H$ heavy chain locus may contain the same D and J gene segments. Alternatively, each $V_H$ heavy chain locus may contain different combinations of D and J gene segments. For example, where each $V_H$ heavy chain locus contains only one V gene segment and this segment is identical in each locus, it is then advantageous to use different combinations of D and J gene segments in each locus to further optimise the chances of obtaining a productive re-arrangement. However, where each $V_H$ heavy chain locus contains one or more different V gene segments, it may be advantageous to use the same combination of D and J gene segments in each locus.

Preferably, the $V_H$ heavy chain locus comprises one or more V gene segments, twenty-five functional human D gene segments and six human J gene segments.

Each gene segment encoding a heavy chain constant region may comprise one or more heavy chain constant region exons of the $C\delta$, $C\gamma_{1-4}$, $C\mu$, $C\epsilon$ or $C\alpha_{1-2}$ class, with the proviso that the heavy chain constant region gene segments do not express a $C_H1$ domain. The heavy chain constant region gene segments are selected depending on the preferred class or mixture of antibody classes required. Optionally, the heterologous heavy chain locus is $C\mu$- and $C\delta$-deficient.

Thus, each $V_H$ heavy chain locus may comprise a gene segment encoding at least one heavy chain constant region providing effector functions in vivo (e.g. IgG, IgM, IgA, IgE or IgD or an isotype thereof) wherein each constant region does not include a $C_H1$ domain. Each locus may contain only one gene segment encoding one particular constant region. This will be advantageous if certain effector functions are required. Alternatively, each locus may comprise more than one gene segment, each encoding a different constant region. This will be advantageous if there is no requirement for particular effector functions as it will allow a variety of classes of heavy chain-only antibody to be produced.

Each locus may contain the same constant region-encoding gene segment(s) or each locus may have different or a different combination of constant region-encoding gene segment(s).

Operationally, a heavy chain constant region is encoded by a naturally occurring or engineered gene segment that is capable of recombining with a V gene segment, a D gene segment and a J gene segment in a B cell.

In each heavy chain-only antibody, the constant region is expressed without a $C_H1$ domain so that generation of heavy chain-only antibody can occur. The $C_H1$ exons may be deleted so that the constant region of the $V_H$ heavy chain-only antibody as described above does not contain a functional $C_H1$ domain.

The inclusion of class-specific heavy chain constant regions when engineering multivalent binding complexes provides the therapeutic benefits of effector function in vivo dependent on the functionality required. Engineering of individual effector regions can also result in the addition or deletion of functionality [23], Thus, the inclusion of IgA constant region functionality would provide improved mucosal function against pathogens [24], whilst the presence of IgG1 constant region functionality provides enhanced serum stability in vivo. The presence of heavy chain $C_H2$ and $C_H3$ constant domains provides the basis for stable dimerisation as seen in natural antibodies and provides recognition sites for post-translational glycosylation. The presence of $C_H2$ and $C_H3$ also allows for secondary antibody recognition when bispecific and multivalent complexes are used as reagents and diagnostics.

For instance, IgM antibodies are known to play an important role in the activation of macrophages and of the complement pathway. Due to the close proximity of its binding sites, IgM has a high avidity for pathogens, including viruses. However, IgM is also known to be difficult for use in rapid immunoassay techniques, whereas IgG antibodies can be readily used in these techniques. For such uses, it would be useful to select for the preferred antibody class, i.e. IgG or IgM.

The expression of all or part of a heterologous heavy chain $C\gamma$ locus devoid of $C_H1$ will produce optionally some or all IgG isotypes, dependent on the IgG1, IgG2, IgG3 and IgG4 isotypes present in the heterologous IgG locus. Alternatively the heavy chains may comprise $C\epsilon$ genes. The resulting IgE molecule might also be used in therapy. Alternatively, selected mixtures of antibodies may be obtained. For example, IgA and IgM may be obtained when the heavy chain constant region comprises a $C\alpha$ and a $C\mu$ gene.

Preferably, the heavy chain constant region is of human origin, in particular when the heavy chain-only antibody is to be used for therapeutic applications in humans. Where the heavy chain-only antibodies are to be used for veterinary purposes, the heavy chain constant region is preferably derived from the target organism, vertebrate or mammal in or on which veterinary therapy is to be performed.

When expressed, each heavy chain constant region lacks a $C_H1$ domain. Preferably, the $C_H1$ exon is deleted. Optionally, $C\mu$ and $C\delta$ constant regions may be mutated, deleted or substituted. The presence, for example, of IgM with a functional $C_H1$ domain inhibits B-cell maturation, and consequently limits the productive expression of heavy chain-only IgG (devoid of $C_H1$) within the same locus.

A 'heavy chain constant region exon' ('$C_H$ exon') as herein defined includes the sequences of naturally occurring vertebrate, but especially mammalian, $C_H$ exons. This varies in a class specific manner. For example, IgG and IgA are naturally devoid of a $C_H4$ domain. The term '$C_H$ exon' also includes within its scope derivatives, homologues and fragments thereof in so far as the $C_H$ exon is able to form a functional heavy chain-only antibody as herein defined when it is a component of a heavy chain constant region.

Optionally, when present, the $C_H4$ or other functional domains maybe engineered or deleted within the transgene provided such a process does not inhibit the intracellular secretory process, B-cell maturation or the binding activity of the resultant antibody. Heavy chain effector molecules may be engineered to be free of functional domains, for example the carboxy-terminal $C_H4$ domains, provided that engineering does not affect secretory mechanisms preventing cell surface assembly and consequently B-cell maturation. Additional features maybe engineered into the locus, for example to improve glycosylation or add function.

Accordingly, the heterologous heavy chain locus is designed to produce preferred classes or mixtures of heavy chain-only antibodies depending on the antibody class(es) required, with essentially normal B-cell maturation. The utilisation of camelid V, D and J gene segments and camelid effector regions will produce camelid antibodies with features peculiar to camelid antibodies, such as enlarged CDR3 loops. The use of human V, D and J gene segments will produce human heavy chain-only antibodies lacking the enlarged CDR3 loop.

A "$V_H$ domain" in the context of the present invention refers to an expression product of a V gene segment when recombined with a D gene segment and a J gene segment as defined above. Preferably, the $V_H$ domain has improved ability to bind antigen as a result of VDJ recombination and somatic mutation. There is no dependency on the presence or absence of the enlarged CDR3 loop peculiar to the camelid species. The $V_H$ domain is able to bind antigen as a monomer. Any likelihood of combining with a $V_L$ domain when expressed as part of a soluble heavy chain-only antibody complex has been eliminated by removal of the $C_H1$ exon (see [25]).

The $V_H$ domain alone can also be engineered with diverse protein domains to produce fusion proteins for targeted therapeutic and diagnostic purposes, for example with toxins, enzymes and imaging agents.

The $V_H$ domain coding sequences may be derived from a naturally occurring source or they may be synthesised using methods familiar to those skilled in the art.

The properties of the $V_H$ domain may be altered or improved by selecting or engineering V, D and/or J gene segments which encode sequences with the required characteristics. As indicated above, some of the 39 functional human $V_H$ regions may not be suitable for the production of heavy chain-only antibodies. Several studies have been carried out in the prior art in an attempt to improve various antibody characteristics [2629]. With regard to specific $V_H$ region characteristics, Dolk et al., [30] used phage display techniques to generate heavy chain-only antibodies showing improved stability in the harsh conditions associated with anti-dandruff shampoo.

The transgenic non-human mammal is preferably a rodent such as a rabbit, guinea pig, rat or mouse. Mice are especially preferred. Alternative mammals such as goats, sheep, cats, dogs or other animals may also be employed. Preferably, the mammal is a mouse. Preferably transgenic non-human animals are generated using established oocyte injection technology alone. Where established, ES cell technology or cloning may also be used.

Advantageously, antibody heavy and optionally light chain loci endogenous to the mammal are deleted or silenced when a heavy chain-only antibody is expressed according to the methods of the invention.

The methods of generating heavy chain-only antibodies as described in the above aspects of the invention may be of particular use in the generation of antibodies for human therapeutic use, as often the administration of antibodies to a species of vertebrate which is of different origin from the source of the antibodies results in the onset of an immune response against those administered antibodies. The antibodies produced according to the invention have the advantage over those of the prior art in that they are of substantially a single or known class and preferably of human origin. Antibodies are of high affinity resulting from a combination of VDJ recombination and affinity maturation in vivo. Accordingly, a further aspect of the invention provides a transgenic non-human mammal comprising more than one heterologous $V_H$ heavy chain locus as defined above. Preferably, the transgenic non-human mammal may be engineered to have a reduced capacity to produce antibodies that include light chains.

Antibody-producing cells may be derived from transgenic non-human mammals as defined herein and used, for example, in the preparation of hybridomas for the production of heavy chain-only antibodies as herein defined. In addition or alternatively, nucleic acid sequences may be isolated from these transgenic non-human mammals and used to produce $V_H$ domain heavy chain-only chain antibodies or bi-specific/bi-functional complexes thereof, using recombinant DNA techniques which are familiar to those skilled in the art.

Alternatively or in addition, antigen-specific heavy chain-only antibodies may be generated by immunisation of a transgenic non-human mammal as defined herein. Accordingly, the invention also provides a method for the production of heavy chain-only antibodies by immunising a transgenic non-human mammal as defined above with an antigen. Antibodies and fragments thereof may be may be isolated, characterised and manufactured using well-established methods known to those skilled in the art. These antibodies are of particularly use in the methods described in PCT/GB2005/00292. The invention is now described, by way of example only, in the following detailed description which refers to the following figures.

FIGURES

FIG. 1: Schematic representation of the DNA fragments used to generate the transgenic mice. Two of the llama $V_{HH}$ exons are linked to the human heavy chain diversity (D) and joining (J) gene segments, followed by the Cμ, Cδ, Cγ2 and Cγ3 human constant region genes and human heavy chain Ig 3' LCR. Modifications of human Cγ2 and Cγ3 genes were a complete deletion of the CH1 exon from Cγ2 and Cγ3 genes in constructs MGΔ and GΔ or also from Cμ in construct MAGΔ. The presence of two Lox P sites (in red) in the same direction enables the removal of Cμ and Cδ genes upon Cre mediated recombination. The presence of the Frt site (in green) enables the generation of a single copy transgenic mouse from a multi-copy transgene array by Flp mediated recombination.

FIG. 2A-2D: Panel A: Table of the flow cytometric analysis of the B lymphocytes expressed as the percentage of B220/CD19 positive cells of total cells in the different organs. Panel B: Flow cytometric analysis of B cell populations of wt, μMT, MGΔ/μMT, MΔGΔ/μMT and GΔ/μMT mice in the BM. Lymphoid cells were gated on the basis of forward and side scatter and surface expression of B220 and human IgM or IgG is plotted. Data are displayed as dot plots. For MGΔ μMT mice the B220+ fraction was gated and analyzed for the expression of intracellular (ic) human Ig μ and γ H chains, displayed as histogram overlays (red lines), with background staining of B220+ cells from μMT mice (black lines) as controls. The percentages of positive cells are indicated. Panel C: Expression of the MΔGΔ or GΔ transgene rescues pre-BCR and BCR function. Expression profiles of the indicated markers in total CD 19+ fractions from μMT mice (pro-B cells), in CD19+ surface IgM− fractions (pro-B/pre-B cells) and CD 19+ surface IgM+ fractions (B cells) from wild-type mice, in CD 19+ surface human IgM+ fractions from MΔ-GΔ μMT mice (B cells) and CD19+ surface human IgG+ fractions from GΔ μMT mice (B cells). ic-Ig$_K$=intracellular Ig$_K$ L chain. Flow cytometric data are displayed as histograms. Data shown are representative of 3-8 animals examined within each group. Panel D: Sequence alignment of the PCR products obtained from BM cDNA using YHH1 and VHH2 specific primers in combination with human Cγ2 primer, showing VDJ recombination. Sequences are from GΔ. Sequence GΔIg1 is SEQ ID NO: 17, Sequence GΔIg2 is SEQ ID NO: 18, Sequence GΔIg3 is SEQ ID NO: 19, Sequence GΔIg4 is SEQ ID NO:20, Sequence GΔIg5 is SEQ ID NO:21, Sequence GΔIg6 is SEQ ID NO:22, Sequence GΔIg7 is SEQ ID NO:23, Sequence GΔIg8 is SEQ ID NO:24, Sequence GΔIg9 is SEQ ID NO:25, Sequence GΔIg10 is SEQ ID NO:26. Green shows sequence identity.

FIG. 3A-3F: Panel A-E: DNA FISH of a five copy human GΔ locus. Panel A: Stretched 30 chromatin fiber from lung cells of GΔ line1 transgenic mouse carrying five intact copies (1-5) of the GΔ locus, flanked by half a locus containing the LCR (red) and half a locus carrying VHH to J region (green). Panel B: Stretched chromatin fiber FISH of a hybridoma (G20) derived from GΔ line1 B cells where one copy has rearranged (white arrow). Panel C: Non stretched DNA FISH of hybridoma T1 with the LCR probe (red). Panel D: Same as C with a probe between VHH and D (green). Panel E overlay of panels C and E. Note that T1 has four rearrangements visible as the loss of 4 green signals compared to no loss of red signals. Panel F: Allelic exclusion in GΔ transgenic mice is preserved. Flow cytometric analysis of murine surface or intracellular (ic)μH chain and transgenic human IgG on total BM CD 19+ cell fractions from the indicated mice. Data are displayed as dot plots and the percentages of cells within the indicated quadrants are given. Data shown are representative of four mice examined within each group.

FIG. 4A-4D: Analysis of B cell populations in the spleen of wt, μMT, GΔ, MΔGΔ and MGΔ mice. Data shown are representative of 4-8 mice examined within each group. Panel A: Top, FACS data of spleen cells, stained for mouse IgM, human IgG, human IgM versus B220. Bottom, flow cytometric analysis of B cell populations in the spleen. Lymphoid cells were gated on the basis of forward and side scatter and surface expression of B220 and the indicated Ig (upper part) or the CD21/CD23 profile is displayed as dot plots and the percentages of cells within the indicated gates are given. C-D21$_{low}$CD23$_{low}$: immature B cells; CD21$_+$CD23$_+$: follicular B cells; CD21$_{high}$CD23$_{low}$: marginal zone B cells. Panel B: Histology of the spleen of wt, μMT, GΔ/μMT, MΔGΔ/μMT and MGΔ/μMT mice. Immunohistochemical analysis; 5 μm frozen sections were stained with anti B220 (blue) for B cells and anti-CD 1 lc/N418 (brown) for dendritic cells. Arrows indicate the location of small clusters of B cells in the MGA spleens. Panel C: Sequence alignment of the PGR products obtained from Payer's patches cDNA using YHH1 and VHH2 specific primers in combination with human Cγ2 primer, showing that the transgenic locus undergoes hypermutation in the CDR1 and 2 regions. Sequences are from the transgenic locus GΔ with a CH1 deletion. Germline VHH1 is SEQ ID NO:27, Clone 1 is SEQ ID NO:28, Clone 2 is SEQ ID NO:29, Clone 3 is SEQ ID NO:30, Germline VHH2 is SEQ ID NO:31, Clone 4 is SEQ ID NO:32, Clone 5 is SEQ ID NO:33, Clone 6 is SEQ ID NO:34. Panel D: Top; FACS data of spleen cells, stained with anti-CD 19 and anti-B220. Bottom left: Schematic representation of Flp recombination in vivo by breeding to FlpeR transgenic line and FACS data on spleen cells of the single copy recombinant derived from the five copy GΔ line 1. Bottom right: Schematic representation of Cre recombination in vivo by breeding MGΔ lines to a CAGCre transgenic line and supporting FACS scan data on spleen cells of the recombinant, showing B cell rescue as seen in the directly generated original GΔ lines.

Figure 5A:
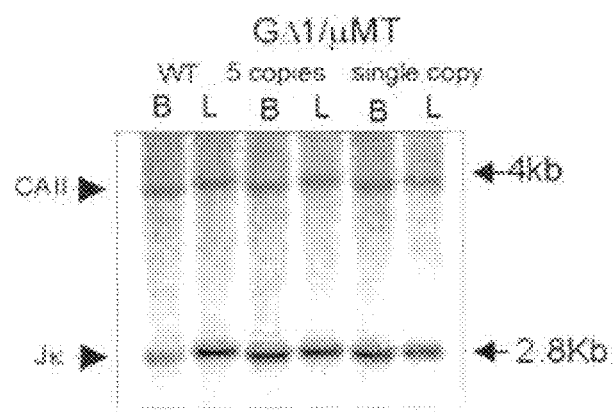
Figure 5B:
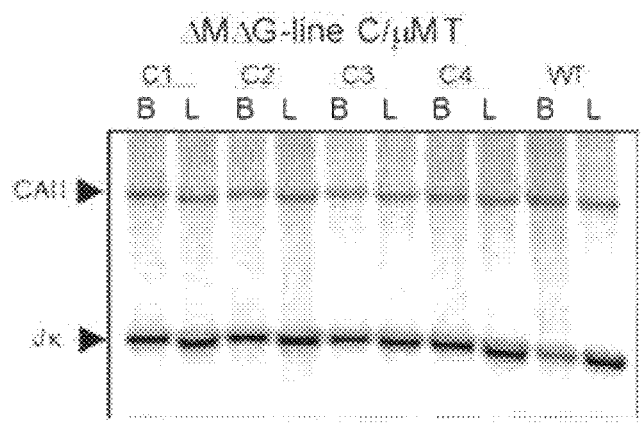

FIG. 5A-5B: Southern blots showing the absence of the κ light chain rearrangement in GΔ/μMT (panel A) and MΔGΔ/γMT (panel B) transgenic lines. Liver DNA (L) and B cell DNA (B) from a wt mouse and two GΔ or four MΔGΔ transgenic mice was Hind III digested and probed with the $^{32}$P radiolabeled J$_K$ probe and the carbonic anhydrase II (CAII) probe. The CAII probe, which hybridizes to a 4 kb band was used as a loading control. Liver DNA was run to show the $_K$ germline configuration (2.8 Kb band). Only the wt B cells show $_K$ locus rearrangement measured as a decrease in intensity of the 2.8 kb fragment (30% of signal left when compared to liver).

FIG. 6A-6G: Prot G or concavalin purified serum samples of 6 different GΔ lines (A, B), 4 different MΔGΔ lines (C) and 2 different MGΔ lines (E-G), in the μMT background run under non-reducing (A) and reducing conditions (B-G). The size of the transgenic human IgG (panels B, F) and IgM (panel C, D) is consistent with the CH1 deletion and the absence of light chains. Mouse$_K$ light chains were normal size (G). Human serum was used as a positive control. Panel D: Superose 6 size fractionation of MΔGΔ serum aftermixing in a human IgM control under non-reducing conditions. Each fraction was analysed by gel electrophoresis under reducing conditions. Fractions collected from the Superose 6 column are from left (high MW) to right (low MW). The controls are human serum alone (first lane left) and mouse serum before mixing in the human IgM control serum (lane MΔGΔ serum). Size markers are indicated.

FIG. 7A-7E: Panel A: Sequences of monoclonal antibody cDNAs specific for tetanus toxoid; HSP70, rtTA and human TNFα. The top sequence is the germline VHH2 sequence, identified as SEQ ID NO:35. The α-B. Pertusis sequences 1-5 are, in order, SEQ ID NO:36, SEQ ID NO:37, SEQ ID NO:38, SEQ ID NO:39, and SEQ ID NO:40. The α-Tetanus sequences 1-4 are, in order, SEQ ID NO:41, SEQ ID NO:42, SEQ ID NO:43, and SEQ ID NO:44. The A-hsp70 sequence is SEQ ID NO:45. The α-rTTA sequences are, in order, top to bottom, SEQ ID NO:46, SEQ ID NO:47, and SEQ ID NO:48. The α-TNF sequences are, in order, top to bottom, SEQ ID NO:49, SEQ ID NO:50, and SEQ ID NO:51. The CDR 1, 2 and 3 and hinge regions are indicated above the sequence. Different isotypes and classes are indicated by different colors on the right. The J regions that are used are indicated on the right. Panel B: Examples of western blots using the different heavy chain-only antibodies (hybridomas, sera and sdAb). Left panel anti-rtTA serum and hybridoma medium, diluted 1/100 and 1/250 respectively. Middle panel, anti DKTP serum from wt and GΔ mice diluted 1/200 and 1/100 respectively. Right panel, anti B.

Pertussis sdAb against vaccine containing *B. Pertussis* antigen (DKTP) or lacking it (DTP, since we were unable to purchase purified *B. Pertussis* antigen). Panels C and D: Immunostaining of one of Tet- on cell lines additionally transfected with a marker plasmid that responds to the presence of rtTA by expressing a marker protein in the cytoplasm$_{51}$. Panel C shows nuclei expressing rtTA (green). Panel D shows doxycycline induced expression of the marker protein in the cytoplasm (red) in response to rtTA and nuclear staining of the cells with DAPI (blue). Panel E: Example of BiaCore analysis of the anti rtTA antibody. Affinity is indicated.

Figure 8A:
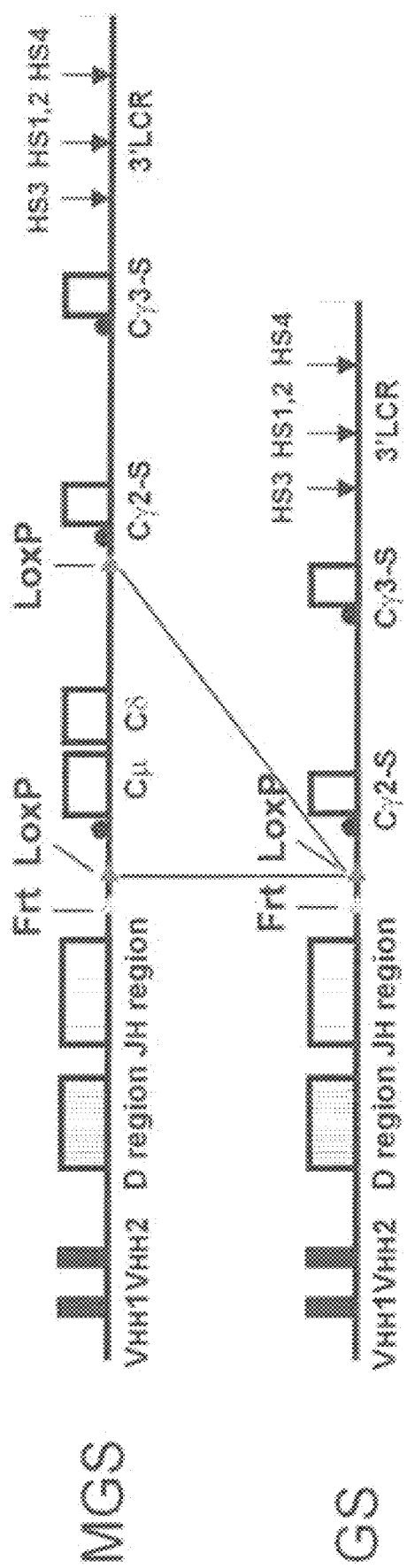
Figure 8B:
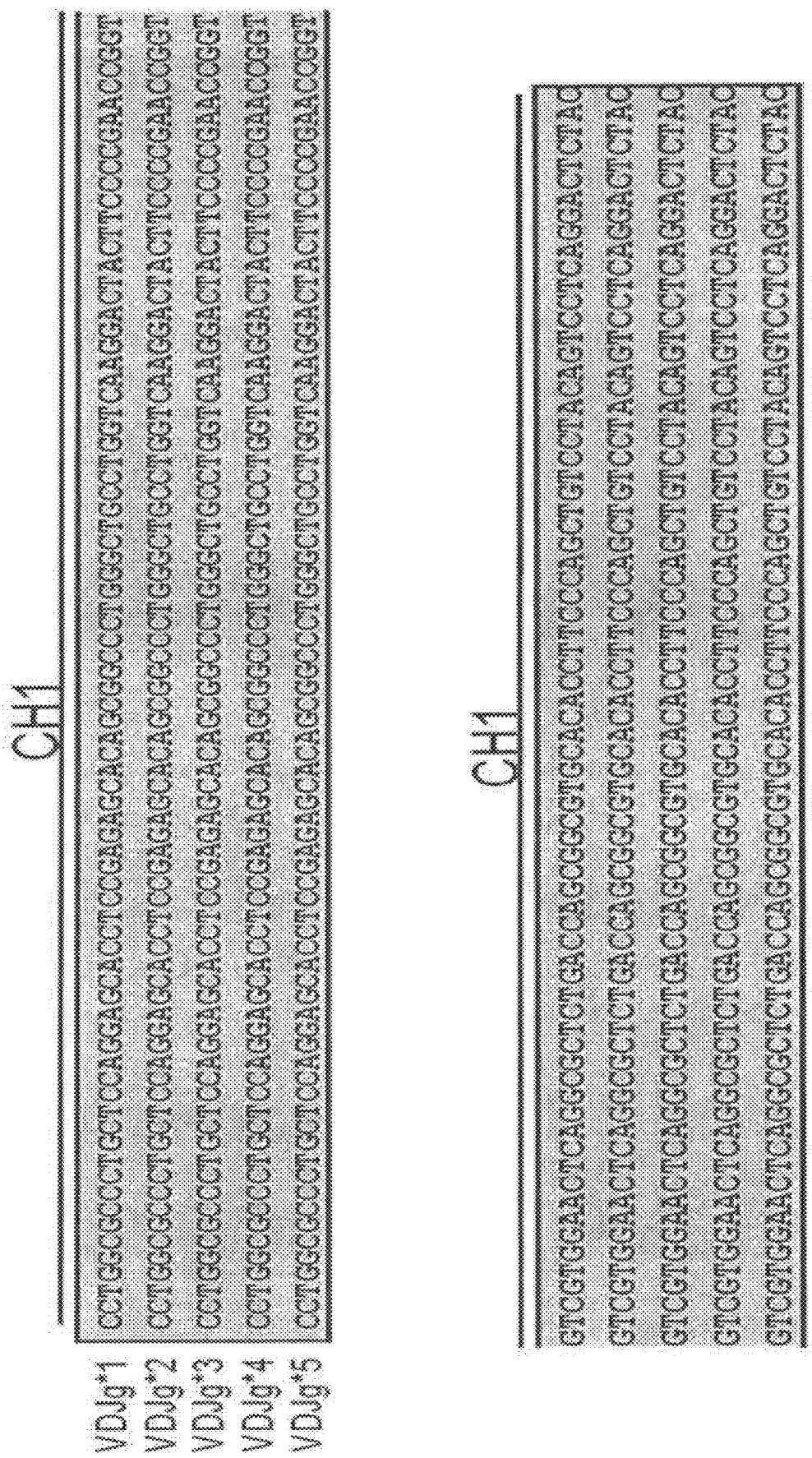

FIG. 8A-8B: Panel A: Schematic drawing of the Ig loci with camelid like splice mutations. The two human IgG constant regions (Cγ2 and Cγ3) were first mutated by altering the splice $G_{+1}$ to $A_{+1}$, thought to result in CH1 exon skipping in camelid IgG HCAb$_{SS}$ depicted as Gγ2-S and Gγ3-S. The locus contained two llama VHH regions all of the human D and JH regions and human Cμ, Cδ and Cγ2 and Cγ3 and the LCR (see also main text). These loci were introduced into μMT transgenic mice and analysed for the expression of the human loci. Panel B: Sequencing of bone marrow (BM) human IgG cDNA from the GS mice showed that both VHHs recombined with different human D and J segments and were transcribed with the Cγ2 constant region. However, the CH1 exon was still present, save the last 16 bp, which were spliced out and is identified as SEQ ID NO:57. While in progress, the same cryptic splice site in the CH1 exon was reported in a leukemia patient due to an A to G transition in position 4 of intron 1 [31]. None of the MGS or GS lines rescued B cell development (not shown) in μMT mice. Although the mouse B cell transcriptional/translational machinery can process rearranged dromedary VHH-γ2a [34, 60] our data show that in addition to the G to A mutation, other features are important for CH1 exon skipping. Sequence VDJg*1 is SEQ ID NO:52, VDJg*2 is SEQ ID NO:53, VDJg*3 is SEQ ID NO:54, VDJg*4 is SEQ ID NO:55, VDJg*5 is SEQ ID NO:56.

FIG. 9: Schematic representation of the cloning of human VH regions onto the various loci as described in Examples 3 and 4

Figure 10:
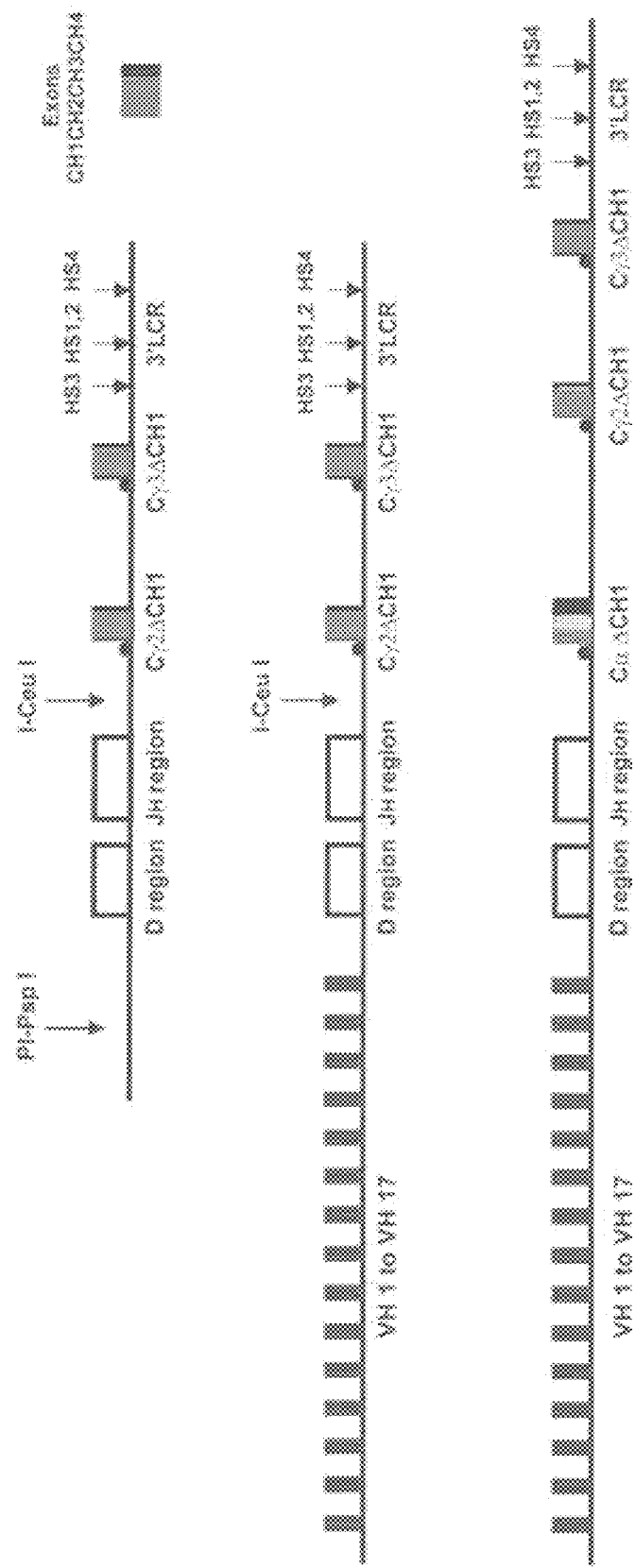
Figure 11:
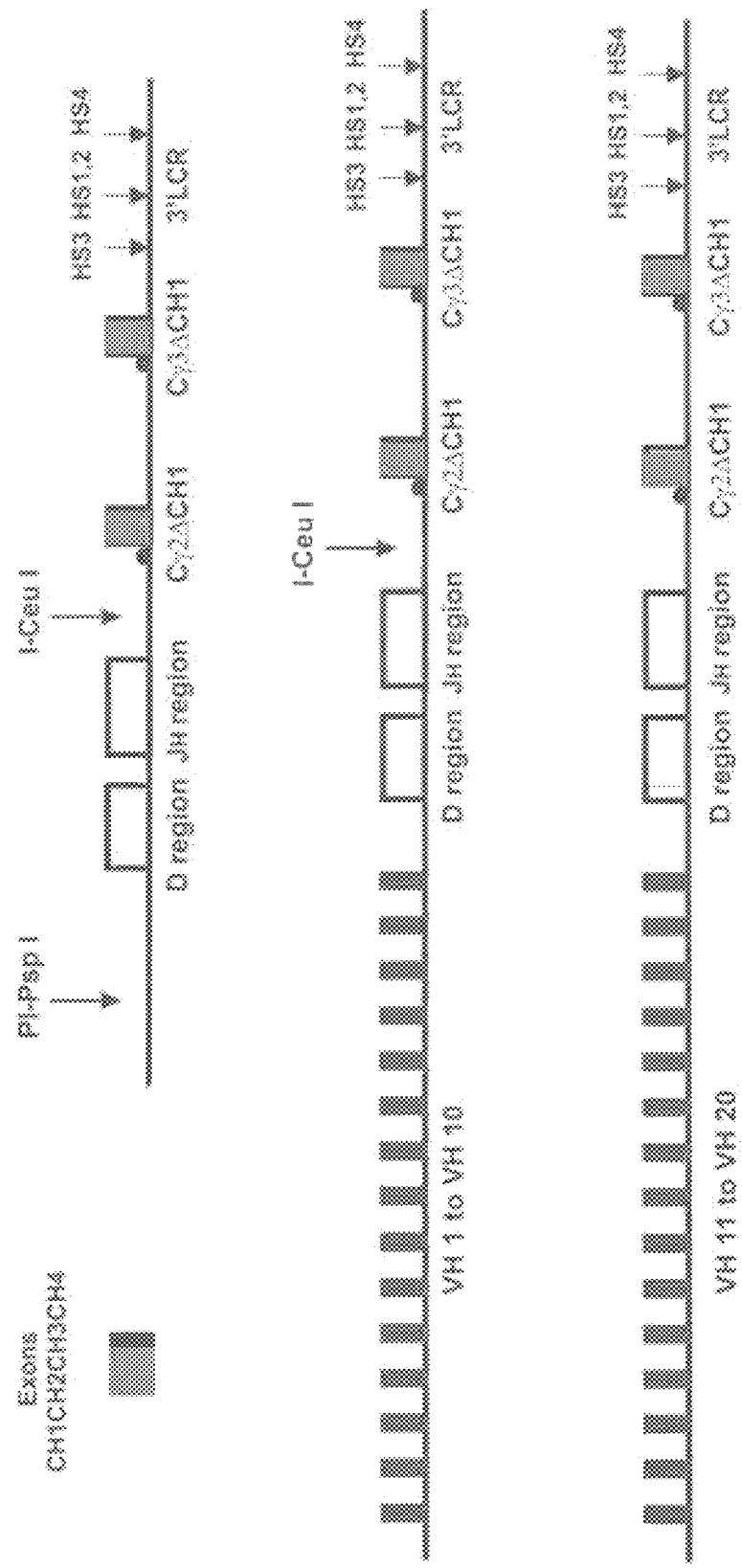

FIGS. 10 and 11: Examples of heavy chain loci containing multiple $V_H$ gene segments, the entire D region, the entire JH region, the Oγ2, Cγ3 and Cx regions and the 3' LCR.

Figure 12:
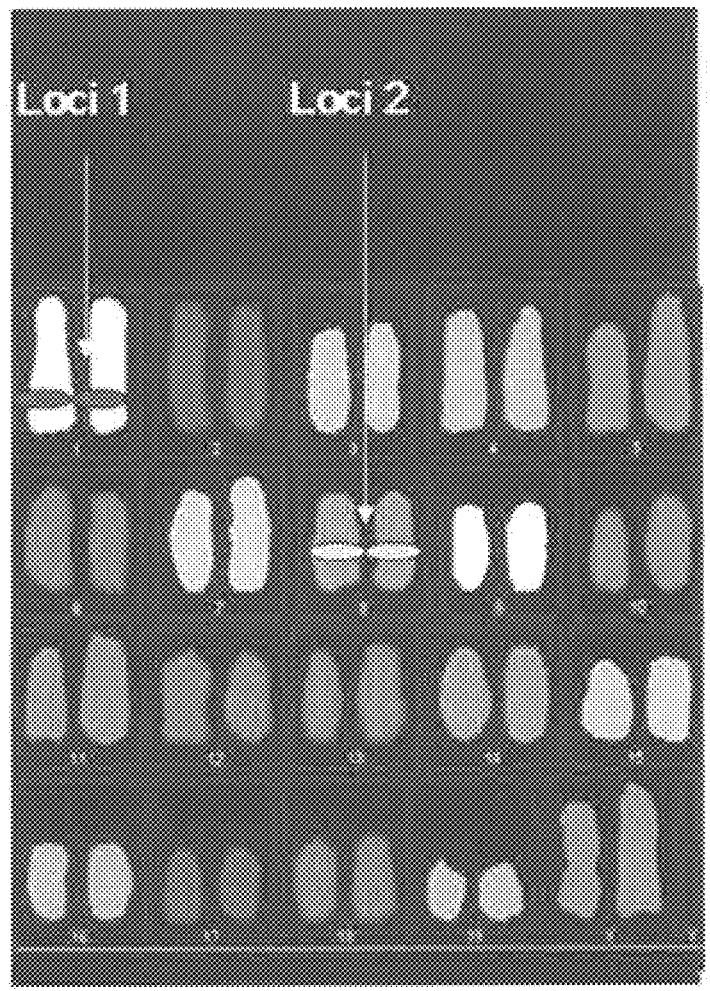

FIG. 12: Shows a karyogram with one locus integrated on chromosome 1 and one locus on chromosome 8.

EXAMPLES

Example 1—A Heavy Chain-Only Antibody Locus is Fully Functional in Mice and Sensitive to Allelic Exclusion As discussed above, Janssens et al. [15] have developed methods for the derivation of heavy chain-only antibodies in transgenic mice. For further details of the methods and experiments described herein, the skilled person should refer to Janssens et al. [15], which is incorporated herein by reference.[1]
Methods
Constructs
A genomic cosmid library was made from peripheral blood cells of *Lama Glama* using standard methods. Two different germline VHHs were chosen based on their sequence, an open reading frame without stop codon and the presence of hydrophilic amino acid codons at positions 42, 50 and 52 according to Lefranc numbering [32] and one with and one without a hydrophilic amino acid at position 49. One is identical to IGHV1S1 (acc.num. AF305944) and the other has 94% identity with IGHV1S3 (acc. num.AF305946). Two clones were selected from the human genomic Pac library RPCI-11 (BACPAC Recource Center, USA): clone 1065 N8 containing human heavy chain D and J regions, C μ and Cδ and clone 1115 N15 containing the C γ3 gene. Bac clone 11771 from a different human genomic library (Incyte Genomics, CA, USA) was used as a source of Cγ2 gene and the Ig heavy chain LCR [33]. Using standard techniques, the Cγ3 and Cγ2 genes were subcloned separately into pFastBac (Invitrogen). The single point mutation (G to A) [34] or a complete deletion of CH1 exon was achieved by homologous recombination [35]. Similarly frt and lox P sites were introduced in front of the Cμ switch region and a second lox P site was placed in front of the Cγ2 switch region, resulting in MGS or MGΔ.

In order to obtain the GS or GΔ constructs, the MGS or MGΔ vector (FIG. 1), containing two llama VHH genes, followed by human D and J heavy chain regions, Cμ, Cδ and the modified human Cγ2 and Cγ3 genes and 3' LCR, was transformed into 16 294 Cre *E. coli* strain$_{44}$ yielding the GS or GΔ locus through cre mediated recombination (FIG. 1). MΔGΔ was obtained from MGΔ by deletion of the CμCH1 region through homologous recombination.
Generation of Transgenic Mice, Breeding and Genotyping The 220 Kb MGS or MGΔ or MΔGΔ fragments, 150 Kb GS or GΔ fragments (FIG. 1) were purified from vector sequences and injected into pronuclei of fertilized FVB X B16/μMT-/-eggs at a concentration of 2 ng/μl. Transgenic loci were checked for integrity and number of copies by Southern blot analysis of tail DNA using 5' and 3' end probes. Transgenic μMT+/- founders were bred as lines in the μMT-/-background. Genotyping was done by PCR (30 cycles with denaturation at 94° C. for 45 s, annealing at 60° C. for 30 s and extension at 72° C. for 1 min 40 s) using the following primers: Asp5'IgM fw: 5'-GCGGGTAC-CGAATGGTGGCAGGGATGGCTC-3' (SEQ ID NO: 1) in combination with Asp 3'IgG2 rv: 5'-CGCGGTACCCTGCG-GTGTGGGACAGAGCTG-3'(SEQ ID NO:2) for HLL-MD or with Asp3'IgM rv: 5'-CGCGGTACCACGGCCACGGC-CACGCTGCTCGATTC-3'(SEQ ID NO:3) for MGS and MIGMEMBINTRON1: fw: 5'-CCAGTCAATAC-TACTCGCTAAGATTC-3'(SEQ ID NO:4) in combination with MIGMEMBEXON1 rv: 5'-CAGTGGTCCACA-GTTTCTCAAAGC-3' (SEQ ID NO:5) for the μMT genotype.
RT-PCR Total RNA was isolated using Ultraspec RNA isolation system (Biotecx Laboratories, Houston). cDNA was synthesized using reverse transcriptase (Superscript II, Life technology) and an oligo (dT) primer. PGR was performed using following primers: LVHHfw: 5'-AGACTCTCCTGTGCA-GCCTCTGG-3'(SEQ ID NO:6) in combination with HINGEIgG2rv: 5'CACTCGACACAACATTTGCGCTC-3' (SEQ ID NO:7) or hIgMCH2rv: CACTTTGGGAGGCA-GCTCAGC-3' (SEQ ID NO: 8) Amplification was for 30 cycles with denaturation at 94° C. for 30 s, annealing at 60° C. for 30 s and extension at 72° C. for 1 min. PGR products were cloned into pGEM T easy vector (Promega) and sequenced using T7 or SP6 primers.
Flow Cytometric Analyses:

Single cell suspensions were prepared from lymphoid organs in PBS, as described previously$_{45}$. Approximately $1\times10^6$ cells were incubated with antibodies in PBS/0.5% bovine serum albumin (BSA) in 96 well plates for 30 min at 4° C. Cells were washed twice in PBS/0.5% BSA. For each sample, $3\times10^4$ events were scored using a FACScan analyzer (Becton Dickinson, Sunnyvale, Calif.). FACS data were analyzed using CellQuest version 1.0 computer software. Four-color analysis was done on a Becton Dickinson FACS Calibur. Most antibodies used have been described [36]; FITC conjugated anti-human IgG and anti human IgM were purchased from Sigma (Zwijndrecht, NL).

Ig Gene Rearrangement Analysis

Single cell suspensions were made from spleens and livers of wt mice MΔGΔ and GΔ transgenic mice. B cells were positively selected using MACS CD45 (B220) Micro-Beads (Miltenyi Biotec, Germany) on an Automacs separator according to the manufacturer's instructions to ~90% purity [37]. Genomic DNA was Hind III digested and blotted onto Hybond nylon filters. The filter was hybridized with a $_{32}$P radiolabeled $J_K$ probe (obtained by PGR amplification from genomic DNA over $J_K1$ and $J_K5$ regions) and $^{32}$P radiolabeled carbonic anhydrase II (CAII) probe. Liver DNA was run to show the signals of the K germline configuration (2.8 Kb band). The CAII probe, which hybridizes to a 4 kb band was used as a loading control. Filters were scanned on a Tyfoon 9200 (Amerscham Biosciences). The intensity of germ line $J_K$ band was quantified using Image Quant 5.2 software, normalized to that of the loading control, and expressed as a percentage of the control liver DNA (which is 100%). PGR primers used on genomic DNA from hybridomas for amplification of different rearrangement events were as follows:

```
IGIIJ1R:
                                    (SEQ ID NO: 9)
5'-CCAGTGCTGGAAGTATTCAGC-3',

IGHJ2R:
                                    (SEQ ID NO: 10)
5'-CAGAGATCGAAGTACCAGTAG-3',,

IGHJ3R:
                                    (SEQ ID NO: 11)
5'-GGCCCCAGAYATCAAAAGCAT-3',,

IGHJ4R:
                                    (SEQ ID NO: 12)
5'-GGCCCCAGTAGTCAAAGTAGT-3',,

IGHJ5R:
                                    (SEQ ID NO: 13)
5'-CCCAGGRGTCGAACCAGTTGT-3',,

IGHJ6R:
                                    (SEQ ID NO: 14)
5-CCAGAACGTCCATRYMGTAGTA-3',
```

DNA FISH Analysis

Preparation of target DNA: Monoclonal hybridoma cells were cultured in DMEM/10% FCS and embedded in agarose as described by Heiskanen [38]. Lungs from a mouse of the GΔ transgenic line 1 were collected and a single cell suspension was made. The embedded cells were treated with proteinase K and Rnase H. Mechanically extended DNA was prepared on poly-L-lysine slides (Sigma) using a microwave oven and the edge of another slide.

Probes: To detect rearranged and non-rearranged copies of the GΔ transgene, DNA fragments were purified. A 2.3 kB SpeI and a 3.6 kB SpeI-BssHII fragment for hybridizing the region between VHH and D, and a 5.9 kB BamHI-SpeI fragment for hybridizing the low copy Bluescript plasmid containing the IgH 3'LCR (16 kB) for LCR detection. The probes were labeled by nick-translation with biotin-11-dUTP (Roche) or digoxigenin-11-dUTP (Roche). Prior to pipetting the probes on the slides, they are denatured by for 5 minutes at 90° C., 5 minutes on ice, and 45 minutes at 37° C. In situ hybridization: The hybridization mixture contained 50% formamide, 2×SSC, salmon sperm DNA (200 ng/μl), 5×Denhardt's, 1 mM EDTA, and 50 mM sodium phosphate, pH 7.0. Hybridization of the probes is done by pipetting 25 μl mixture onto the slides, and covering with a 24×32-mm cover slip. To denature the probes and target sequences the slides were put on an 80° C. heating plate for 2 minutes. The probes hybridize overnight at 37° C. in a humidified chamber (humidifier is 50% formamide, 2×SSC). Post hybridization washes were performed as described [39].

Immunological detection of the hapten-labeled probes: The digoxigenin probe was detected with sheep-anti-digoxigenin (1:500, Sigma), fluorescein-conjugated rabbit-antisheep (1:500, Sigma), and fluorescein-conjugated goat-anti-rabbit (1:500, Sigma). The biotin probe was detected with Texas Red-conjugated avidin (1:500, Sigma) and biotinconjugated goat-anti-avidin (1:500, Boehringer). This step was repeated twice. All incubations and washes were performed as described$_{48}$. After staining the slides were dehydrated in a graded series of ethanol (70, 90, and 100%) 5 minutes each step at room temperature. Cells or DNA was embedded in 25 μl anti-fading embedding medium Vectashield (Vector Laboratories). Visualization was done with a Leica DMRBE fluorescent microscope using a 100× objective.

Immunization and Hybridoma Production 8 weeks old mice were immunized with 5-20 μg of antigen with Specol adjuvant (IDDLO, Lelystadt, NL) or with preformulated DKTP vaccine s.c. on days 0, 14, 28, 42 and i.p. on day 50. Blood was taken on day 0, 14 and 45. Spleen cells were fused with Sp2-0-Ag14 myeloma cells line (gift from R. Haperen) on day 56 using a ClonalCellT-MHY kit (StemCell Technologies, Canada) according to the manufacturer's instructions. DKTP vaccine was obtained from the Netherlands Vaccine Institute (Bilthoven, NL).

sdAB Library Construction and Screening

Total RNA was isolated from spleens of DKTP immunized single copy GΔ and TNF α immunized MΔGΔ mice using an Ultraspec RNA isolation system (Biotecx Laboratories Inc, Houston, Tex., USA). cDNA was made using oligo (dT) primer. DNA fragments encoding VHHDJ fragments were amplified by PGR using specific primers: vhl back Sfi I primer [40-42] in combination with hIgG2hingrev primer (5'-A ATCTGGGCAGCGGCCGCCTCG ACA-CAACATTTGCGCTC-3' (SEQ ID NO: 15)) or CH2huIgMrev primer (5'-TGGGACGAAGACGGC-CGCTTTGGGAGGCAGCTCGGCAAT-3' (SEQ ID NO: 16)). The amplified VHHDJs (~400 bp) were Sfi I/Not I digested, gel purified and cloned into Sfi I/NotI digested phagemid pHEN derived vector. Transformation into TG1 electro-competent cells (Stratagene La Jolla, USA) yielded in a human single domain antibody library. Two rounds of selection were performed using panning on DKTP vaccine antigens adsorbed onto plastic (immunotubes coated with undiluted vaccine) or purified human TNFα (Biosource International, USA).

Immunocytochemistry and Western Blots

Cells of the tet-on cell line transfected with a marker plasmid that responds to the presence of rtTA were grown on a slide. After a 24 hrs doxycycline induction, the cells were fixed in 4% paraformaldehyde/PBS and permeabilized in 0.5% Triton-X-100/PBS. The HCAb against rtTA was used in a 1:50 dilution, followed by goat anti human-IgG FITC staining (Sigma 1:500 dilution). The marker protein was detected as described previously$_{51}$. Western blots were standard using goat anti human IgG-HRP (Sigma, 1/2500 dilution), human IgM-HRP (Sigma, 1/2500 dilution).

Superose 6 Gel Filtration.

Size fractionation of MΔGΔ mouse serum and human control serum was carried out using an AKTA FPLC apparatus (Amersham Biosciences, Piscataway N.J.) with a Superose 6 10/30 column equilibrated in 200 mM KCl/20 mM HEPES-KOH pH 7.9/1 mM $MgCl_2$/0.5 mM EGTA/ 20% glycerol. Using a flow of 100 μl/min, fractions of 500 μl were collected, precipitated with 100% trichloroacetic acid and analyzed by SDS-PAGE (under reducing conditions) followed by Western immunoblotting.

BIAcore Measurements.

Experiments were carried out on a BIAcore 3000 surface plasmon resonance biosensor (Biacore AB, Uppsala, Sweden). Purified proteins were immobilized on a CM5 sensor chip to a level of 3000 resonance units (RU, arbitrary binding response units) with the standard NHS-EDC kit supplied by the manufacturer. Antibodies were passed over the immobilized antigens at a constant flow rate of 40 micrograms per ml in 10 mM Hepes, pH 7.4, 150 mM NaCl, 2 mM EDTA, 0.005% Tween 20. The response at equilibrium was recorded and curve fitting was used to obtain the equilibrium dissociation constants, using the manufacturer's BIA evaluation software.

Results

The Camelid Like CH1 Splice Mutation is Insufficient for Exon Skipping in the Human Heavy Chain Locus.

Figure 8B:
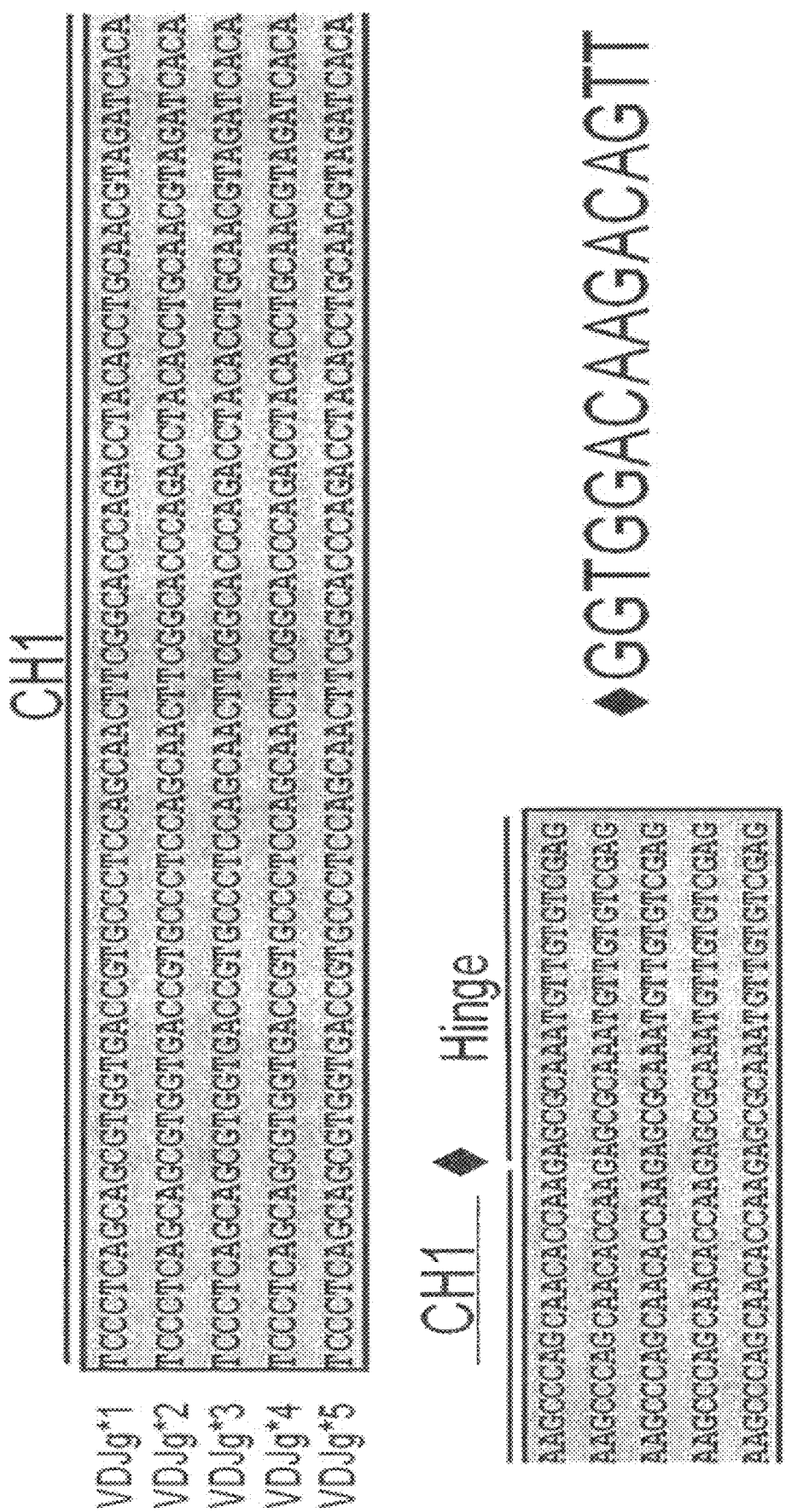

It is not known whether the generation of HCAb (IgG2 and IgG3) in camelids involves an $IgM_+$ intermediate step. We therefore first generated two hybrid human loci, one locus (MGS) with a human Cμ, Cδ, Cγ2 and Cγ3 constant regions and one with only human Cγ2 and Cγ3 (FIG. 1) in a μMT background [43], The Cγ regions were first mutagenised to contain the camelid CH1 splice mutations. MGS was generated because it has been shown that μMT animals, which almost completely lack B cells due to a transmembrane domain deletion of the μ chain gene [43], do have a small B cell population, producing functional IgG, IgA and IgE in the absence of membrane IgM [44-46], suggesting that (some) B cells develop without IgM surface expression. Instead of mutating human VH domains for improved VH solubility [47,48] two YHHs of llama origin were introduced. Camelid VHH regions contain a number of characteristic amino acids at positions 42, 49, 50 and 52 [49], The first, VHH1, contained all of these VHH hallmark amino acids, but to test the importance of solubility in this proof of principle experiment, the other, VHH2, lacked one of these critical "solubility" amino acids, a Gln (Q) instead of a Glu (E) at position 49. We chose 49 rather than position 50 (Arg, R), as it is thought to be additionally important for variable light chain (VL) pairing$_{21}$. The locus also contained all of the 5 human heavy chain D and J regions and the Locus control region (LCR) at the 3' end of the locus (FIG. 8). Surprisingly, the splice mutation did not lead to correct CH1 exon skipping in transgenic mice and lack of human Ig expression (FIG. 8).

Analysis of Transgenic Mice Containing Human Loci Lacking a CH1 Region

To overcome the CH1 splicing problem, we generated 3 new constructs (FIG. 1), all containing Cγ2 and Cγ3 from which CH1 was deleted, one with Cμ and Cδ (MGΔ), one without Cμ and Cδ (GΔ) and one with a Cμ segment from which CH1 was deleted (MΔGΔ). Three MGΔ, six GΔ and four MΔGΔ transgenic mouse lines with different copy numbers (1-5 copies) were obtained in a μMT background. B cell development was analysed in bone marrow (BM) and spleen. Mice with different copy numbers gave the same results.

Expression of GΔ and MΔGΔ Rescues B Cell Development in μMT Mice

Figure 2B:
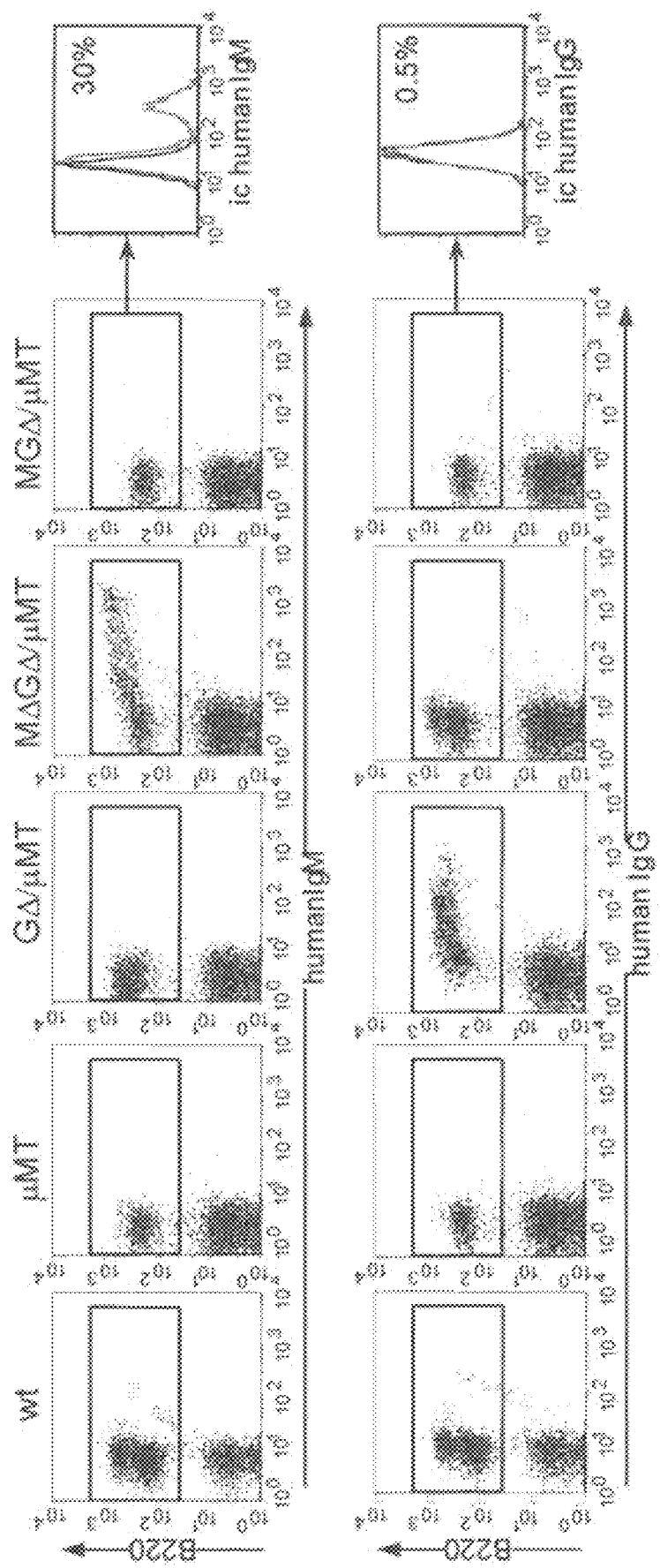

MGΔ mice were unable to rescue B cell development in a μMT background, whereas the GΔ and MΔGΔ constructs efficiently rescued B cell development. The rescue of B220/ CD19 positive cells was between 30-100% in the different lymphoid compartments independent of copy number (FIG. 2A). This is confirmed by flow cytometry of BM using B220 versus human IgM or human IgG staining (FIG. 2B). The MΔGΔ mice contain human IgM producing cells in the BM absent in wildtype or μMT mice. Appropriately these cells have not undergone a class switch as they do not contain human IgG. The GΔ mice contain only human IgG expressing B cells. The MGΔ mice contain very few if any B cells that express human Ig on the cell surface, but interestingly a proportion of the B220 cells express intracellular IgM, but not IgG (FIG. 2B). In contrast to the MΔGΔ and GΔ mice (see below), the MGΔ mice express mouse Ig light chains (FIG. 6G). These results show that the Cμ and Cγ genes in the different constructs are expressed and strongly suggest that the absence of CH1 is crucial for cell surface expression of VHH based antibodies.

Figure 2C:
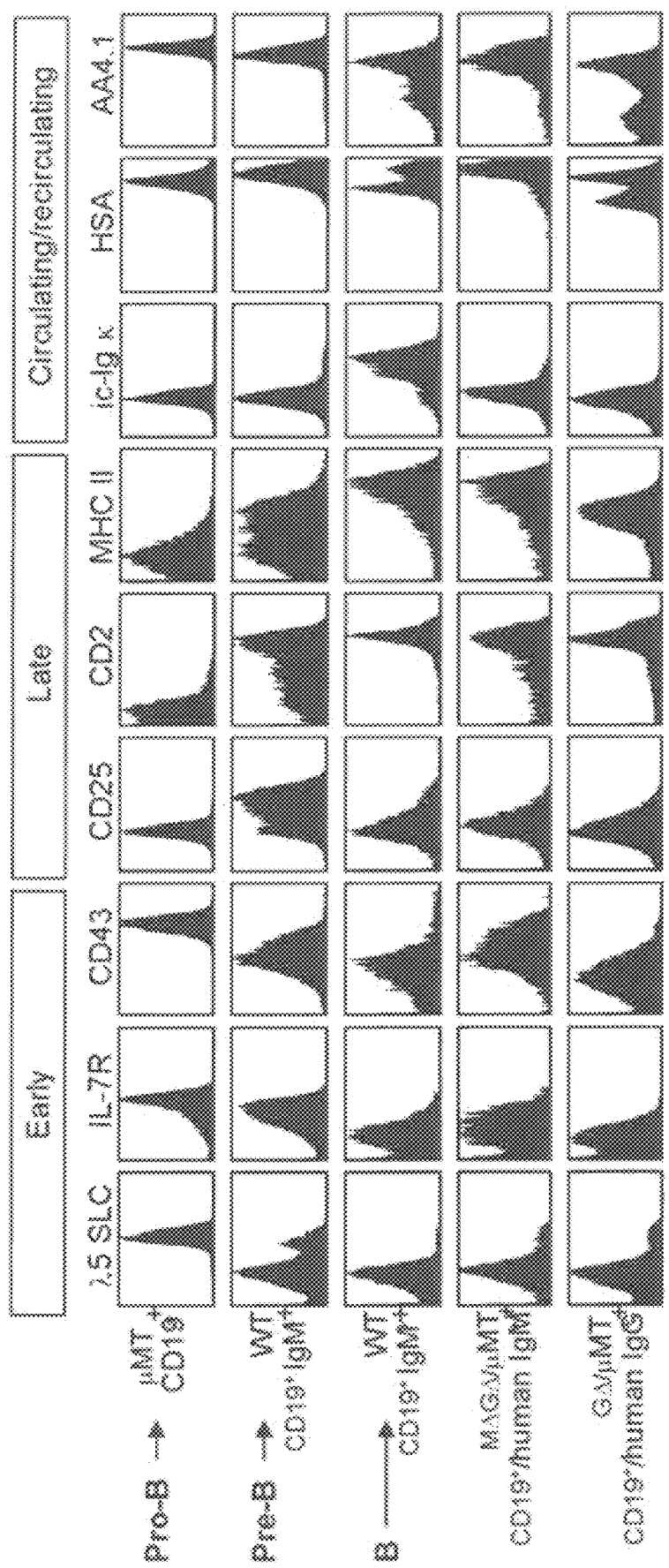

Human HCAb IgG and IgM Functionally Replace Murine (Pre-)BCR During B Cell Development in the BM During the developmental progression of large cycling into small resting pre-B cell the expression of specific cell surface markers is downregulated in a pre-BCR-dependent fashion [36], To investigate the capacity of human HCAb to functionally replace the pre-BCR, the expression of various markers was analysed by FACS. Pro-B cells express high levels of cytoplasmic SLC, IL-7R and CD43, which are downregulated upon pre-BCR expression and absent in mature B cells (FIG. 2C, compare pro-B cells from μMT mice and the surface IgM– pro-B/pre-B cell fraction and the surface IgM+ B cell fraction of wt mice).

The human Ig+ B cells from MΔGΔ/μMT or GΔ/μMT mice have low levels of SLC and IL-7R, indicating that the human single chain IgG and IgM receptors functionally replace the murine pre-BCR in the downregulation of SLC and IL-7R. For CD43 this appears to be the case only in GΔ mice, but the persistence of CD43 expression in MΔGΔ mice could be related to the finding of increased B-1 B cell differentiation in these mice. Likewise, CD2 and MHC class II expression is induced, as in normal pre-BCR signalling. The levels of the IL-2R/CD25, transiently induced at the pre-B cell stage, are very low on mature MΔGΔ or GΔ/μMT B cells and comparable to those of mature wt B cells (FIG. 2C). Furthermore, ic $I_{gk}$ expression was not detectable in mature MΔGΔ or GΔ/μMT B cells (FIG. 2C) and was also not induced in in vitro BM cultures upon IL-7 withdrawal after 5 days of $IL-7_+$ culture (not shown). Finally, the human HCAb expressing B cell populations in MΔGΔ or GΔ transgenic mice consisted partially of cells that were generated in the BM ($HSA_{high}$ and AA4. $1/CD93_{high}$), and partially of cells that have matured in the periphery and are recirculating ($HSA_{low}$ and $CD93_{low}$), comparable to findings in normal mice.

Collectively, these results show that human HCAb IgG and IgM functionally replace murine (pre-)BCR during B cell development with respect to the expression of developmentally regulated markers. Ig L chain is not induced (see below). cDNA analysis of BM RNA shows usage of both VHH segments for VDJ recombination, absence of CH1, and importantly a large diversity in the CDR3 region (FIG. 2D).

Multiple Rearrangements and Allelic Exclusion

A number of hybridomas were made from the MΔGΔ and GΔ lines after immunisation, in particular of the five copy GΔ line1 (see below). Sequence analysis showed that more than one rearrangement could take place in the multicopy GΔ loci. Of the 5 different 5 copy hybridomas analysed, one (G20) rearranged one copy which was in frame; two hybridomas (T7 and T12) had 2 rearrangements each with one out of frame in both; one hybridoma (T3) had two in frame rearrangements (J2 and J4); while one hybridoma (T1) had 4 rearrangements with 2 in frame (J2 and J4).

Figure 3F:
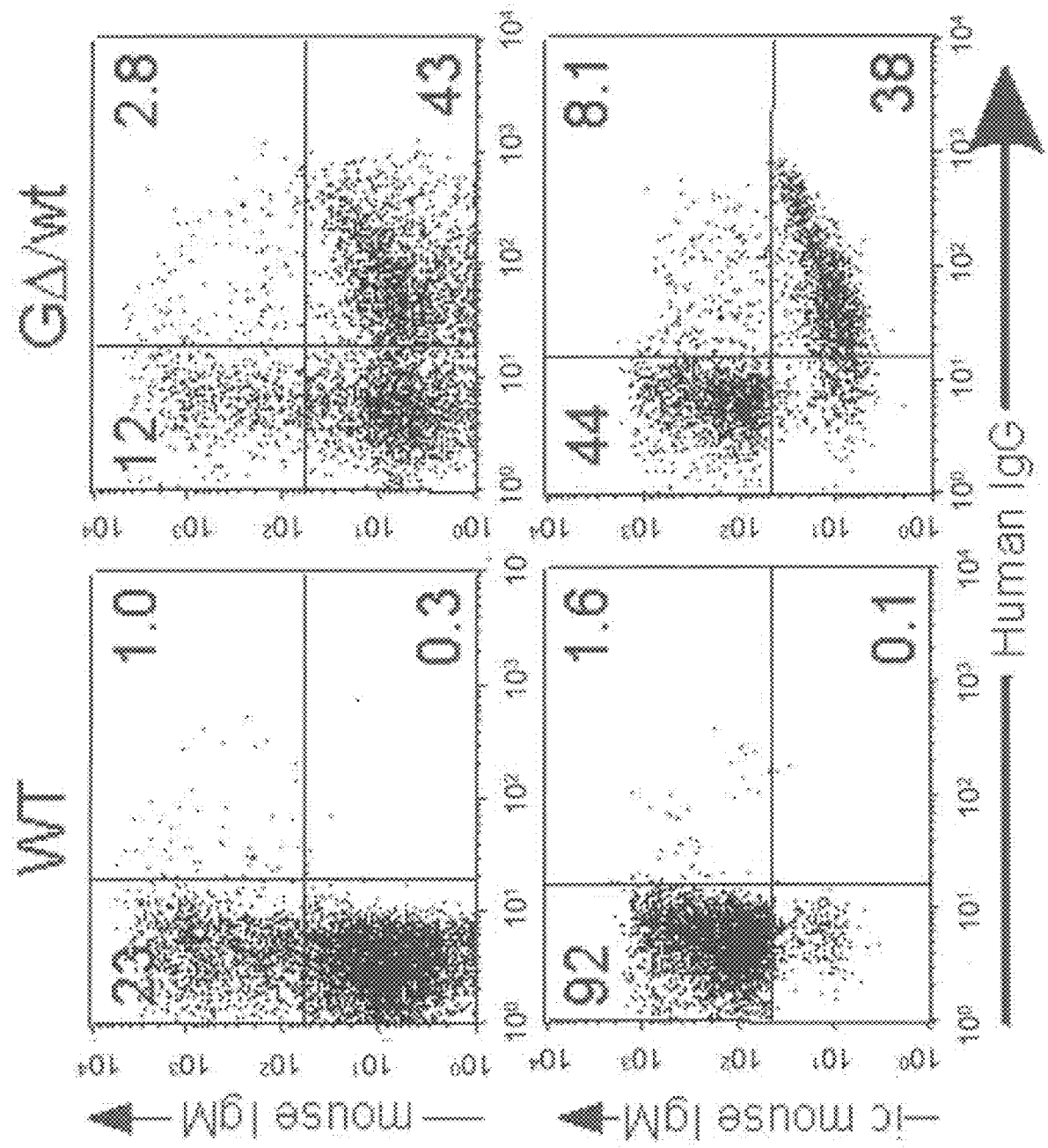

T1 and T3 express two productive mRNA's, that were confirmed by mass spectrometry of the secreted antibodies exactly matching the cDNA (not shown). We also carried out DNA stretched fiber FISH and normal DNA FISH on two different hybridomas: G20 (1 rearrangement) and T1 (4 rearrangements), using an LCR probe detecting each copy, and a probe located between VHH and D segment detecting only non-rearranged copies (FIG. 3 A-E). Control lung cells showed five complete copies plus half a transgene at either end (FIG. 3A) in agreement with Southern blot mapping (not shown), while the hybridomas indeed show one and four rearranged copies in G20 and T1 respectively (FIG. 3B, C-E). Thus multiple copies can successfully rearrange on the same allele. We next asked whether the HCAb loci have any (dis)advantage over the normal murine loci and whether there is allelic exclusion of loci. B220/CD 19 positive BM cells of GA line1 transgenic mice in a wt background were analyzed for the expression of human IgG and mouse IgM. Clearly the GΔ B cells express either mouse Ig or human Ig (FIG. 3F), showing allelic exclusion.

Splenic B Cells in G Δ, M ΔG Δ and MG Δ Transgenic Mice

Figure 4A:
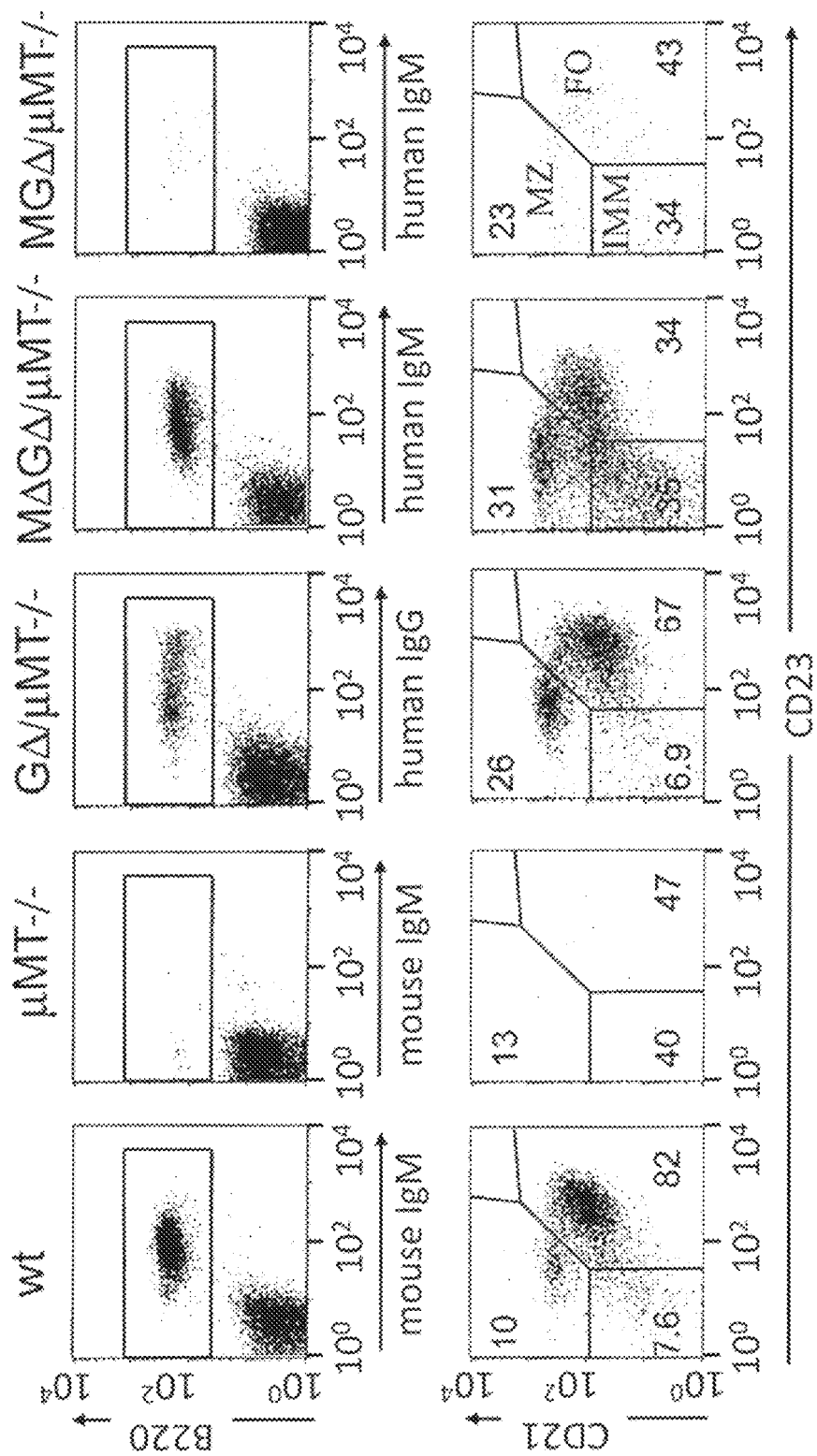
Figure 4B:
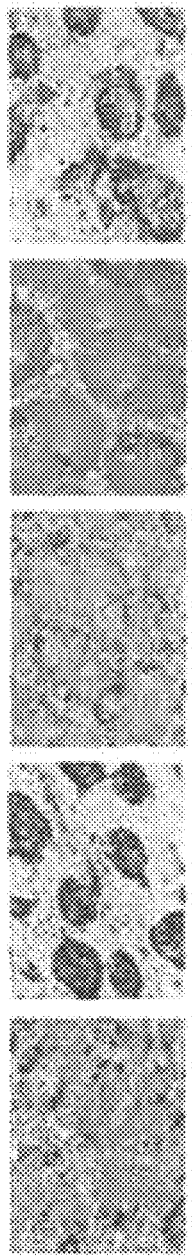

To determine the effect of the transgenes on B cell differentiation in μMT mice, we examined spleen B cell subpopulation sizes by flow cytometry, using the CD21/CD23 profiles (FIG. 4A). In GΔ mice, the proportions of $CD21_{low}CD23_{low}$ immature B cells were in normal ranges, and human single chain IgG expressing cells were able to differentiate both into follicular (FO; $CD21_+CD23_+$) and into marginal zone (MZ; $CD21_{high}CD23_{low}$) B cells. In the MΔGΔ mice the immature B cell fractions were increased, indicating that differentiation of HCAb IgM expressing cells into FO and MZ 8 B cells is somewhat impaired. In these spleens, reduced expression of CD23 was accompanied by increased surface expression levels of CD43 and CD5, indicative of differentiation into the B-1 B cell lineage. The few human IgM expressing B cells (also expressing mouse light chains see FIG. 6) present in MGΔ transgenic mice manifested a FO/MZ distribution that was similar to the one in MΔGΔ transgenic mice. MΔGΔ and GΔ, but not MGΔ mice, have a normal spleen architecture showing segregation of T cell clustering in the peri-arteriolar lymphocyte sheet (PALS) surrounded by B cell-rich areas containing follicles and marginal zones present at outer boundaries of the white pulp (FIG. 4B).

They also form germinal centers in B cell follicles of secondary lymphoid tissues (not shown) comparable to wt during T cell-dependent antibody responses. These are the sites of memory formation and affinity based selection due to somatic hypermutation. In the GΔ mice human IgG positive cells are detected in these germinal centers. We confirmed hypermutation of the human IgG genes by cDNA analysis from B cells present in Payer's patches. (FIG. 4C). Both VHH1 and VHH2 are used. Taken together, these findings demonstrate that in GΔ and MΔGΔ transgenic mice immature B cells that migrate from the BM have the capacity to differentiate in the spleen into both FO and MZ B cells, and to undergo somatic hypermutation after antigenic challenge.

Single Copy Loci Rescue Efficiently and CH1 Absence is Essential

Figure 4D:
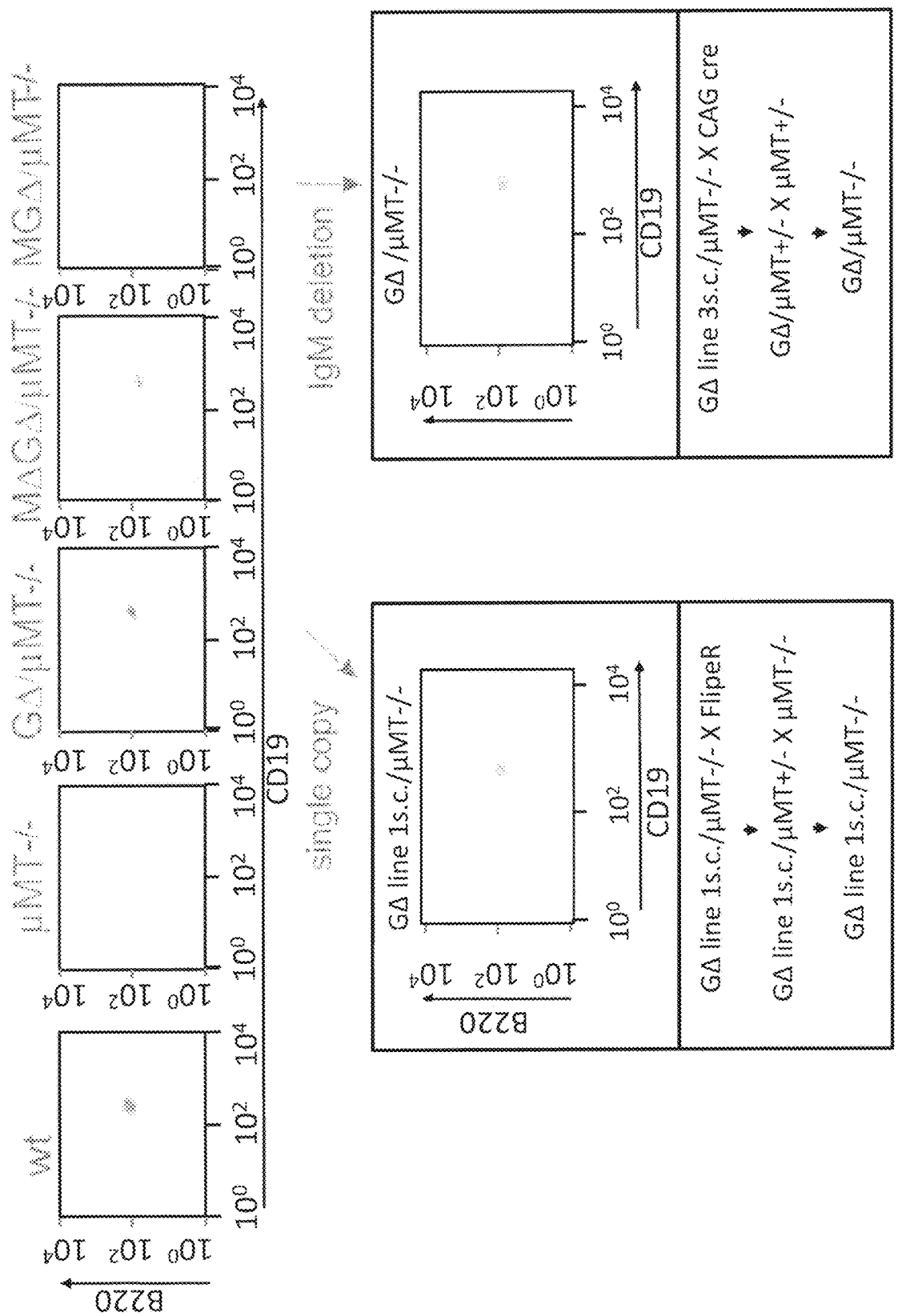

The GΔ line1 mice (FIG. 2A) contained 5 copies of the GΔ locus and hence there was a possibility that the efficient rescue was related to the copy number of the locus. However a single copy transgenic line obtained from the 5 copy GΔ line1 by Flp recombination through breeding with a FlpeR $line_{23}$, rescued B cell development to a similar extent (FIG. 4D, FIG. 2A). It was confirmed that a single copy of the locus is sufficient for rescue and that the presence of the Cμ constant region with a CH1 region is inhibitory, by deleting the Cμ, and Cδ regions from the non-rescuing single copy line MGΔ (line 3) by Cre recombination (breeding to a ere expressing line) resulting in a single copy GΔ line (FIG. 4D). The previously non-rescuing locus now gives the same B cell development 9 as the other GΔ lines. Thus copy number does not affect rescue and presence of CH1 in the Cμ region inhibits B cell rescue (see also below).

Mouse Ig Light Chain Loci do not Rearrange in MΔGΔ and GΔ Transgenic Mice

Murine Ig light chain proteins were not detected in the MΔGΔ and GΔ mice by Western blots of serum (not shown, but see FIGS. 2C and 6A) or by FACS, suggesting that the murine light chain genes do not rearrange. This was confirmed by comparing the densities of the Ig κ locus germline signals in DNA from sorted splenic B220+ cell fractions and liver cells by Southern blot analysis (FIGS. 5A and B), which shows that the mouse light chains do not rearrange and remain in a germline configuration. In contrast light chains are detected in the few human Ig expressing cells in the MGΔ/μMT mice (See FIG. 6G).

Thus the expression of human HCAb in early B cell development in the BM fails to provide the signal leading to light chain rearrangement. In this context, the HCAb mimic a BCR rather than a pre-BCR, which is likely related to their failure to bind pseudo-light chains in the absence of CHI [61].

Serum Analysis of G Δ/μMT and M ΔG Δ/μMT mice.

Human IgM was present in MΔGΔ serum and human IgG in both MΔGΔ and GΔ mouse serum. In non-immunized adult animals, the human IgM (<50 μg/ml) and IgG (200-1000 μg/ml) is present at levels comparable to those seen in normal mice or transgenic mice carrying a normal human IgH locus [65]. Gel electrophoresis of the serum of all six GΔ mice revealed HCAb IgG's with a MW of ~70 kD under non-reducing and ~35 kD under reducing conditions, consistent with heavy chain dimers lacking a light chain and each heavy chain lacking the CH1 exon (FIG. 6A,B).

The serum of MΔGΔ mice contained multimeric heavy chain-only human IgM. Under reducing conditions (FIG. 6C) all four lines contained IgM chains with the MW as a human control IgM after subtraction of the MW of CH1. The serum was also fractionated (FIG. 6D horizontal fractions) under non-reducing conditions after which each fraction 10 was analysed by gel electrophoresis under reducing conditions (FIG. 6D, vertical lanes). When compared to the human serum pentameric 900 kD IgM control the transgenic IgM fractionates at 600 kD consistent with it also being multimeric and lacking light chains and CH1. Thus MΔGΔ mice produce HCAb multimeric IgM and dimeric IgG, while GΔ produce dimeric IgG in the serum.

Serum Analysis of MG Δ Mice

In the periphery and spleen of MGΔ/μMT lines, almost no B220 positive cells (<1% of the wild type) and only occasional small B cell clusters are seen in spleen (FIG. 4B). Small quantities of human IgM and IgGs were detected in the serum only after purification (FIG. 6E,F). The human IgM in these mice was normal size under reducing conditions, whereas the circulating human IgGs are shorter (apparent MW of 35 kD, consistent with a CH1 deletion). Interestingly mouse K light chains, presumably associated with the human IgM, were also detected (FIG. 6G).

Human IgM and IgGs were below the detection level in a quantitative ELISA assay, but we nevertheless tested whether the MGΔ/μMT mice can respond to immunization. Mice were immunized with human Tumor Necrosis Factor-α (TNF-α) and wt mice developed a strong TNF-α specific antibody response, while in the two MGΔ line 3 mice used, antigen specific human IgGs could not be detected by ELISA or Western blot analysis (not shown).

Immunisation of MΔGΔ and GΔ Mice Results in Antigen Specific Ab Production

The GΔ/μMT mice were immunized with *E. Coli* hsp70, DKTP {Diphteria toxoid, whole cell lysate of *Bordetella Pertussis*, Tetanus toxoid and inactivated polio virus types 1, 2 and 3) and rtTA [50], while the MΔGΔ mice were immunized with human TNFα. From mice with positive sera by ELISA, individual complete antibodies were isolated using hybridomas or single domain Ab (sdAb) by phage display libraries.

Figure 7A:
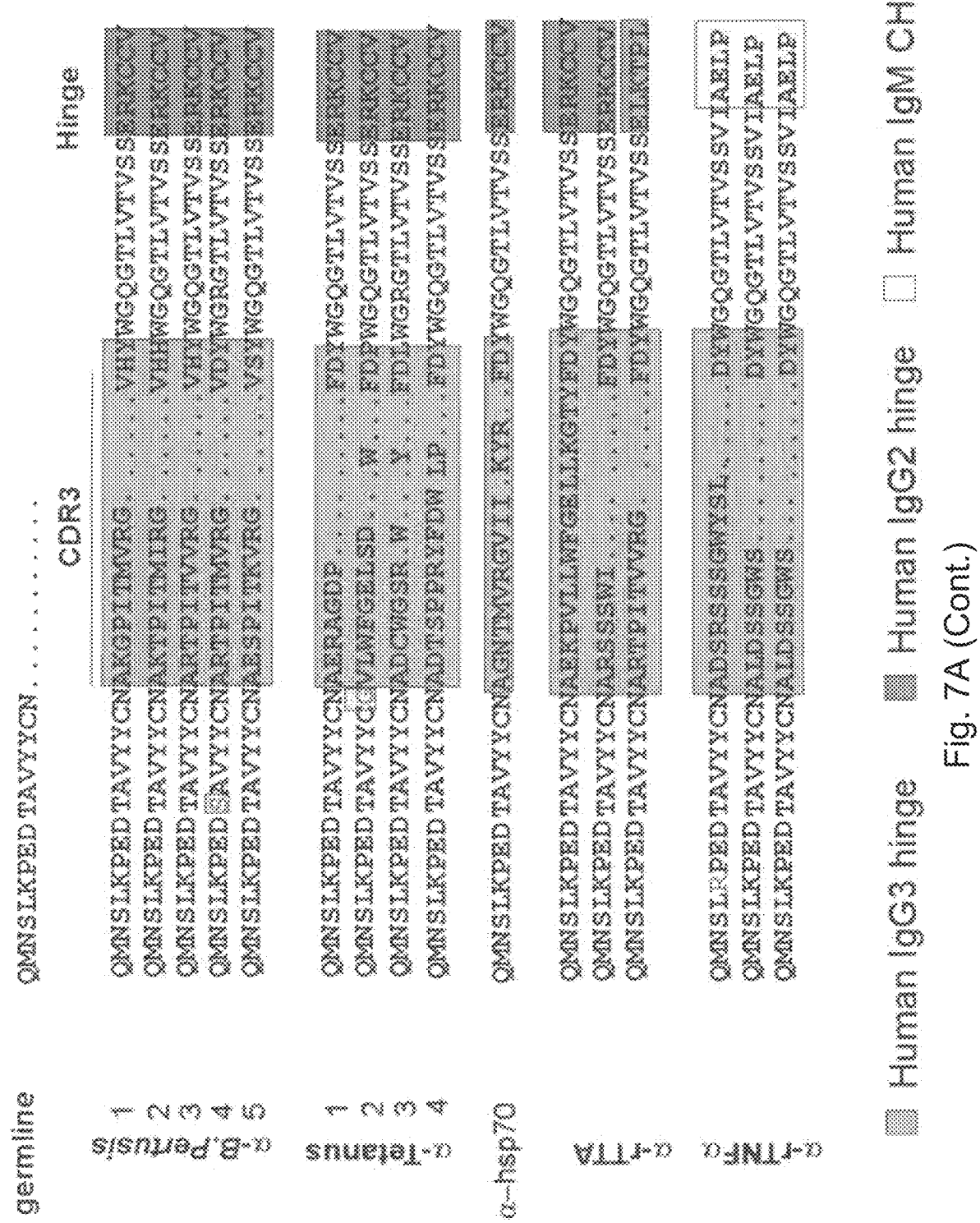
Figure 7B:
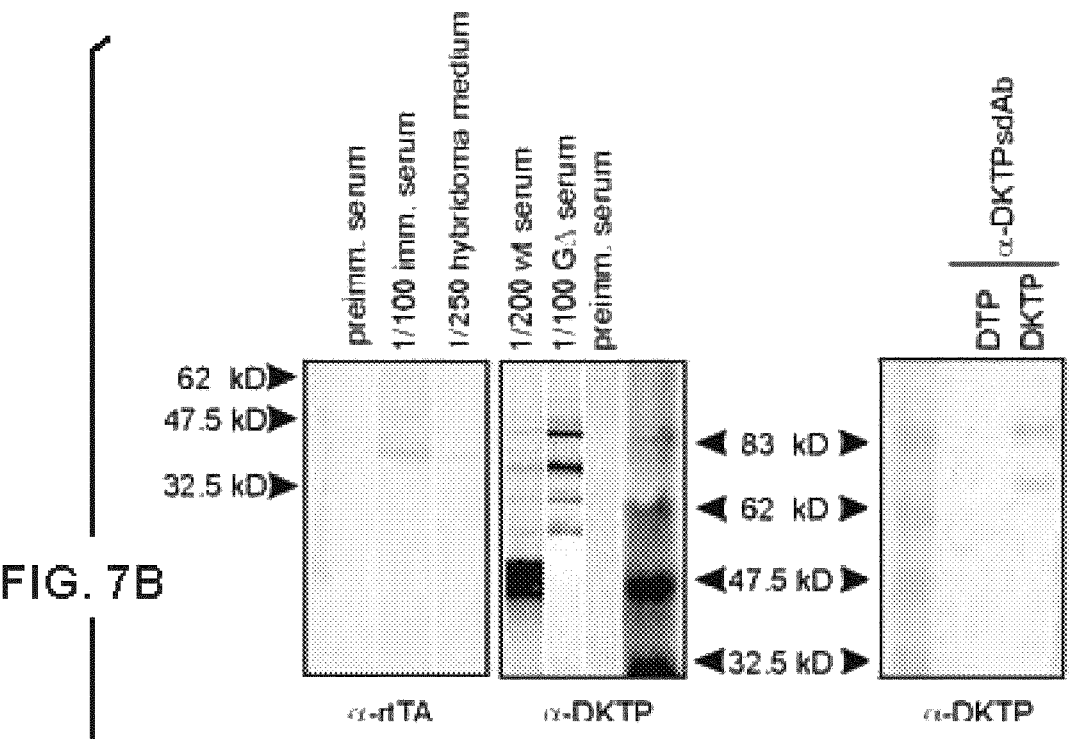
Figure 7C:
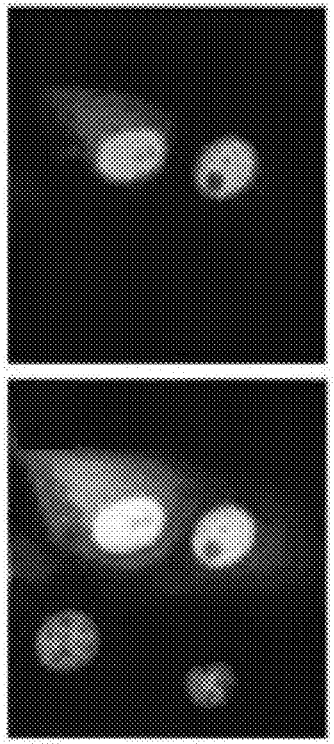
Figure 7D:
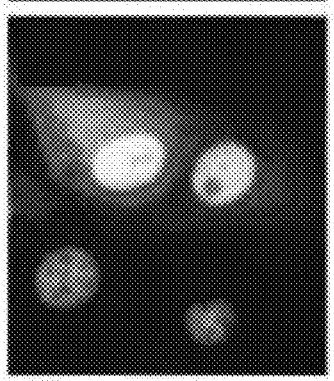
Figure 7E:
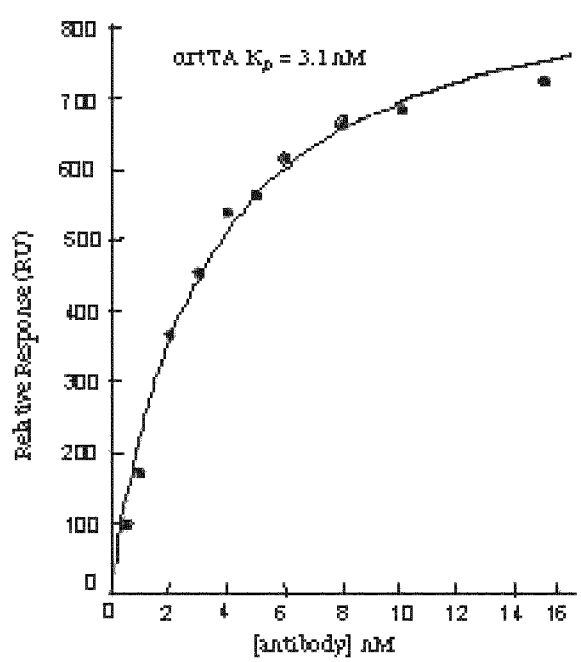

The αhsp70-, tetanus toxoid- and rtTA-specific monoclonals were sequenced after RTPCR of the antibody RNAs (FIG. 7A). This showed that both IgG2 (7 out of 8) and IgG3 (1 out of 8) antibodies were produced (the sdAb were isolated from a IgG2 library). Different D and J regions were used. Although not at high frequency, the VHH from the 11 HCAbs were hypermutated. The three hTNFα-specific antibodies (one positive IgM hybridoma, FIG. 6 α-hTNFα #1 and two sdAb α-hTNFα #2 & 3) all had different hypermutations in the CDR2 region. When comparing the sequences of all 14 antibodies it was evident that although all J regions are used, like in humans JH4 is used most frequently. Surprisingly all antibodies contained llama VHH2 (with a glutamine (Q) rather than the archetypical glutamic acid at position 49 [51]). Lastly clearly the CDR3 region provides most of the diversity$_{27}$. It varies between 10 and 20 aminoacids in length (average of 13.6 aa), very similar to that normally seen in llamas and humans [52, 53]. We next tested whether these HCAbs are functional in regular assays as hybridoma supernatants and bacterial periplasmic fractions of sdAbs (FIG. 7). All of the antibodies were positive in ELISA's and all were positive in antigen detection on Western blots (e.g. α-DKTP and α-rtTA serum and hybridoma medium and α-*B. Pertussis* sdAb, FIG. 7B). We also tested the α-rtTA IgG in immunocytochemistry using a cell line transfected with a rtTA expression plasmid (FIG. 7C, D). The rtTA HC-IgG gave a very clear and specific nuclear staining. The affinity of a number of the antibodies was high, although some (particularly sdAb) were much lower. For example the α-rtTA antibody used in the immunocytochemistry (FIG. 7C, D) was approximately 3 nM as determined on a BiaCore (FIG. 7E).

Conclusions

Here we reported the expression of modified HCAb loci that rescue B cell development in μMT mice resulting in functional HCAb production. These mice can be immunized to produce antigen specific HCAb. As in camelids, removal of CH1 is crucial for HCAb-secretion, but the single camelid (review$_{30}$) splice mutation at the 3'CH1/intron border is not sufficient for CH1 elimination, thus more than this single point mutation is required, at least in the human locus. IgM with CH1 in combination with a VHH blocks B cell development, probably caused by an ineffective assembly of an IgM surface molecule in the context of the pre-BCR. In contrast mice expressing a HCD-like human μ protein develop normal CD43-pre-B cells in a SCID background independent of λ5 [54]. The truncated Cμ proteins are expressed on the B cell surface without associated L chains and are thought to mimic pre-BCR signaling through self-aggregation [55].

Normally BiP chaperones the folding and assembly of antibody molecules by binding to hydrophobic surfaces of the Ig chains that subsequently participate in inter-chain contacts$_{31}$. The presence of hydrophilic amino acids in FR2 of VHHs, most probably prevents BiP binding to VHH, which needs no (surrogate) light chain to become soluble. At the same time, CH1 provides the interaction with BiP proposed to hold heavy chains in the ER until assembly (replacement of BiP by a light chain) is complete. At the level of pre-B cell receptor, our results suggest that transgenic μ heavy chain pairing with the Vpre protein, as part of a surrogate light chain (SLC) in the noncovalent association with λ5 protein, would not be able to take place when the μ heavy chain containing a CH1 domain is linked to a VHH. Thus the human IgM in MGS and MGΔ transgenic mice would in this regard resemble an incomplete pre-BCR-like complex known to be insufficient to signal proliferative expansion and developmental progression [56, 57]. This may explain why only 30% of the B220 positive cells in BM have intracellular IgM (FIG. 2B). The presence of the few matured B cells in spleen of these mice may be explained by the recently described novel receptor complex that contains a μ heavy chain but lacks any SLC or conventional light chains [58], When CH1 is absent from Cγ2 and 3 and IgM is removed from the locus there is rescue of B cell development, showing that IgG can functionally replace IgM. An IgG1 receptor, expressed from the pro B cell stage onwards, is able to substitute for IgM in supporting the development of mature CD21 +B cells in Rag2−/− mice [59]. Recently it was also shown that a pre-rearranged camelid IgG2a could partially rescue B cell development in one out two transgenic mice in a μMT (and a CΔ−/−) backgrounds. In our case IgM or IgG lacking CH1 rescue B cell development in 10 out of 10 independent transgenic mouse lines. In addition, we do not observe light chain rearrangement and conclude that light chain expression is not required for further B cell differentiation. The difference in the results obtained here and those of Zou et al. [60] may be explained by the level of expression of the heavy chain locus (and thus signaling) due to the inclusion of the LCR on our constructs. Our results confirm that truncated μ heavy chain protein lacking CH1 [61] or VH and CH1 [62], cannot associate with SLCs and fail to activate K gene rearrangement.

The 5 copy GΔ line1 (and other multicopy lines), rescues B cell development to the same extent as the single copy line integrated at the same position in the genome. Interestingly, one or more rearrangements occur in multicopy transgenic loci (FIG. 3). Two of the hybridomas, originating from two single splenocytes gave two productive HCAb transcripts and proteins. This result confirms that expression of two antibodies in the same B cell is not toxic [63], However the prediction$_{37}$ that double antibody producing B cells would loose in competition with single antibody producing cells under antigen challenge is not borne out by our result of finding 2 double antibody expressing cells out of 5 hybridomas obtained after antigen challenge.

The (multicopy) locus is subject to allelic exclusion in wildtype mice, because BM cells express either mouse or human Ig on the cell surface. There is no significant population of cells expressing both on the cell surface (FIG. 3F, top panels). Perhaps most interesting is the number of mouse versus human Ig expressing cells. In a wt/5 copy GA mouse there are three possible alleles available for rearrangement, two mouse alleles with one Ig locus and one allele with five human HCAb loci. If chosen stochastically, a human allele would be chosen only 1 out of 3 times.

If the numbers of loci are counted, the human locus would rearrange first in 5 out of 7 cells. However, endogenous mouse and transgenic human HCAb is expressed almost equally (44/38, FIG. 3F bottom panels). Although these numbers ignore possible deviations from the random use of V regions and a possible position effect on the transgenic locus, they strongly suggest that the first choice is a stochastic choice of allele followed by the possible rearrangement of multiple genes per allele.

This agrees with the fact that we frequently observe multiple rearrangements of the GA locus. Normally, a productive rearrangement downregulates recombination to prevent rearrangement of the other allele. However, the multiple copies on the transgenic allele are present on the same open locus and apparently can be recombined before RAG downregulation. This could be because multiple rearrangements take place at the same time or, if it involves a spatial component ("compartment"), that there would be sufficient time to rearrange another gene in the locus as it would be close before the RAGs are downregulated.

Only when a rearrangement is not productive in wt mice (no signaling and the RAGs stay on) would there be sufficient time for a second locus to be activated, replace the first locus and be rearranged. In favor of this argument would be the observation that other species with multiple loci on the same chromosome have more cells expressing two Abs [64].

Importantly these experiments show that HCAb loci can be expressed successfully in the mouse. Antigen challenge results in the production of high affinity antigen specific human HCAb of different class dependent on the composition of the loci. These antibodies are expressed at levels comparable to those in normal mice or other "normal" human IgH transgenic mice [65], Only two variable regions were used in our experiments yet high affinity antibodies with diverse specificity were successfully isolated to almost all of the totally unrelated proteins we tested, demonstrating the efficiency and efficacy of the diversity generated by CDR3 [66]. Thus having V(D)J recombination and in vivo selection provides a critical advantage over the generation of human single chain antibody fragments from phagemid libraries using phage display$_{39}$. Hybridomas can be generated easily, which importantly allows the direct cloning and expression of the complete human HCAb or sdAb fragment without the need of phage display and further screening.

Thus these mice open up completely new possibilities for the production of human HCAbs for clinical or other purposes, particularly in light of the evidence$_4$ that HCAbs may recognize epitopes that are barely antigenic for conventional antibodies, such as active sites of enzymes. The restricted number of variable regions may explain why not all of the antigens were recognized; the polio and Diphteria proteins gave no response in GΔ mice, whereas wt control mice did. Surprisingly all of the antibodies had the llamaVHH2 region. This does not include a conserved aminoacid [67] at position 49 in contrast to VHH1 that does have one and should be more soluble.

Nevertheless we expect that the addition of more variable regions in the locus would lead to an even broader repertoire. Whilst it is preferable to avoid multiple copies of the locus on a single allele, it would be advantageous to generate mice containing multiple alleles each comprising a single copy of different VH regions to increase diversity. In such new loci one can use either normally occurring (human) VH regions or VH regions engineered for increased solubility$_{18}$ and light chain pairing.

In conclusion, we have demonstrated that antigen specific high affinity HCAb of potentially any class can be produced in mice. This technology will allow the production of fully human HCAb of any class or fragments thereof in response to antigen challenge for use as therapeutic or diagnostic agents in man. By using different vertebrate loci our technology also allows for the production of high affinity matured antibodies from any vertebrate for use as reagents, diagnostics or for the treatment of animals.

Example 2

Janssens et al. (2006) have shown that a transgenic $V_H$ locus recombines properly to produce transgenically coded heavy chain only antibodies and that such a locus is sensitive to allelic exclusion in the presence of the endogenous (mouse) heavy chain immunoglobulin locus. In order to show that the number of $V_H$ transgenic loci, that is used for heavy chain only antibody production, can be increased by using the process of allelic exclusion, two transgenic mice containing different heavy chain only loci were crossed resulting in offspring containing both loci. One mouse contained the MGΔ locus (IgM and IgG locus, Janssens et al., 2006), while the other contained the GΔ locus (IgG locus only, Janssens et al., 2006), both mice have the μMT background. Hybridomas were derived from the B cells from the double transgenic offspring and grown in culture by standard methods. A number of the resulting individual monoclonal cell lines were analysed by PGR and Southern blots, which showed that lines containing a productively rearranged MGΔ locus contained a non-rearranged GΔ or a non-productively rearranged GΔ locus. Conversely cell lines containing a productively rearranged GΔ locus contained a non-rearranged or a non-productively rearranged MGΔ locus. Thus the sum of the available $V_H$ regions is used in the recombination process.

Examples 3 and 4

In a preferred embodiment of the first aspect of the invention all of the number of functional human VH regions is increased by cloning human $V_H$ regions (or variants thereof) onto a multiple modified human locus containing the entire $D_H$ region, the entire $J_H$ region and a combination of the Cμ, Cγ2, Cγ3 and Coo regions and the 3'LCR using those methods described in the previous example and known in the art (Janssens et al 2006). This procedure can be carried out using multiple identical $V_H$ regions on separate loci or different $V_H$ region on separate loci. The different loci can contain identical heavy chain regions or different heavy chain regions. The example 3 is for a locus with identical $V_H$ regions on loci that have a different combination of heavy chain regions, example 4 for two loci with identical heavy chain constant regions but different V$_H$ regions. Obviously in both examples additional loci could be added.

Example 3

Human V$_H$ regions are isolated by PCR amplification of the human genomic DNA using primers that are specific for each selected V$_H$ out of the possible 39 functional human V$_H$ regions (alternatively human V$_L$ regions or TCR V regions or variants of all of these derived by mutagenesis could be used or added). The human V$_H$ regions are cloned in sets onto the locus described in the above example (FIG. 9), i.e. comprising the human D$_H$ plus J$_H$ (or other D and J regions) and Cμ, Cγ2, Cγ3 each lacking a CH1 plus 3' LCR. The Cα region lacking CH1 plus switch regions will be cloned separately in the GΔ locus (FIG. 10). This GΔ locus is a variant of the original locus in that it does not contain lox sites and the llama V$_{HH}$ regions were removed by standard homologous recombination leaving a unique PI-PspI site (FIG. 10).

The functional V$_H$ regions may be cloned together, with any multiple on each locus. Initially, 17 functional human V$_H$ regions will be cloned together in one set starting with 2 cloned genes per set. To each of these initial constructs, a second set will be added by conventional methodology (e.g. using XhoI-SalI restriction digestion/ligation, ligation of XhoI and SalI compatible sites destroys both). Sets containing 4, 4, 4, 3 and 2 will be linked into one set of 17 genes in a BAG vector. Obviously this procedure could be carried out by combining sets containing other numbers of genes. The above process may be terminated at any point to achieve the desired number of V$_H$ regions or extended to achieve a higher number of V$_H$ regions.

The entire set (e.g. 17 genes) is cloned into the modified GΔ locus in the unique PI-PspI site. The Cα region will be cloned into the I-CeuI site of this locus resulting in a AAGA locus capable of producing Igα and IgG (FIG. 10). Alternatively other heavy chain regions could be cloned in.

These final loci are then introduced into separate transgenic mice (preferably with a defective mouse IgH locus such as μMT) as described in the example above. These separate loci are used to generate separate mouse lines, one that would make only IgG and one that would make IgA and/or IgG. These mice are subsequently crossed to bring the total of V$_H$ regions available to 34 on two different loci. Crossing these mice to homozygosity for both loci would make 68 V$_H$ regions available for recombination. Having multiple copies of an integrated locus would increase this number yet further. The analysis of hybridomas made from the B cells from these mice would be used to show that when a productively rearranged locus is present, the other loci that were bred in, are either non-rearranged or non-productively rearranged due to allelic exclusion by standard procedures.

Example 4

Different sets of 1 or more V$_H$ regions similarly isolated to the regions described above (or variants thereof derived by mutagenesis) are cloned onto two separate loci by the same methodology as described above. This would result in two different GΔ loci (or variants thereof such as adding Cα). These loci would be introduced into separate mice resulting in separate transgenic lines (for example 2 loci having 10VH domains each, FIG. 11). These mice would subsequently be crossed to obtain double transgenic mice that would have all of the V$_H$ regions used available for the recombination process. Crossing these mice to homozygosity for both loci would double the number of VH regions available for recombination (FIG. 12 karyogram with one locus integrated on chromosome 1 and one locus on chromosome 8). Having multiple copies of an integrated locus would increase this number yet further. The analysis of hybridomas made from the B cells from these mice would be used to show that when a productively rearranged locus is present, the other loci that were bred in, are either non-rearranged or non-productively rearranged due to allelic exclusion.

The above process may be terminated at any point to achieve the desired number of V$_H$ regions. The D, JH and constant regions will be added to these VH regions. These final loci can then be introduced into separate transgenic mice (preferably with a defective mouse IgH locus) as described in the example above. Alternatively the position of the lox sites allows the elimination of individual constant regions to generate separate loci that contain or Cμ (IgM) alone, or Cγ2 and Cγ3 (IgG2 and IgG3) alone, or Cα alone (IgA) or combinations thereof. These separate loci are used to generate separate mouse lines that would make either human IgM alone, or IgG alone or IgA alone or combinations thereof.

REFERENCES

[1] Kabat, E., Wu, T. T., Perry, H. M., Gottesman, K. S., and Foefier, C. (1991) United States Public Health Services Publication No. 91-3242, National Institutes of Health, Bethesda, Md.
[2] Jaton et al., (1968) Biochemistry, 7, 4185-4195
[3] Xu and Davies, (2000) Immunity, 13, 37-45
[4] Jakobovits A. The long-awaited magic bullets: therapeutic human monoclonal antibodies from transgenic mice. Expert Opin Investig Drugs. 1998 April; 7(4):607-14. Links
[5] Davis C G, Jia X C, Feng X, Haak-Frendscho M. Production of human antibodies from transgenic mice. Methods Mol Biol. 2004; 248:191-200.
[6] Kellermann S A, Green L L. Antibody discovery: the use of transgenic mice to generate human monoclonal antibodies for therapeutics. Curr Opin Biotechnol. 2002 December; 13(6):593-7. Links
[7] EP1690935
[8] US2005287630
[9] WO9634096
[10] WO9402602
[11] Hendershot et al., (1987) J. Cell Biol., 104, 761-767;
[12] Brandt et al., (1984) Mol. Cell. Biol., 4, 1270-1277
[13] Hamers-Casterman et al., (1993) Nature, 363, 446-448
[14] Stanfield et al., (2004) Science, 305, 1770-1773
[15] Rick Janssens, Sylvia Dekker, Rudi W. Hendriks, George Panayotou, Alexandra van Remoortere, John Kong-a San, Frank Grosveld and Dubravka Drabek, Generation of heavy chain only antibodies in mice, Proc. Natl Acad USA 2006, 10; 103(41): 15130-5. Epub 2006 Oct. 2.
[16] de Genst et al., Dev Comp Immunol. 2006; 30:187-98
[17] Davies, J and Riechmann L. Biotechnology (1995) vol 13, 475-479 Antibody VH domains as small recognition units
[18] Ward et al., (1989) Nature, 341, 544-546
[19] Davies and Riechmann, (1996) Protein Eng., 9 (6), 531-537;
[20] Lutz and Muyldermans, (1999) J. Immuno. Methods, 231, 25-38
[21] Tanha et al., (2001) J. Biol. Chem., 276, 24774-24780

[22] Yau et al., (2005) J. Immunol. Methods, 297, 213-224
[23] Van Dijk and van der Winkel, Curr. Opin. Chem. Biol., (2001) Aug. 5 (4), 368-374
[24] Leher et al., (1999) Exp. Eye. Res., 69, 75-84
[25] Sitia et al., (1990) Cell, 60, 781-790
[26] Jespers L, Schon O, Fatnm K, Winter G. (2004) Aggregation-resistant domain antibodies selected on phage by heat denaturation. Nat Biotechnol. 22(9): 1161-5.
[27] Ravn P, Danielczyk A, Jensen K B, Kristensen P, Christensen P A, Larsen M, Karsten U, Goletz S. (2004) Multivalent scFv display of phagemid repertoires for the selection of carbohydrate-specific antibodies and its application to the Thomsen-Friedenreich antigen. J Mol Biol. 343(4):985-96.
[28] Jespers L, Schon O, James L C, Veprintsev D, Winter G. (2004) Crystal structure of HEM, a soluble, refoldable human V(H) single domain with a germ-line scaffold. J. Mol. Biol. 337(4): 893-903.
[29] Dolk E, van Vliet C, Perez J M, Vriend G, Darbon H, Ferrat G, Cambillau C, Frenken L G, Verrips T. (2005) Induced refolding of a temperature denatured llama heavy-chain antibody fragment by its antigen. Proteins. 59(3):555-64.
[30] Dolk E, van der Vaart M, Lutje Hulsik D, Vriend G, de Haard H, Spinelli S, Cambillau C, Frenken L, Verrips T. (2005) Isolation of llama antibody fragments for prevention of dandruff by phage display in shampoo. Appl Environ Microbiol. 71(1):442-50.
[31] Zhao, Y., Pan-Hammarstrom, Q., Zhao, Z., Wen, S. & Hammarstrom, L. Selective IgG2 deficiency due to a point mutation causing abnormal splicing of the Cgamma2 gene. Int Immunol 17, 95-101 (2005).
[32] Lefranc, M., Giudicelli, V., Ginestoux, C., Bodmer, J., Muller, W., Bontrop, R., Lemaitre, M., Malik, A., Barbie, V. and D. Chaume. 1999. IMGT, the international ImMunoGeneTics database Nucleic Acids. Res. 127: 209-212.
[33] Mills F, Harindranath N, Mitchell M &Max E. Enhancer complexes located downstream of human C alpha genes. J Exp. Med. 186, 845-58 (1997)
[34] Nguyen, V. K., Hamers, R., Wyns, L. & Muyldermans, S. Loss of splice consensus signal is responsible for the removal of the entire C(H)1 domain of the functional camel IGG2A heavy-chain antibodies. Mol Immunol 36, 515-24 (1999).
[35] Imam A, Patrinos G, de krom M, Bottardi S, Janssens R, Katsantoni E, Wai A, Sherratt D & Grosveld F. Modification of human P-globin locus PAC clones by homologous recombination in E. Coli. Nucleic Acids Res. 15, E65 2001)
[36] Middendorp, S., Dingjan, G. M. & Hendriks, R. W. Impaired precursor B cell differentiation in Bruton's tyrosine kinase-deficient mice. J Immunol 168, 2695-703 (2002).
[37] Melamed D and Nemazee D. Self-antigen does not accelerate immature B cell apoptosis, but stimulates receptor editing as a consequence of developmental arrest. Proc. Natl. Acad. Sci., 94, 9267-9272 (1997).
[38] Heiskanen M, Hellsten E, Kallioniemi O P, Makela T P, Alitalo K, Peltonen L, Palotie A. Visual mapping by fiber-FISH. Genomics 30, 31-36 (1995).
[39] Corput, M and Grosveld, F. Fluorescence in situ hybridization analysis of transcript dynamics in cells Methods 25, 111-118 (2001).
[40] Van der Linden R, de Geus B, Stok W, Bos W, van Wassenaar D, Verrips T, Frenken L. Induction of immune response and molecular cloning of heavy chain repertoire of Lama glama. J immunol Methods. 240, 185-195 (2000).
[41] Hoogenboom H. R, Griffiths A. D, Johnson K. S, Chiswell D. J, Hudson P, and Winter G. Multi-subunit proteins on the surface of filamentous phage: methodologies for displaying antibody (Fab) heavy and light chains. Nucleic Acids Research 19, 41334137 (1991).
[42] Dekker S, Toussaint W, Panayotou G, de Wit T, Visser P, Grosveld F, Drabek D. Intracellularly expressed single-domain antibody against pi5 matrix protein prevents the production of porcine retroviruses. J Virol., 77, 12132-9 (2003)
[43] Kitamura D, Roes J, Kuhn R & Rajewsky K. A B cell-deficient mouse by targeted disruption of the membrane exon of the antibody mu chain gene. Nature 350, 423-6 (1991).
[44] Macpherson, A. J. et al. IgA production without mu or delta chain expression in developing B cells. Nat Immunol 2, 625-31 (2001).
[45] Orinska, Z. et al. Novel B cell population producing functional IgG in the absence of membrane IgM expression. Eur J Immunol 32, 3472-80 (2002).
[46] Hasan, M., Polic, B., Bralic, M., Jonjic, S. & Rajewsky, K. Incomplete block of B cell development and antibody production in mice carrying the muMT mutation on the BALB/c background. Eur J Immunol 32, 3463-71 (2002).
[47] Davies, J and Riechmann, L. Single antibody domains as small recognition units: design and in vitro antigen selection of camelized, human VH domains with improved protein stability. Protein Eng. 9, 531-7 (1996).
[48] Riechmann, L. & Muyldermans, S. Single domain antibodies: comparison of camel VH and camelised human VH domains. J Immunol Methods 231, 25-38 (1999).
[49] De Genst E, Silence K, Ghahroudi M, Decanniere K, Loris R, Kinne J, Wyns L & Muyldermans S. Strong in vivo maturation compensates for structurally restricted H3 loops in antibody repertoires. J Biol Chem. 280, 14114-21 (2005)
[50] Urlinger S, Baron U, Thelhnann M, Hasan M T, Bujard H & Hillen W. Exploring the sequence space for tetracycline-dependent transcriptional activators: novel mutations yield expanded range and sensitivity. Proc Natl Acad Sci USA. 97, 7963-8 (2000).
[51] De Genst E, Silence K, Ghahroudi M, Decanniere K, Loris R, Kinne J, Wyns L & Muyldermans S. Strong in vivo maturation compensates for structurally restricted H3 loops in antibody repertoires. J Biol Chem. 280, 14114-21 (2005)
[52] Vu, K. B., Ghahroudi, M. A., Wyns, L. & Muyldermans, S. Comparison of llama VH sequences from conventional and heavy chain antibodies. Mol Immunol 34, 1121-31 (1997).
[53] Zemlin, M. et al. Expressed murine and human CDR-H3 intervals of equal length exhibit distinct repertoires that differ in their amino acid composition and predicted range of structures. J Mol Biol 334, 733-49 (2003).
[54] Corcos D, Iglesias A, Dunda O, Bucchini D, Jami J. Allelic exclusion in transgenic mice expressing a heavy chain disease-like human mu protein. Eur J Immunol. 21, 2711-6 (1991)
[55] Corcos D, Dunda O, Butor C, Cesbron J Y, Lores P, Bucchini D, Jami J. Pre-B-cell development in the absence of lambda 5 in transgenic mice expressing a heavychain disease protein. CurrBiol. 5:1140-8 (1995).

[56] Seidl, T., Rolink, A. & Melchers., F. The VpreB protein of the surrogate lightchain can pair with some mu heavy-chains in the absence of the lambda 5 protein. Eur J Immunol 31, 1999-2006 (2001).
[57] Mundt, C., Licence, S., Shimizu, T., Melchers, F. & Martensson, I. L. Loss of precursor B cell expansion but not allelic exclusion in VpreB 1/VpreB2 doubledeficient mice. J Exp Med 193, 435-45 (2001).
[58] Su, Y. W. et al. Identification of a pre-BCR lacking surrogate light chain. J Exp Med 198, 1699-706 (2003).
[59] Pogue, S. L. & Goodnow, C. C. Gene dose-dependent maturation and receptor editing of B cells expressing antibody (Ig)G1 or IgM/IgG1 tail antigen receptors. J Exp Med 191, 1031-44 (2000).
[60] Zou, X. et al. Expression of a dromedary heavy chain-only antibody and B cell development in the mouse. J Immunol 175, 3769-79 (2005).
[61] Iglesias, A., Kopf, M., Williams, G. S., Buhler, B. & Kohler, G. Molecular requirements for the mu-induced light chain gene rearrangement in pre-B cells. Embo J 10, 2147-55 (1991).
[62] Shaffer, A. L. & Schlissel, M. S. A truncated heavy chain protein relieves the requirement for surrogate light chains in early B cell development. J Immunol 159, 1265-75 (1997).
[63] Sonoda, E. et al. B cell development under the condition of allelic inclusion. Immunity 6, 225-33 (1997).
[64] Eason D D, Litman R T, Luer C A, Kerr W, Litman G W. Expression of individual antibody genes occurs in an unusual system consisting of multiple independent loci. Eur J Immunol. 34:2551-8 (2004).
[65] Wagner S D, Gross G, Cook G P, Davies S L, Neuberger M S. Antibody expression from the core region of the human IgH locus reconstructed in transgenic mice using bacteriophage PI clones. Genomics. 35, 405-14 (1996).
[66] Xu J L, Davis M M. Diversity in the CDR3 region of V(H) is sufficient for most antibody specificities. Immunity 13, 37-45 (2000)
[67] De Genst E, Saerens D, Muyldermans S, Conrath K. Antibody repertoire development in camelids. Dev Comp Immunol. 30, 187-98 (2006).

SEQUENCE LISTING

```
<160> NUMBER OF SEQ ID NOS: 57

<210> SEQ ID NO 1
<211> LENGTH: 30
<212> TYPE: DNA
<213> ORGANISM: Artificial Sequence
<220> FEATURE:
<223> OTHER INFORMATION: PCR Primer

<400> SEQUENCE: 1
gcgggtaccg aatggtggca gggatggctc                                           30

<210> SEQ ID NO 2
<211> LENGTH: 30
<212> TYPE: DNA
<213> ORGANISM: Artificial Sequence
<220> FEATURE:
<223> OTHER INFORMATION: PCR Primer

<400> SEQUENCE: 2
cgcggtaccc tgcggtgtgg gacagagctg                                           30

<210> SEQ ID NO 3
<211> LENGTH: 35
<212> TYPE: DNA
<213> ORGANISM: Artificial Sequence
<220> FEATURE:
<223> OTHER INFORMATION: PCR Primer

<400> SEQUENCE: 3
cgcggtacca cggccacggc cacgctgctc gattc                                     35

<210> SEQ ID NO 4
<211> LENGTH: 26
<212> TYPE: DNA
<213> ORGANISM: Artificial Sequence
<220> FEATURE:
<223> OTHER INFORMATION: PCR Primer

<400> SEQUENCE: 4
ccagtcaata ctactcgcta agattc                                               26

<210> SEQ ID NO 5
```

```
<211> LENGTH: 24
<212> TYPE: DNA
<213> ORGANISM: Artificial Sequence
<220> FEATURE:
<223> OTHER INFORMATION: PCR Primer

<400> SEQUENCE: 5
cagtggtcca cagtttctca aagc                                              24

<210> SEQ ID NO 6
<211> LENGTH: 23
<212> TYPE: DNA
<213> ORGANISM: Artificial Sequence
<220> FEATURE:
<223> OTHER INFORMATION: PCR Primer

<400> SEQUENCE: 6
agactctcct gtgcagcctc tgg                                               23

<210> SEQ ID NO 7
<211> LENGTH: 23
<212> TYPE: DNA
<213> ORGANISM: Artificial Sequence
<220> FEATURE:
<223> OTHER INFORMATION: PCR Primer

<400> SEQUENCE: 7
cactcgacac aacatttgcg ctc                                               23

<210> SEQ ID NO 8
<211> LENGTH: 21
<212> TYPE: DNA
<213> ORGANISM: Artificial Sequence
<220> FEATURE:
<223> OTHER INFORMATION: PCR Primer

<400> SEQUENCE: 8
cactttggga ggcagctcag c                                                 21

<210> SEQ ID NO 9
<211> LENGTH: 21
<212> TYPE: DNA
<213> ORGANISM: Artificial Sequence
<220> FEATURE:
<223> OTHER INFORMATION: PCR Primer

<400> SEQUENCE: 9
ccagtgctgg aagtattcag c                                                 21

<210> SEQ ID NO 10
<211> LENGTH: 21
<212> TYPE: DNA
<213> ORGANISM: Artificial Sequence
<220> FEATURE:
<223> OTHER INFORMATION: PCR Primer

<400> SEQUENCE: 10
cagagatcga agtaccagta g                                                 21

<210> SEQ ID NO 11
<211> LENGTH: 21
<212> TYPE: DNA
<213> ORGANISM: Artificial Sequence
<220> FEATURE:
<223> OTHER INFORMATION: PCR Primer

<400> SEQUENCE: 11
```
ggccccagay atcaaaagca t                                              21

<210> SEQ ID NO 12
<211> LENGTH: 21
<212> TYPE: DNA
<213> ORGANISM: Artificial Sequence
<220> FEATURE:
<223> OTHER INFORMATION: PCR Primer

<400> SEQUENCE: 12
ggccccagta gtcaaagtag t                                              21

<210> SEQ ID NO 13
<211> LENGTH: 21
<212> TYPE: DNA
<213> ORGANISM: Artificial Sequence
<220> FEATURE:
<223> OTHER INFORMATION: PCR Primer

<400> SEQUENCE: 13
cccaggrgtc gaaccagttg t                                              21

<210> SEQ ID NO 14
<211> LENGTH: 22
<212> TYPE: DNA
<213> ORGANISM: Artificial Sequence
<220> FEATURE:
<223> OTHER INFORMATION: PCR Primer

<400> SEQUENCE: 14
ccagaacgtc catrymgtag ta                                             22

<210> SEQ ID NO 15
<211> LENGTH: 39
<212> TYPE: DNA
<213> ORGANISM: Artificial Sequence
<220> FEATURE:
<223> OTHER INFORMATION: PCR Primer

<400> SEQUENCE: 15
aatctgggca gcggccgcct cgacacaaca tttgcgctc                           39

<210> SEQ ID NO 16
<211> LENGTH: 39
<212> TYPE: DNA
<213> ORGANISM: Artificial Sequence
<220> FEATURE:
<223> OTHER INFORMATION: PCR Primer

<400> SEQUENCE: 16
tgggacgaag acggccgctt tgggaggcag ctcggcaat                           39

<210> SEQ ID NO 17
<211> LENGTH: 124
<212> TYPE: DNA
<213> ORGANISM: Artificial Sequence
<220> FEATURE:
<223> OTHER INFORMATION: Synthetic Sequence

<400> SEQUENCE: 17
gacacggccg tttattactg tgcgacagat tacgatattt tgactggtta ttataacgta    60
ctttgactac tggggccagg gaaccctggt caccgtctcc tcagagcgca aatgttgtgt   120
cgag                                                                124

<210> SEQ ID NO 18
<211> LENGTH: 123
<212> TYPE: DNA
<213> ORGANISM: Artificial Sequence
<220> FEATURE:
<223> OTHER INFORMATION: Synthetic Sequence

<400> SEQUENCE: 18

```
gacacggccg tttattactg tgcgacagat tgggggttcg gggagttatt atagctacta      60
ctttgactac tggggccagg gaaccctggt caccgtctcc tcagagcgca aatgttgtgt     120
gag                                                                    123
```

<210> SEQ ID NO 19
<211> LENGTH: 104
<212> TYPE: DNA
<213> ORGANISM: Artificial Sequence
<220> FEATURE:
<223> OTHER INFORMATION: Synthetic Sequence

<400> SEQUENCE: 19

```
gacacggccg tttattactg tgcgacaggc tggtactggg gtttgactac tggggccagg      60
gaaccctggt caccgtctcc tcagagcgca aatgttgtgt cgag                      104
```

<210> SEQ ID NO 20
<211> LENGTH: 122
<212> TYPE: DNA
<213> ORGANISM: Artificial Sequence
<220> FEATURE:
<223> OTHER INFORMATION: Synthetic Sequence

<400> SEQUENCE: 20

```
gacacggccg tttattactg tgcgacagat tacgatattt gactggttat cttgatgctt      60
ttgatatctg gggccaaggg acaatggtca ccgtctcttc agagcgcaaa tgttgtgtcg     120
ag                                                                    122
```

<210> SEQ ID NO 21
<211> LENGTH: 120
<212> TYPE: DNA
<213> ORGANISM: Artificial Sequence
<220> FEATURE:
<223> OTHER INFORMATION: Synthetic Sequence

<400> SEQUENCE: 21

```
gacacggccg tctattactg taatgcagta gccgggtata gcagcagctg gtacccctttt      60 gactactggg gccagggaac cctggtcacc gtctcctcag agcgcaaatg ttgtgtcgag     120
```

<210> SEQ ID NO 22
<211> LENGTH: 113
<212> TYPE: DNA
<213> ORGANISM: Artificial Sequence
<220> FEATURE:
<223> OTHER INFORMATION: Synthetic Sequence

<400> SEQUENCE: 22

```
gacacggccg tctattactg taatccgtat tactatggtt cggggagtcc tttgactact      60
ggggccaggg aaccctggtc accgtctcct cagagcgcaa atgttgtgtc gag             113
```

<210> SEQ ID NO 23
<211> LENGTH: 119
<212> TYPE: DNA
<213> ORGANISM: Artificial Sequence

```
<220> FEATURE:
<223> OTHER INFORMATION: Synthetic Sequence

<400> SEQUENCE: 23
gacacggccg tctattactg taatgatggg gtatagcagt ggctggctac tggtacttcg      60
atctctgggg ccgtggcacc ctggtcactg tctcctcaga gcgcaaatgt tgtgtcgag       119

<210> SEQ ID NO 24
<211> LENGTH: 123
<212> TYPE: DNA
<213> ORGANISM: Artificial Sequence
<220> FEATURE:
<223> OTHER INFORMATION: Synthetic Sequence

<400> SEQUENCE: 24
gacacggccg tctattactg taatgcagag ggtatagcag tggctggtac gtggggagac      60
tttgactact ggggccaggg aaccctggtc accgtctcct cagagcgcaa atgttgtgtc     120
gag                                                                  123

<210> SEQ ID NO 25
<211> LENGTH: 115
<212> TYPE: DNA
<213> ORGANISM: Artificial Sequence
<220> FEATURE:
<223> OTHER INFORMATION: Synthetic Sequence

<400> SEQUENCE: 25
gacacggccg tttattactg tgcgaccgta tagcagtggc tgggttgaat acttccagca      60
ctggggccag ggcaccctgg tcaccgtctc ctcagagcgc aaatgttgtg tcgag          115

<210> SEQ ID NO 26
<211> LENGTH: 120
<212> TYPE: DNA
<213> ORGANISM: Artificial Sequence
<220> FEATURE:
<223> OTHER INFORMATION: Synthetic Sequence

<400> SEQUENCE: 26
gacacggccg tttattactg tgcgacagcc tgtattacta tggttcgggg agttaggatg      60
gacgtctggg gccaagggac cacggtcacc gtctcctcag agcgcaaatg ttgtgtcgag    120

<210> SEQ ID NO 27
<211> LENGTH: 59
<212> TYPE: PRT
<213> ORGANISM: Artificial Sequence
<220> FEATURE:
<223> OTHER INFORMATION: Synthetic Sequence

<400> SEQUENCE: 27

Arg Leu Ser Cys Ala Ala Ser Gly Phe Thr Leu Asp Tyr Tyr Ala Ile
1               5                  10                  15

Gly Trp Phe Arg Gln Ala Glu Gly Lys Glu Arg Glu Gly Val Ser Cys
            20                  25                  30

Ile Ser Ser Ser Asp Gly Ser Thr Tyr Tyr Ala Asp Ser Val Lys Gly
        35                  40                  45

Arg Phe Thr Ile Ser Arg Asp Asn Ala Lys Asn
    50                  55

<210> SEQ ID NO 28
<211> LENGTH: 59
<212> TYPE: PRT
```

<213> ORGANISM: Artificial Sequence
<220> FEATURE:
<223> OTHER INFORMATION: Synthetic Sequence

<400> SEQUENCE: 28

Arg Leu Ser Cys Ala Ala Ser Gly Phe Thr Leu Asp Tyr Tyr Ala Ile
1               5                   10                  15

Gly Trp Phe Arg Gln Ala Glu Gly Lys Glu Arg Glu Gly Val Ser Cys
            20                  25                  30

Ile Ser Ser Ser Asp Gly Ser Thr Tyr Tyr Ala Asp Ser Val Lys Gly
        35                  40                  45

Arg Phe Thr Ile Ser Arg Asp Asn Ala Lys Asn
    50                  55

<210> SEQ ID NO 29
<211> LENGTH: 59
<212> TYPE: PRT
<213> ORGANISM: Artificial Sequence
<220> FEATURE:
<223> OTHER INFORMATION: Synthetic Sequence

<400> SEQUENCE: 29

Arg Leu Ser Cys Ala Ala Ser Gly Phe Thr Leu Asp Tyr Tyr Val Ile
1               5                   10                  15

Gly Trp Phe Arg Gln Ala Glu Gly Lys Glu Arg Glu Gly Val Ser Cys
            20                  25                  30

Ile Ser Ser Ser Asp Gly Ser Thr Tyr Tyr Ala Asp Ser Val Lys Gly
        35                  40                  45

Arg Phe Thr Ile Ser Arg Asp Asn Ala Lys Asn
    50                  55

<210> SEQ ID NO 30
<211> LENGTH: 59
<212> TYPE: PRT
<213> ORGANISM: Artificial Sequence
<220> FEATURE:
<223> OTHER INFORMATION: Synthetic Sequence

<400> SEQUENCE: 30

Arg Leu Ser Cys Ala Ala Ser Gly Phe Thr Leu Asp Tyr Tyr Ala Ile
1               5                   10                  15

Gly Trp Phe Arg Gln Ala Glu Gly Lys Glu Arg Glu Gly Val Ser Cys
            20                  25                  30

Ile Ser Ser Ser Asp Gly Ser Thr Tyr Tyr Gly Asp Ser Val Lys Gly
        35                  40                  45

Arg Phe Thr Ile Ser Arg Asp Lys Ala Lys Asn
    50                  55

<210> SEQ ID NO 31
<211> LENGTH: 58
<212> TYPE: PRT
<213> ORGANISM: Artificial Sequence
<220> FEATURE:
<223> OTHER INFORMATION: Synthetic Sequence

<400> SEQUENCE: 31

Arg Leu Ser Cys Ala Ala Ser Gly Ser Ile Phe Ser Ile Asn Ala Met
1               5                   10                  15

Gly Trp Tyr Arg Gln Ala Pro Gly Lys Gln Arg Glu Leu Val Ala Ala
            20                  25                  30

Ile Thr Ser Gly Gly Ser Thr Asn Tyr Ala Asp Ser Val Lys Gly Arg

Phe Thr Ile Ser Arg Asp Asn Ala Lys Asn
    50                  55

<210> SEQ ID NO 32
<211> LENGTH: 57
<212> TYPE: PRT
<213> ORGANISM: Artificial Sequence
<220> FEATURE:
<223> OTHER INFORMATION: Synthetic Sequence

<400> SEQUENCE: 32

Arg Leu Ser Cys Ala Ala Ser Gly Ser Ile Phe Ser Ile Asn Ala Met
1               5                   10                  15

Gly Trp Tyr Arg Gln Ala Pro Gly Lys Gln Arg Glu Leu Val Ala Ala
            20                  25                  30

Ile Thr Ser Gly Gly Ser Thr Lys Tyr Ala Asp Ser Val Lys Gly Arg
        35                  40                  45

Phe Thr Ile Ser Arg Asp Asn Ala Lys
    50                  55

<210> SEQ ID NO 33
<211> LENGTH: 58
<212> TYPE: PRT
<213> ORGANISM: Artificial Sequence
<220> FEATURE:
<223> OTHER INFORMATION: Synthetic Sequence

<400> SEQUENCE: 33

Arg Leu Ser Cys Ala Ala Ser Gly Ser Ile Phe Ser Ile Asn Val Met
1               5                   10                  15

Gly Trp Tyr Arg Gln Ala Pro Gly Lys Gln Arg Glu Leu Val Ala Gly
            20                  25                  30

Val Thr Ser Gly Gly Ser Thr Ser Tyr Ala Asp Ser Val Lys Gly Arg
        35                  40                  45

Phe Thr Ile Ser Arg Asp Asn Ala Lys Asn
    50                  55

<210> SEQ ID NO 34
<211> LENGTH: 58
<212> TYPE: PRT
<213> ORGANISM: Artificial Sequence
<220> FEATURE:
<223> OTHER INFORMATION: Synthetic Sequence

<400> SEQUENCE: 34

Arg Leu Ser Cys Ala Ala Ser Gly Ser Ile Phe Ser Ile Asn Ala Met
1               5                   10                  15

Gly Trp Tyr Arg Gln Ala Pro Gly Lys Gln Arg Glu Leu Val Ala Pro
            20                  25                  30

Ile Thr Ser Gly Gly Ser Thr Asn Tyr Ala Asp Ser Val Lys Gly Arg
        35                  40                  45

Phe Thr Ile Ser Arg Asp Asn Ala Lys Asn
    50                  55

<210> SEQ ID NO 35
<211> LENGTH: 78
<212> TYPE: PRT
<213> ORGANISM: Artificial Sequence
<220> FEATURE:
<223> OTHER INFORMATION: Synthetic Sequence

```
<400> SEQUENCE: 35

Arg Leu Ser Cys Ala Ala Ser Gly Ser Ile Phe Ser Ile Asn Ala Met
1               5                   10                  15

Gly Trp Tyr Arg Gln Ala Pro Gly Lys Gln Arg Glu Leu Val Ala Ala
            20                  25                  30

Ile Thr Ser Gly Gly Ser Thr Asn Tyr Ala Asp Ser Val Lys Gly Arg
        35                  40                  45

Phe Thr Ile Ser Arg Asp Asn Ala Lys Asn Thr Val Tyr Leu Gln Met
    50                  55                  60

Asn Ser Leu Lys Pro Glu Asp Thr Ala Val Tyr Tyr Cys Asn
65                  70                  75

<210> SEQ ID NO 36
<211> LENGTH: 108
<212> TYPE: PRT
<213> ORGANISM: Artificial Sequence
<220> FEATURE:
<223> OTHER INFORMATION: Synthetic Sequence

<400> SEQUENCE: 36

Arg Leu Ser Cys Ala Ala Ser Gly Ser Ile Phe Ser Ile Asn Ala Met
1               5                   10                  15

Gly Trp Tyr Arg Gln Ala Pro Gly Lys Gln Arg Glu Leu Val Ala Ala
            20                  25                  30

Ile Thr Ser Gly Gly Ser Thr Asn Tyr Ala Asp Ser Val Lys Gly Arg
        35                  40                  45

Phe Thr Ile Ser Arg Asp Asn Ala Lys Asn Thr Val Tyr Leu Gln Met
    50                  55                  60

Asn Ser Leu Lys Pro Glu Asp Thr Ala Val Tyr Tyr Cys Asn Ala Lys
65                  70                  75                  80

Gly Pro Ile Thr Met Val Arg Val His Tyr Trp Gly Gln Gly Thr
                85                  90                  95

Leu Val Thr Val Ser Ser Glu Arg Lys Cys Cys Val
            100                 105

<210> SEQ ID NO 37
<211> LENGTH: 108
<212> TYPE: PRT
<213> ORGANISM: Artificial Sequence
<220> FEATURE:
<223> OTHER INFORMATION: Synthetic Sequence

<400> SEQUENCE: 37

Arg Leu Ser Cys Ala Ala Ser Gly Ser Ile Phe Ser Ile Asn Ala Met
1               5                   10                  15

Gly Trp Tyr Arg Gln Ala Pro Gly Lys Gln Arg Glu Leu Val Ala Ala
            20                  25                  30

Ile Thr Ser Gly Gly Ser Thr Asn Tyr Ala Asp Ser Val Lys Gly Arg
        35                  40                  45

Phe Thr Ile Ser Arg Asp Asn Ala Lys Asn Thr Val Tyr Leu Gln Met
    50                  55                  60

Asn Ser Leu Lys Pro Glu Asp Thr Ala Val Tyr Tyr Cys Asn Ala Lys
65                  70                  75                  80

Gly Pro Ile Thr Met Ile Arg Val His His Trp Gly Gln Gly Thr
                85                  90                  95

Leu Val Thr Val Ser Ser Glu Arg Lys Cys Cys Val
            100                 105
```

-continued

```
<210> SEQ ID NO 38
<211> LENGTH: 108
<212> TYPE: PRT
<213> ORGANISM: Artificial Sequence
<220> FEATURE:
<223> OTHER INFORMATION: Synthetic Sequence

<400> SEQUENCE: 38

Arg Leu Ser Cys Ala Ala Ser Gly Ser Ile Phe Ser Ile Asn Ala Met
1               5                   10                  15

Gly Trp Tyr Arg Gln Ala Pro Gly Lys Gln Arg Glu Leu Val Ala Ala
            20                  25                  30

Ile Thr Ser Gly Gly Ser Thr Asn Tyr Ala Asp Ser Val Lys Gly Arg
        35                  40                  45

Phe Thr Ile Ser Arg Asp Asn Ala Lys Asn Thr Val Tyr Leu Gln Met
    50                  55                  60

Asn Ser Leu Lys Pro Glu Asp Thr Ala Val Tyr Tyr Cys Asn Ala Arg
65                  70                  75                  80

Gly Pro Ile Thr Val Val Arg Gly Val His Tyr Trp Gly Gln Gly Thr
                85                  90                  95

Leu Val Thr Val Ser Ser Glu Arg Lys Cys Cys Val
            100                 105

<210> SEQ ID NO 39
<211> LENGTH: 108
<212> TYPE: PRT
<213> ORGANISM: Artificial Sequence
<220> FEATURE:
<223> OTHER INFORMATION: Synthetic Sequence

<400> SEQUENCE: 39

Arg Leu Ser Cys Ala Ala Ser Gly Ser Ile Phe Ser Ile Asn Ala Met
1               5                   10                  15

Gly Trp Tyr Arg Gln Ala Pro Gly Lys Gln Arg Glu Leu Val Ala Ala
            20                  25                  30

Ile Thr Ser Gly Gly Ser Thr Asn Tyr Ala Asp Ser Val Lys Gly Arg
        35                  40                  45

Phe Thr Ile Ser Arg Asp Lys Ala Lys Asn Thr Val Tyr Leu Gln Met
    50                  55                  60

Asn Ser Leu Lys Pro Glu Asp Ser Ala Val Tyr Tyr Cys Asn Ala Arg
65                  70                  75                  80

Thr Pro Ile Thr Met Val Arg Gly Val Asp Tyr Trp Gly Arg Gly Thr
                85                  90                  95

Leu Val Thr Val Ser Ser Glu Arg Lys Cys Cys Val
            100                 105

<210> SEQ ID NO 40
<211> LENGTH: 108
<212> TYPE: PRT
<213> ORGANISM: Artificial Sequence
<220> FEATURE:
<223> OTHER INFORMATION: Synthetic Sequence

<400> SEQUENCE: 40

Arg Leu Ser Cys Ala Ala Ser Gly Ser Ile Phe Ser Ile Asn Ala Met
1               5                   10                  15

Gly Trp Tyr Arg Gln Ala Pro Gly Lys Gln Arg Glu Leu Val Ala Ala
            20                  25                  30

Ile Thr Ser Gly Gly Ser Thr Asn His Ala Asp Ser Val Lys Gly Arg
```

```
                35                  40                  45
Phe Thr Ile Ser Arg Asp Asn Ala Lys Asn Thr Val Tyr Leu Gln Met
 50                  55                  60

Asn Ser Leu Lys Pro Glu Asp Thr Ala Val Tyr Tyr Cys Asn Ala Glu
 65                  70                  75                  80

Gly Pro Ile Thr Lys Val Arg Gly Val Ser Tyr Trp Gly Gln Gly Thr
                 85                  90                  95

Leu Val Thr Val Ser Ser Glu Arg Lys Cys Cys Val
                100                 105
```

<210> SEQ ID NO 41
<211> LENGTH: 105
<212> TYPE: PRT
<213> ORGANISM: Artificial Sequence
<220> FEATURE:
<223> OTHER INFORMATION: Synthetic Sequence

<400> SEQUENCE: 41

```
Arg Leu Ser Cys Ala Ala Ser Gly Ser Ile Phe Ser Ile Asn Ala Met
 1               5                  10                  15

Gly Trp Tyr Arg Gln Ala Pro Gly Lys Gln Arg Glu Leu Val Ala Ala
                20                  25                  30

Ile Thr Ser Gly Gly Ser Thr Asn Tyr Ala Asp Ser Val Lys Gly Arg
                35                  40                  45

Phe Thr Ile Ser Arg Asp Asn Ala Lys Asn Thr Val Tyr Leu Gln Met
 50                  55                  60

Asn Ser Leu Lys Pro Glu Asp Thr Ala Val Tyr Tyr Cys Asn Ala Glu
 65                  70                  75                  80

Arg Ala Gly Asp Pro Phe Asp Tyr Trp Gly Gln Gly Thr Leu Val Thr
                 85                  90                  95

Val Ser Ser Glu Arg Lys Cys Cys Val
                100                 105
```

<210> SEQ ID NO 42
<211> LENGTH: 108
<212> TYPE: PRT
<213> ORGANISM: Artificial Sequence
<220> FEATURE:
<223> OTHER INFORMATION: Synthetic Sequence

<400> SEQUENCE: 42

```
Arg Leu Ser Cys Ala Ala Ser Gly Ser Ile Phe Ser Ile Asn Ala Met
 1               5                  10                  15

Gly Trp Tyr Arg Gln Ala Pro Gly Lys Gln Arg Glu Leu Val Ala Ala
                20                  25                  30

Ile Thr Ser Gly Gly Ser Thr Asn Tyr Ala Asp Ser Val Lys Gly Arg
                35                  40                  45

Phe Thr Ile Ser Arg Asp Asn Ala Lys Asn Thr Val Tyr Leu Gln Met
 50                  55                  60

Asn Ser Leu Lys Pro Glu Asp Thr Ala Val Tyr Tyr Cys Gly Val Leu
 65                  70                  75                  80

Trp Phe Gly Glu Leu Ser Asp Trp Phe Asp Pro Trp Gly Gln Gly Thr
                 85                  90                  95

Leu Val Thr Val Ser Ser Glu Arg Lys Cys Cys Val
                100                 105
```

<210> SEQ ID NO 43
<211> LENGTH: 107

```
<212> TYPE: PRT
<213> ORGANISM: Artificial Sequence
<220> FEATURE:
<223> OTHER INFORMATION: Synthetic Sequence

<400> SEQUENCE: 43

Arg Leu Ser Cys Ala Ala Ser Gly Ser Ile Phe Ser Ile Asn Ala Met
1               5                   10                  15

Gly Trp Tyr Arg Gln Ala Pro Gly Lys Gln Arg Glu Leu Val Ala Ala
            20                  25                  30

Ile Thr Ser Gly Gly Ser Thr Asn Tyr Ala Asp Ser Val Lys Gly Arg
        35                  40                  45

Phe Thr Ile Ser Arg Asp Asn Ala Lys Asn Thr Val Tyr Leu Gln Met
50                  55                  60

Asn Ser Leu Lys Pro Glu Asp Thr Ala Val Tyr Tyr Cys Asn Ala Asp
65                  70                  75                  80

Cys Trp Gly Ser Arg Trp Tyr Phe Asp Leu Trp Gly Arg Gly Thr Leu
                85                  90                  95

Val Thr Val Ser Ser Glu Arg Lys Cys Cys Val
            100                 105

<210> SEQ ID NO 44
<211> LENGTH: 111
<212> TYPE: PRT
<213> ORGANISM: Artificial Sequence
<220> FEATURE:
<223> OTHER INFORMATION: Synthetic Sequence

<400> SEQUENCE: 44

Arg Leu Ser Cys Ala Ala Ser Gly Ser Ile Phe Ser Ile Asn Ala Met
1               5                   10                  15

Gly Trp Tyr Arg Gln Ala Pro Gly Lys Gln Arg Glu Leu Val Ala Ala
            20                  25                  30

Ile Thr Ser Gly Gly Ser Thr Asn Tyr Ala Asp Ser Val Lys Gly Arg
        35                  40                  45

Phe Thr Ile Ser Arg Asp Asn Ala Lys Asn Thr Val Tyr Leu Gln Met
50                  55                  60

Asn Ser Leu Lys Pro Glu Asp Thr Ala Val Tyr Tyr Cys Asn Ala Asp
65                  70                  75                  80

Thr Ser Pro Pro Arg Tyr Phe Asp Trp Leu Pro Phe Asp Tyr Trp Gly
                85                  90                  95

Gln Gly Thr Leu Val Thr Val Ser Ser Glu Arg Lys Cys Cys Val
            100                 105                 110

<210> SEQ ID NO 45
<211> LENGTH: 112
<212> TYPE: PRT
<213> ORGANISM: Artificial Sequence
<220> FEATURE:
<223> OTHER INFORMATION: Synthetic Sequence

<400> SEQUENCE: 45

Arg Leu Ser Cys Ala Ala Ser Gly Ser Ile Phe Ser Ser Asn Ala Met
1               5                   10                  15

Gly Trp Ser Arg Gln Ala Pro Gly Lys Gln Arg Glu Leu Val Ala Ala
            20                  25                  30

Ile Thr Ser Gly Gly Ser Thr Asn Tyr Ala Asp Ser Val Lys Gly Arg
        35                  40                  45

Phe Thr Ile Ser Arg Asp Asn Ala Lys Asn Thr Val His Leu Gln Met
```

```
                 50                  55                  60

Asn Ser Leu Lys Pro Glu Asp Thr Ala Val Tyr Tyr Cys Asn Ala Gly
 65                  70                  75                  80

Asn Thr Met Val Arg Gly Val Ile Ile Lys Tyr Arg Phe Asp Tyr Trp
                     85                  90                  95

Gly Gln Gly Thr Leu Val Thr Val Ser Ser Glu Arg Lys Cys Cys Val
                100                 105                 110

<210> SEQ ID NO 46
<211> LENGTH: 115
<212> TYPE: PRT
<213> ORGANISM: Artificial Sequence
<220> FEATURE:
<223> OTHER INFORMATION: Synthetic Sequence

<400> SEQUENCE: 46

Arg Leu Ser Cys Ala Ala Ser Gly Ser Ile Phe Ser Ile Asn Ala Met
 1               5                  10                  15

Gly Trp Asp Leu Gln Ala Pro Arg Lys Gln Arg Glu Leu Val Ala Ala
                 20                  25                  30

Ile Thr Ser Gly Gly Ser Thr Asn Tyr Ala Asp Ser Val Lys Gly Arg
             35                  40                  45

Phe Thr Ile Ser Arg Asp Asn Ala Lys Asn Thr Val Tyr Leu Gln Met
 50                  55                  60

Asn Ser Leu Lys Pro Glu Asp Thr Ala Val Tyr Tyr Cys Asn Ala Glu
 65                  70                  75                  80

Lys Pro Val Leu Leu Trp Phe Gly Glu Leu Leu Lys Gly Thr Tyr Phe
                     85                  90                  95

Asp Tyr Trp Gly Gln Gly Thr Leu Val Thr Val Ser Ser Glu Arg Lys
                100                 105                 110

Cys Cys Val
        115

<210> SEQ ID NO 47
<211> LENGTH: 105
<212> TYPE: PRT
<213> ORGANISM: Artificial Sequence
<220> FEATURE:
<223> OTHER INFORMATION: Synthetic Sequence

<400> SEQUENCE: 47

Arg Leu Ser Cys Ala Ala Ser Gly Ser Ile Phe Ser Ile Asn Ala Met
 1               5                  10                  15

Gly Trp Tyr Arg Gln Ala Pro Gly Lys Gln Arg Glu Leu Val Ala Ala
                 20                  25                  30

Ile Thr Ser Gly Gly Ser Thr Asn Tyr Ala Asp Ser Val Lys Gly Arg
             35                  40                  45

Phe Thr Ile Ser Arg Asp Asn Ala Lys Asn Thr Val Tyr Leu Gln Met
 50                  55                  60

Asn Ser Leu Lys Pro Glu Asp Thr Ala Val Tyr Tyr Cys Asn Ala Arg
 65                  70                  75                  80

Ser Ser Ser Trp Ile Phe Asp Tyr Trp Gly Gln Gly Thr Leu Val Thr
                     85                  90                  95

Val Ser Ser Glu Arg Lys Cys Cys Val
                100                 105

<210> SEQ ID NO 48
<211> LENGTH: 110
```

```
<212> TYPE: PRT
<213> ORGANISM: Artificial Sequence
<220> FEATURE:
<223> OTHER INFORMATION: Synthetic Sequence

<400> SEQUENCE: 48

Arg Leu Ser Cys Ala Ala Ser Gly Ser Ile Phe Ser Ile Asn Ala Met
1               5                   10                  15

Gly Trp Tyr Arg Gln Ala Pro Gly Lys Gln Arg Glu Leu Val Ala Ala
            20                  25                  30

Ile Thr Ser Gly Gly Ser Thr Asn Tyr Ala Asp Ser Val Lys Gly Arg
        35                  40                  45

Phe Thr Ile Ser Arg Asp Asn Ala Lys Asn Thr Val Tyr Leu Gln Met
 50                  55                  60

Asn Ser Leu Lys Pro Glu Asp Thr Ala Val Tyr Tyr Cys Asn Ala Ala
65                  70                  75                  80

Arg Thr Pro Ile Thr Val Val Arg Gly Phe Asp Tyr Trp Gly Gln Gly
                85                  90                  95

Thr Leu Val Thr Val Ser Ser Glu Glu Leu Lys Thr Pro Leu
            100                 105                 110

<210> SEQ ID NO 49
<211> LENGTH: 109
<212> TYPE: PRT
<213> ORGANISM: Artificial Sequence
<220> FEATURE:
<223> OTHER INFORMATION: Synthetic Sequence

<400> SEQUENCE: 49

Arg Leu Ser Cys Ala Ala Ser Gly Ser Ile Phe Ser Ile Asn Ala Met
1               5                   10                  15

Gly Trp Tyr Arg Gln Ala Pro Gly Lys Gln Arg Glu Leu Val Ala Ala
            20                  25                  30

Ile Thr Ser Gly Gly Ser Thr Asn Tyr Val Asp Ser Val Lys Gly Arg
        35                  40                  45

Phe Thr Ile Ser Arg Asp Asn Ala Lys Asn Thr Val Tyr Leu Gln Met
 50                  55                  60

Asn Ser Leu Lys Pro Glu Asp Thr Ala Val Tyr Tyr Cys Asn Ala Asp
65                  70                  75                  80

Ser Arg Ser Ser Ser Gly Trp Tyr Ser Leu Asp Tyr Trp Gly Gln Gly
                85                  90                  95

Thr Leu Val Thr Val Ser Ser Val Ile Ala Glu Leu Pro
            100                 105

<210> SEQ ID NO 50
<211> LENGTH: 105
<212> TYPE: PRT
<213> ORGANISM: Artificial Sequence
<220> FEATURE:
<223> OTHER INFORMATION: Synthetic Sequence

<400> SEQUENCE: 50

Arg Leu Thr Cys Ala Ala Ser Gly Ser Ile Phe Ser Ile Ile Gly Met
1               5                   10                  15

Gly Trp Tyr Arg Gln Ala Pro Gly Lys Gln Arg Glu Leu Val Ala Thr
            20                  25                  30

Ile Thr Ser Gly Asp Asn Thr Asn Tyr Ala Asp Ser Val Lys Gly Arg
        35                  40                  45

Phe Thr Ile Ser Arg Asp Asn Ala Lys Asn Thr Val Tyr Leu Gln Met
```

```
                      50                  55                  60

Asn Ser Leu Lys Pro Glu Asp Thr Ala Val Tyr Tyr Cys Asn Ala Leu
 65                  70                  75                  80

Asp Ser Ser Gly Trp Ser Asp Tyr Trp Gly Gln Gly Thr Leu Val Thr
                     85                  90                  95

Val Ser Ser Val Ile Ala Glu Leu Pro
                100                 105

<210> SEQ ID NO 51
<211> LENGTH: 105
<212> TYPE: PRT
<213> ORGANISM: Artificial Sequence
<220> FEATURE:
<223> OTHER INFORMATION: Synthetic Sequence

<400> SEQUENCE: 51

Arg Leu Ser Cys Ala Ala Ser Gly Ser Ile Phe Ser Ile Ile Gly Met
 1               5                  10                  15

Gly Trp Tyr Arg Gln Ala Pro Gly Lys Gln Arg Glu Leu Val Ala Ala
                20                  25                  30

Ile Thr Ser Gly Gly Ser Thr Asn Tyr Ala Asp Ser Val Lys Gly Arg
            35                  40                  45

Phe Thr Ile Ser Arg Asp Asn Ala Met Asn Thr Val Tyr Leu Gln Met
        50                  55                  60

Asn Ser Leu Lys Pro Glu Asp Thr Ala Val Tyr Tyr Cys Asn Ala Leu
 65                  70                  75                  80

Asp Ser Ser Gly Trp Ser Asp Tyr Trp Gly Gln Gly Thr Leu Val Thr
                     85                  90                  95

Val Ser Ser Val Ile Ala Glu Leu Pro
                100                 105

<210> SEQ ID NO 52
<211> LENGTH: 399
<212> TYPE: DNA
<213> ORGANISM: Artificial Sequence
<220> FEATURE:
<223> OTHER INFORMATION: Synthetic Sequence

<400> SEQUENCE: 52
gacacggccg tgtagtatct gtaaggcaga tggggtagta ctatggttcg gggagtccac      60
cactgcggct agaggggcca gggaacactg gtcgcggtgt catcagcctc accaagggc     120 ccatcggtct tccccctggc gccctgctcc aggagcacct ccgagagcac agcggccctg    180
ggctgcctgg tcaaggacta cggccccgaa ccggtgtcgt ggaactcagg cgctctgacc    240
agcggcgtgc acaccttccc agctgtccta cagtcctcag gactctactc cctcagcagc    300
gtggtgaccg tgccctccag caacttcggc acccagacct acacctgcaa cgtagatcac    360
aaagcccagc aacaccaaga gcgcaaatgt tgtgtcgag                           399

<210> SEQ ID NO 53
<211> LENGTH: 347
<212> TYPE: DNA
<213> ORGANISM: Artificial Sequence
<220> FEATURE:
<223> OTHER INFORMATION: Synthetic Sequence

<400> SEQUENCE: 53
gacattccca cttcgatctc tggggccgtg caccctggt cactgtctcc tcagcctcca      60
ccaagggccc atcggtcttc cccctggcgc cctgctccag gagcacctcc gagagcacag    120
```

```
cggccctggg ctgcctggtc aaggactacg gccccgaacc ggtgtcgtgg aactcaggcg    180
ctctgaccag cggcgtgcac accttcccag ctgtcctaca gtcctcagga ctctactccc    240
tcagcagcgt ggtgaccgtg ccctccagca acttcggcac ccagacctac acctgcaacg    300
tagatcacaa agcccagcaa caccaagagc gcaaatgttg tgtcgag                  347
```

<210> SEQ ID NO 54
<211> LENGTH: 389
<212> TYPE: DNA
<213> ORGANISM: Artificial Sequence
<220> FEATURE:
<223> OTHER INFORMATION: Synthetic Sequence

<400> SEQUENCE: 54

```
gacacggccg tctattactg taatgccact acgatatttt gactggttat tatagacgct     60
actggggcca gggaaccctg gtcaccgtct cctcagcctc cgccaagggc ccatcggtct    120
tccccctggc gccctgctcc aggagcacct ccgagagcac agcggccctg ggctgcctgg    180
tcaaggacta cggccccgaa ccggtgtcgt ggaactcagg cgctctgacc agcggcgtgc    240
acaccttccc agctgtccta cagtcctcag gactctactc cctcagcagc gtggtgaccg    300
tgccctccag caacttcggc acccagacct acacctgcaa cgtagatcac aaagcccagc    360
aacaccaaga gcgcaaatgt tgtgtcgag                                      389
```

<210> SEQ ID NO 55
<211> LENGTH: 375
<212> TYPE: DNA
<213> ORGANISM: Artificial Sequence
<220> FEATURE:
<223> OTHER INFORMATION: Synthetic Sequence

<400> SEQUENCE: 55

```
gacacggccg tccaatcgga tacagctatg gttacgtact ttgactactg gggccaggga     60
accctggtca ccgtctcctc agcctccacc aagggcccat cggtcttccc cctggcgccc    120
tgctccagga gcacctccga gagcacagcg gccctgggct gcctggtcaa ggactacggc    180
cccgaaccgg tgtcgtggaa ctcaggcgct ctgaccagcg gcgtgcacac cttcccagct    240
gtcctacagt cctcaggact ctactccctc agcagcgtgg tgaccgtgcc ctccagcaac    300
ttcggcaccc agacctacac ctgcaacgta gatcacaaag cccagcaaca ccaagagcgc    360
aaatgttgtg tcgag                                                     375
```

<210> SEQ ID NO 56
<211> LENGTH: 412
<212> TYPE: DNA
<213> ORGANISM: Artificial Sequence
<220> FEATURE:
<223> OTHER INFORMATION: Synthetic Sequence

<400> SEQUENCE: 56

```
gacacggccg tctattactg taatgcagat gtattactat ggttcgggga gcctatagcc     60
ttactactac tacggtatgg acgtctgggg ccaaggggaca ctggtcaccg tctcctcagc    120
ctccaccaag ggcccatcgg tcttcccccct ggcgccctgc tccaggagca cctccgagag    180
cacagcggcc ctgggctgcc tggtcaagga ctacggcccc gaaccggtgt cgtggaactc    240
aggcgctctg accagcggcg tgcacacctt cccagctgtc ctacagtcct caggactcta    300
ctccctcagc agcgtggtga ccgtgccctc agcaacttc ggcacccaga cctacacctg    360
```

```
caacgtagat cacaaagccc agcaacacca agagcgcaaa tgttgtgtcg ag            412
```

<210> SEQ ID NO 57
<211> LENGTH: 16
<212> TYPE: DNA
<213> ORGANISM: Artificial Sequence
<220> FEATURE:
<223> OTHER INFORMATION: Synthetic Sequence

<400> SEQUENCE: 57

```
ggtggacaag acagtt                                                    16
```

The invention claimed is:

1. A method for increasing the diversity of $V_H$ heavy chain-only antibodies in a transgenic non-human mammal comprising the steps of
   a) providing a transgenic non-human mammal whose genome comprises more than one heterologous $V_H$ heavy chain locus, wherein each $V_H$ heavy chain locus comprises naturally occurring $V_H$ gene segments of human origin, D gene segments, and J gene segments, and a gene segment encoding a heavy chain constant region which, when expressed, does not include a functional $C_H1$ domain and
   b) expressing a $V_H$ heavy chain-only antibody from at least one of said loci in B-cells,
wherein said heterologous $V_H$ heavy chain loci are present on the same or different chromosomes, and the expression of a heterologous $V_H$ locus is determined by allelic exclusion.

2. The method of claim 1, wherein each locus comprises only one V gene segment.

3. The method of claim 1, wherein each V gene segment is different from all other V gene segments.

4. The method of claim 1, wherein the multiple $V_H$ heavy chain loci comprise any number or combination of the 39 functional human V gene segments.

5. The method of claim 4, wherein each different $V_H$ heavy chain locus is present as a single copy in the genome of the transgenic non-human mammal.

6. The method of claim 1, wherein each $V_H$ heavy chain locus comprises from one to forty D gene segments.

7. The method of claim 1, wherein the D gene Segments are human D gene segments.

8. The method of claim 1, wherein each $V_H$ heavy chain locus comprises from one to twenty J gene segments.

9. The method of claim 1, wherein the J gene segments are human J gene segments.

10. The method of claim 1, wherein each $V_H$ heavy chain locus comprises one or more V gene segments, twenty-five functional human D gene segments and 6 human J gene segments.

11. The method of claim 1, wherein each gene segment encoding a heavy chain constant region comprises one or more heavy chain constant region exons of the $C\delta$, $C\gamma_{1-4}$, $C\mu$, $C\varepsilon$ or $C\alpha_{1-2}$ classes, with the proviso that the heavy chain constant region gene segments do not express a $C_H1$ domain.

12. The method of claim 1, wherein the heavy chain constant region is of human origin.

13. The method of claim 1, wherein the transgenic non-human mammal is a rodent.

14. The method of claim 13, wherein the rodent is a mouse.

15. A transgenic non-human mammal comprising more than one heterologous $V_H$ heavy chain locus as defined in claim 1.

16. A method for the production of heavy chain-only antibodies comprising:
   a) immunising a transgenic non-human mammal of claim 15 with an antigen; and
   b) isolating antigen-specific heavy chain-only antibodies.

17. A method of producing high affinity, antigen-specific $V_H$ heavy chain-only antibodies comprising:
   a) immunising a transgenic non-human mammal according to claim 15 with an antigen;
   b) generating B-cell hybridomas;
   c) selecting cells expressing antigen-specific heavy chain-only antibody; and
   d) isolating antigen-specific heavy chain-only antibody.

* * * * *

UNITED STATES PATENT AND TRADEMARK OFFICE
CERTIFICATE OF CORRECTION

| | | |
|---|---|---|
| PATENT NO. | : 10,638,735 B2 | Page 1 of 1 |
| APPLICATION NO. | : 14/962335 | |
| DATED | : May 5, 2020 | |
| INVENTOR(S) | : Grosveld et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 194 days.

Signed and Sealed this
Twenty-fourth Day of November, 2020

Andrei Iancu
*Director of the United States Patent and Trademark Office*